United States Patent
Kittle et al.

(10) Patent No.: US 12,234,273 B2
(45) Date of Patent: Feb. 25, 2025

(54) PROGRAMMABLE IMMUNOCYTE RECEPTOR COMPLEX SYSTEM

(71) Applicant: Fundamental Solutions Corporation, Easton, PA (US)

(72) Inventors: Joseph D. Kittle, The Plains, OH (US); Joel S. Lwande, Athens, OH (US); Yuanyuan Tang, Athens, OH (US); Shengwen Liang, Athens, OH (US)

( * ) Notice: Subject to any disclaimer, the term of this patent is extended or adjusted under 35 U.S.C. 154(b) by 787 days.

(21) Appl. No.: 16/897,885

(22) Filed: Jun. 10, 2020

(65) Prior Publication Data

US 2020/0299352 A1    Sep. 24, 2020

Related U.S. Application Data

(62) Division of application No. 16/353,337, filed on Mar. 14, 2019, now abandoned.

(60) Provisional application No. 62/651,916, filed on Apr. 3, 2018, provisional application No. 62/643,378, filed on Mar. 15, 2018.

(51) Int. Cl.
| | | |
|---|---|---|
| *C07K 14/725* | (2006.01) | |
| *A61K 39/00* | (2006.01) | |
| *C07K 14/36* | (2006.01) | |
| *C07K 14/47* | (2006.01) | |
| *C07K 14/735* | (2006.01) | |
| *C12N 5/0783* | (2010.01) | |

(52) U.S. Cl.
CPC ...... *C07K 14/7051* (2013.01); *A61K 39/4611* (2023.05); *A61K 39/464404* (2023.05); *A61K 39/464412* (2023.05); *C07K 14/36* (2013.01); *C07K 14/47* (2013.01); *C07K 14/70535* (2013.01); *C12N 5/0636* (2013.01)

(58) Field of Classification Search
None
See application file for complete search history.

(56) References Cited

U.S. PATENT DOCUMENTS

| | | |
|---|---|---|
| 5,723,584 A | 3/1998 | Schatz et al. |
| 5,874,239 A | 2/1999 | Schatz et al. |
| 5,932,433 A | 8/1999 | Schatz et al. |
| 9,752,199 B2 | 9/2017 | Zupancic et al. |
| 9,850,546 B2 | 12/2017 | Zupancic et al. |
| 9,850,547 B2 | 12/2017 | Zupancic et al. |
| 9,850,548 B2 | 12/2017 | Zupancic et al. |
| 2017/0258835 A1 | 9/2017 | Zhao et al. |
| 2019/0284255 A1 | 9/2019 | Kittle et al. |

FOREIGN PATENT DOCUMENTS

WO    WO 2004/018509 A1    3/2004

OTHER PUBLICATIONS

Lohmueller et al. "mSA2 affinity-enhanced biotin-binding CAR T cells for universal tumor targeting" (2018), Oncoimmunology, vol. 7, No. 1, e1368604, pp. 1-6. (Year: 2018).*
James, "Tuning ITAM multiplicity on T cell receptors can control potency and selectivity to ligand density", (May 2018), Sci Signal, 11: 1-9. (Year: 2018).*
https://blast.ncbi.nlm.nih.gov/Blast.cgi
Lee, Jeong Min, et al. "A rhizavidin monomer with nearly multimeric avidin-like binding stability against biotin conjugates." Angewandte Chemie International Edition 55.10 (2016): 3393-3397.
Lim, Kok Hong, et al. "Stable, high-affinity streptavidin monomer for protein labeling and monovalent biotin detection." Biotechnology and bioengineering 110.1 (2013): 57-67.
Lohmueller, J.J., et al., "mSA2 affinity-enhanced biotin-binding CAR T cells for universal tumor targeting," Oncoimmunology, 2018, 7(1):e1368604, 6 pgs.
Masuda, Atsuhiro, et al. "Role of Fc Receptors as a therapeutic target." Inflammation & Allergy-Drug Targets (Formerly Current Drug Targets-Inflammation & Allergy) 8.1 (2009): 80-86.
International Search Report and Written Opinion dated Jun. 7, 2019 for Application No. PCT/US2019/022245, 9 pgs.

* cited by examiner

*Primary Examiner* — Teresa E Knight

(57) ABSTRACT

A programmable receptor complex expressed by an immunocyte, wherein the programmable receptor complex includes a plurality of native or endogenously expressed receptor subunits, wherein the native or endogenously expressed receptor subunits have been engineered or modified to include FcγRI receptor components, biotin-binding components, or both, and wherein the FcγRI receptor components and biotin-binding components are operative to bind to target detector molecules that bind to or otherwise interact with predetermined targets.

18 Claims, 75 Drawing Sheets

Specification includes a Sequence Listing.

mFcγRI-CD3ζ (Heterozygous Insertion into γδTCR Complex)

mFcγRI-CD3ζ (Heterozygous Insertion into γδTCR Complex), Mouse IgG pFSC005 (pEF1-Aeq)

pFSC048 (pVitro-blasti-Aeq-FcγRI-CD3ζ) (mFcγRI-CD3ζ)

pFSC074b (pUC-Kan-mSA2-CD3ζ-2A-Blasti) (mSA2-CD3ζ)

pFSC086 (pFSC083a-mSA2)

pFSC100 (pFSC095-eMA-LL-CD3ε-IRES-Blast) (eMA-CD3ε)

pFSC097 (pFSC095-FcγRI-CD3ε-IRES-Blasti)

pFSC098 (pFSC095-FcγRI-TRAC-IRES-Blasti)

pFSC094 (pFSC048-FcyRI-TRBC1-IRES-Blasti)

pFSC103 (pFSC102-eMA-LL-TRBC1-IRES-Blasti)

pFSC085 (pFSC083a-eMA-LL-CD3ζ-IRES-Blasti)

CYTOKINE RELEASE ASSAY

SEQUENCE LISTING

<160> NUMBER OF SEQ ID NOS: 18

<210> SEQ ID NO 1
<211> LENGTH: 591
<212> TYPE: DNA
<213> ORGANISM: Artificial Sequence
<220> FEATURE:
<223> OTHER INFORMATION: pEF1-Aeq

<400> SEQUENCE: 1

```
atggccacaa gcaaacaata ctcagtcaag cttacatcag acttcgacaa cccaagatgg      60
attggacgac acaagcatat gttcaatttc cttgatgtca accacaatgg aaaaatctct     120
```

-continued

```
cttgacgaga tggtctacaa ggcatctgat attgtcatca ataaccttgg agcaacacct      180
gagcaagcca aacgacacaa agatgctgta gaagccttct tcggaggagc tggaatgaaa      240
tatggtgtgg aaactgattg gcctgcatat attgaaggat ggaaaaaatt ggctactgat      300
gaattggaga aatacgccaa aaacgaacca cgctcatcc gtatatgggg tgatgctttg       360
tttgatatcg ttgacaaaga tcaaaatgga gccattacac tggatgaatg gaaagcatac     420
accaaagctg ctggtatcat ccaatcatca gaagattgcg aggaaacatt cagagtgtgc     480
gatattgatg aaagtggaca actcgatgtt gatgagatga caagacaaca tttaggattt     540
tggtacacca tggatcctgc ttgcgaaaag ctctacggtg gagctgtccc c              591
```

```
<210> SEQ ID NO 2
<211> LENGTH: 197
<212> TYPE: PRT
<213> ORGANISM: Artificial Sequence
<220> FEATURE:
<223> OTHER INFORMATION: pEF1-Aeq - AMINO ACID

<400> SEQUENCE: 2

Met Ala Thr Ser Lys Gln Tyr Ser Val Lys Leu Thr Ser Asp Phe Asp
1               5                   10                  15

Asn Pro Arg Trp Ile Gly Arg His Lys His Met Phe Asn Phe Leu Asp
                20                  25                  30

Val Asn His Asn Gly Lys Ile Ser Leu Asp Glu Met Val Tyr Lys Ala
            35                  40                  45

Ser Asp Ile Val Ile Asn Asn Leu Gly Ala Thr Pro Glu Gln Ala Lys
        50                  55                  60

Arg His Lys Asp Ala Val Glu Ala Phe Phe Gly Gly Ala Gly Met Lys
65                  70                  75                  80

Tyr Gly Val Glu Thr Asp Trp Pro Ala Tyr Ile Glu Gly Trp Lys Lys
                85                  90                  95

Leu Ala Thr Asp Glu Leu Glu Lys Tyr Ala Lys Asn Glu Pro Thr Leu
            100                 105                 110

Ile Arg Ile Trp Gly Asp Ala Leu Phe Asp Ile Val Asp Lys Asp Gln
        115                 120                 125

Asn Gly Ala Ile Thr Leu Asp Glu Trp Lys Ala Tyr Thr Lys Ala Ala
    130                 135                 140

Gly Ile Ile Gln Ser Ser Glu Asp Cys Glu Glu Thr Phe Arg Val Cys
145                 150                 155                 160

Asp Ile Asp Glu Ser Gly Gln Leu Asp Val Asp Glu Met Thr Arg Gln
                165                 170                 175

His Leu Gly Phe Trp Tyr Thr Met Asp Pro Ala Cys Glu Lys Leu Tyr
            180                 185                 190

Gly Gly Ala Val Pro
        195

<210> SEQ ID NO 3
<211> LENGTH: 1332
<212> TYPE: DNA
<213> ORGANISM: Artificial Sequence
<220> FEATURE:
<223> OTHER INFORMATION: CD3(Zeta)SS-Fc(Gamma)RI-CD3(Zeta)

<400> SEQUENCE: 3
atgaagtgga aggcgctttt caccgcggcc atcctgcagg cacagttgcc gattacagag      60
gcagaagtgg ttaatgccac caaggctgtg atcacccttgc agcctccatg ggtcagtatt    120
```

```
ttccagaagg aaaatgtcac tttatggtgt gagggggcctc acctgcctgg agacagttcc    180
acacaatggt ttatcaacgg aacagccgtt cagatctcca cgcctagtta tagcatccca    240
gaggccagtt ttcaggacag tggcgaatac aggtgtcaga taggttcctc aatgccaagt    300
gaccctgtgc agttgcaaat ccacaatgat tggctgctac tccaggcctc ccgcagagtc    360
ctcacagaag gagaacccct ggccttgagg tgtcacggat ggaagaataa actggtgtac    420
aatgtggttt tctatagaaa tggaaaatcc tttcagtttt cttcagattc ggaggtcgcc    480
attctgaaaa ccaacctgag tcacagcggc atctaccact gctcaggcac gggaagacac    540
cgctacacat ctgcaggagt gtccatcacg gtgaaagagc tgtttaccac gccagtgctg    600
agagcatccg tgtcatctcc cttcccggag gggagtctgg tcaccctgaa ctgtgagacg    660
aatttgctcc tgcagagacc cggcttacag cttcacttct ccttctacgt gggcagcaag    720
atcctggagt acaggaacac atcctcagag taccatatag caagggcgga aagagaagat    780
gctggattct actggtgtga ggtagccacg gaggacagca gtgtccttaa gcgcagccct    840
gagttggagc tccaagtgct tggtccccag tcatcagctc ctggttctgc ttctggttct    900
ggtcagagct ttggcctgct ggatcccaaa ctctgctacc tgctggatgg aatcctcttc    960
atctatggtg tcattctcac tgccttgttc ctgagagtga gttcagcag gagcgcagac   1020
gcccccgcgt accagcaggg ccagaaccag ctctataacg agctcaatct aggacgaaga   1080
gaggagtacg atgttttgga caagagacgt ggccgggacc ctgagatggg gggaaagccg   1140
cagagaagga gaaccctca ggaaggcctg tacaatgaac tgcagaaaga taagatggcg   1200
gaggcctaca gtgagattgg gatgaaaggc gagcgccgga ggggcaaggg gcacgatggc   1260
ctttaccagg gtctcagtac agccaccaag gacacctacg acgcccttca catgcaggcc   1320
ctgccccctc gc                                                       1332
```

<210> SEQ ID NO 4
<211> LENGTH: 444
<212> TYPE: PRT
<213> ORGANISM: Artificial Sequence
<220> FEATURE:
<223> OTHER INFORMATION: CD3(Zeta)SS-Fc(Gamma)RI-CD3(Zeta) - AMINO ACID

<400> SEQUENCE: 4

Met Lys Trp Lys Ala Leu Phe Thr Ala Ala Ile Leu Gln Ala Gln Leu
1               5                   10                  15

Pro Ile Thr Glu Ala Glu Val Val Asn Ala Thr Lys Ala Val Ile Thr
            20                  25                  30

Leu Gln Pro Pro Trp Val Ser Ile Phe Gln Lys Glu Asn Val Thr Leu
        35                  40                  45

Trp Cys Glu Gly Pro His Leu Pro Gly Asp Ser Ser Thr Gln Trp Phe
    50                  55                  60

Ile Asn Gly Thr Ala Val Gln Ile Ser Thr Pro Ser Tyr Ser Ile Pro
65                  70                  75                  80

Glu Ala Ser Phe Gln Asp Ser Gly Glu Tyr Arg Cys Gln Ile Gly Ser
                85                  90                  95

Ser Met Pro Ser Asp Pro Val Gln Leu Gln Ile His Asn Asp Trp Leu
            100                 105                 110

Leu Leu Gln Ala Ser Arg Arg Val Leu Thr Glu Gly Glu Pro Leu Ala
        115                 120                 125

Leu Arg Cys His Gly Trp Lys Asn Lys Leu Val Tyr Asn Val Val Phe
    130                 135                 140

Tyr Arg Asn Gly Lys Ser Phe Gln Phe Ser Ser Asp Ser Glu Val Ala
145                 150                 155                 160

Ile Leu Lys Thr Asn Leu Ser His Ser Gly Ile Tyr His Cys Ser Gly
            165                 170                 175

Thr Gly Arg His Arg Tyr Thr Ser Ala Gly Val Ser Ile Thr Val Lys
        180                 185                 190

Glu Leu Phe Thr Thr Pro Val Leu Arg Ala Ser Val Ser Ser Pro Phe
    195                 200                 205

Pro Glu Gly Ser Leu Val Thr Leu Asn Cys Glu Thr Asn Leu Leu Leu
210                 215                 220

Gln Arg Pro Gly Leu Gln Leu His Phe Ser Phe Tyr Val Gly Ser Lys
225                 230                 235                 240

Ile Leu Glu Tyr Arg Asn Thr Ser Ser Glu Tyr His Ile Ala Arg Ala
            245                 250                 255

Glu Arg Glu Asp Ala Gly Phe Tyr Trp Cys Glu Val Ala Thr Glu Asp
        260                 265                 270

Ser Ser Val Leu Lys Arg Ser Pro Glu Leu Glu Leu Gln Val Leu Gly
    275                 280                 285

Pro Gln Ser Ser Ala Pro Gly Ser Ala Ser Gly Ser Gly Gln Ser Phe
290                 295                 300

Gly Leu Leu Asp Pro Lys Leu Cys Tyr Leu Leu Asp Gly Ile Leu Phe
305                 310                 315                 320

Ile Tyr Gly Val Ile Leu Thr Ala Leu Phe Leu Arg Val Lys Phe Ser
            325                 330                 335

Arg Ser Ala Asp Ala Pro Ala Tyr Gln Gln Gly Gln Asn Gln Leu Tyr
        340                 345                 350

Asn Glu Leu Asn Leu Gly Arg Arg Glu Glu Tyr Asp Val Leu Asp Lys
    355                 360                 365

Arg Arg Gly Arg Asp Pro Glu Met Gly Gly Lys Pro Gln Arg Arg Lys
370                 375                 380

Asn Pro Gln Glu Gly Leu Tyr Asn Glu Leu Gln Lys Asp Lys Met Ala
385                 390                 395                 400

Glu Ala Tyr Ser Glu Ile Gly Met Lys Gly Glu Arg Arg Arg Gly Lys
            405                 410                 415

Gly His Asp Gly Leu Tyr Gln Gly Leu Ser Thr Ala Thr Lys Asp Thr
        420                 425                 430

Tyr Asp Ala Leu His Met Gln Ala Leu Pro Pro Arg
        435                 440

<210> SEQ ID NO 5
<211> LENGTH: 855
<212> TYPE: DNA
<213> ORGANISM: Artificial Sequence
<220> FEATURE:
<223> OTHER INFORMATION: CD3(Zeta)SS-mSA2-CD3(Zeta)

<400> SEQUENCE: 5
atgaagtgga aggcgctttt caccgcggcc atcctgcagg cacagttgcc gattacagag      60
gcagccgagg ccggtatcac tggaacctgg tacaaccagc acggatccac attcaccgtg     120
accgccggtg ctgacggaaa tctgaccgga cagtacgaga tcggggctca gggcaccggt     180
tgtcagaact ccccttacac cctcactggg agatacaacg caccaagct ggaatggagg     240 gtggaatgga caactccac cgaaaactgc cattcccgca ctgagtggcg cggacagtat     300
caggggggag ccgaagcgcg gatcaacacc caatggaacc tgacctacga gggcgggagc     360

```
ggacccgcga ctgagcaggg ccaggatacg ttcactaagg tcaagggttc tgcttctggt    420
tctggtcaga gctttggcct gctggatccc aaactctgct acctgctgga tggaatcctc    480
ttcatctatg gtgtcattct cactgccttg ttcctgagag tgaagttcag caggagcgca    540 gacgccccg cgtaccagca gggccagaac cagctctata cgagctcaa tctaggacga    600 agagaggagt acgatgtttt ggacaagaga cgtggccggg accctgagat gggggggaaag    660 ccgcagagaa ggaagaaccc tcaggaaggc ctgtacaatg aactgcagaa agataagatg    720
gcggaggcct acagtgagat tgggatgaaa ggcgagcgcc ggaggggcaa ggggcacgat    780
ggcctttacc agggtctcag tacagccacc aaggacacct acgacgccct tcacatgcag    840
gccctgcccc ctcgc                                                      855
```

<210> SEQ ID NO 6
<211> LENGTH: 285
<212> TYPE: PRT
<213> ORGANISM: Artificial Sequence
<220> FEATURE:
<223> OTHER INFORMATION: CD3(Zeta)SS-mSA2-CD3Zeta) - AMINO ACID

<400> SEQUENCE: 6

```
Met Lys Trp Lys Ala Leu Phe Thr Ala Ala Ile Leu Gln Ala Gln Leu
1               5                   10                  15

Pro Ile Thr Glu Ala Ala Glu Ala Gly Ile Thr Gly Thr Trp Tyr Asn
            20                  25                  30

Gln His Gly Ser Thr Phe Thr Val Thr Ala Gly Ala Asp Gly Asn Leu
        35                  40                  45

Thr Gly Gln Tyr Glu Asn Arg Ala Gln Gly Thr Gly Cys Gln Asn Ser
    50                  55                  60

Pro Tyr Thr Leu Thr Gly Arg Tyr Asn Gly Thr Lys Leu Glu Trp Arg
65                  70                  75                  80

Val Glu Trp Asn Asn Ser Thr Glu Asn Cys His Ser Arg Thr Glu Trp
                85                  90                  95

Arg Gly Gln Tyr Gln Gly Gly Ala Glu Ala Arg Ile Asn Thr Gln Trp
            100                 105                 110

Asn Leu Thr Tyr Glu Gly Gly Ser Gly Pro Ala Thr Glu Gln Gly Gln
        115                 120                 125

Asp Thr Phe Thr Lys Val Lys Gly Ser Ala Ser Gly Ser Gly Gln Ser
    130                 135                 140

Phe Gly Leu Leu Asp Pro Lys Leu Cys Tyr Leu Leu Asp Gly Ile Leu
145                 150                 155                 160

Phe Ile Tyr Gly Val Ile Leu Thr Ala Leu Phe Leu Arg Val Lys Phe
                165                 170                 175

Ser Arg Ser Ala Asp Ala Pro Ala Tyr Gln Gln Gly Gln Asn Gln Leu
            180                 185                 190

Tyr Asn Glu Leu Asn Leu Gly Arg Arg Glu Glu Tyr Asp Val Leu Asp
        195                 200                 205

Lys Arg Arg Gly Arg Asp Pro Glu Met Gly Gly Lys Pro Gln Arg Arg
    210                 215                 220

Lys Asn Pro Gln Glu Gly Leu Tyr Asn Glu Leu Gln Lys Asp Lys Met
225                 230                 235                 240

Ala Glu Ala Tyr Ser Glu Ile Gly Met Lys Gly Glu Arg Arg Arg Gly
                245                 250                 255

Lys Gly His Asp Gly Leu Tyr Gln Gly Leu Ser Thr Ala Thr Lys Asp
            260                 265                 270
```

Thr Tyr Asp Ala Leu His Met Gln Ala Leu Pro Pro Arg
            275                 280                 285

<210> SEQ ID NO 7
<211> LENGTH: 1044
<212> TYPE: DNA
<213> ORGANISM: Artificial Sequence
<220> FEATURE:
<223> OTHER INFORMATION: CD3(Zeta)SS-eMA-CD3(Epsilon)

<400> SEQUENCE: 7

| | | |
|---|---|---|
| atgaagtgga aggcgctttt caccgcggcc atcctgcagg cacagttgcc gattacagag | 60 |
| gcattcgacg ccagcaactt caaggatttc tcgtccatcg cttccgcctc ctcctcctgg | 120 |
| caaaatcagc acggatcaac catgattatc caagtggact cgttcgggaa cgtgtcgggt | 180 |
| caatacgtga atcgcgccga gggaactggc tgtcagaact caccatatcc cctgaccgga | 240 |
| cgggtcaacg gcactttcat cgacttcagc gtgaagtgga acaactccac ggaaaactgc | 300 |
| aacagcaaca cccagtggac tggatacgca caggtcaacg gaacaacac cgagatcgtg | 360 |
| accagatgga acctcaaata cgagggcgga tccggtcctg cgatttggca gggccaggat | 420 |
| acatttcagt acgtgcctac aaccgaaggt tccaaaggag gctcaggagg ttctgcttct | 480 |
| ggttctggtg atggtaatga agaaatgggt ggtattacac agacaccata taagtctcc | 540 |
| atctctggaa ccacagtaat attgacatgc cctcagtatc ctggatctga aatactatgg | 600 |
| caacacaatg ataaaaacat aggcggtgat gaggatgata aaacatagg cagtgatgag | 660 |
| gatcacctgt cactgaagga attttcagaa ttggagcaaa gtggttatta tgtctgctac | 720 |
| cccagaggaa gcaaaccaga agatgcgaac ttttatctct acctgagggc aagagtgtgt | 780 |
| gagaactgca tggagatgga tgtgatgtcg gtggccacaa ttgtcatagt ggacatctgc | 840 |
| atcactgggg gcttgctgct gctggtttac tactggagca agaatagaaa ggccaaggcc | 900 |
| aagcctgtga cacgaggagc gggtgctggc ggcaggcaaa ggggacaaaa caaggagagg | 960 |
| ccaccacctg ttcccaaccc agactatgag cccatccgga aaggccagcg ggacctgtat | 1020 |
| tctggcctga atcagagacg catc | 1044 |

<210> SEQ ID NO 8
<211> LENGTH: 348
<212> TYPE: PRT
<213> ORGANISM: Artificial Sequence
<220> FEATURE:
<223> OTHER INFORMATION: CD3(Zeta)SS-eMA-CD3(Epsilon) - AMINO ACID

<400> SEQUENCE: 8

Met Lys Trp Lys Ala Leu Phe Thr Ala Ala Ile Leu Gln Ala Gln Leu
1               5                   10                  15

Pro Ile Thr Glu Ala Phe Asp Ala Ser Asn Phe Lys Asp Phe Ser Ser
            20                  25                  30

Ile Ala Ser Ala Ser Ser Ser Trp Gln Asn Gln His Gly Ser Thr Met
        35                  40                  45

Ile Ile Gln Val Asp Ser Phe Gly Asn Val Ser Gly Gln Tyr Val Asn
    50                  55                  60

Arg Ala Glu Gly Thr Gly Cys Gln Asn Ser Pro Tyr Pro Leu Thr Gly
65                  70                  75                  80

Arg Val Asn Gly Thr Phe Ile Asp Phe Ser Val Lys Trp Asn Asn Ser
                85                  90                  95

Thr Glu Asn Cys Asn Ser Asn Thr Gln Trp Thr Gly Tyr Ala Gln Val
            100                 105                 110

Asn Gly Asn Asn Thr Glu Ile Val Thr Arg Trp Asn Leu Lys Tyr Glu
        115                 120                 125

Gly Gly Ser Gly Pro Ala Ile Trp Gln Gly Gln Asp Thr Phe Gln Tyr
    130                 135                 140

Val Pro Thr Thr Glu Gly Ser Lys Gly Gly Ser Gly Gly Ser Ala Ser
145                 150                 155                 160

Gly Ser Gly Asp Gly Asn Glu Glu Met Gly Gly Ile Thr Gln Thr Pro
                165                 170                 175

Tyr Lys Val Ser Ile Ser Gly Thr Thr Val Ile Leu Thr Cys Pro Gln
            180                 185                 190

Tyr Pro Gly Ser Glu Ile Leu Trp Gln His Asn Asp Lys Asn Ile Gly
            195                 200                 205

Gly Asp Glu Asp Asp Lys Asn Ile Gly Ser Asp Glu Asp His Leu Ser
        210                 215                 220

Leu Lys Glu Phe Ser Glu Leu Glu Gln Ser Gly Tyr Tyr Val Cys Tyr
225                 230                 235                 240

Pro Arg Gly Ser Lys Pro Glu Asp Ala Asn Phe Tyr Leu Tyr Leu Arg
                245                 250                 255

Ala Arg Val Cys Glu Asn Cys Met Glu Met Asp Val Met Ser Val Ala
            260                 265                 270

Thr Ile Val Ile Val Asp Ile Cys Ile Thr Gly Gly Leu Leu Leu Leu
        275                 280                 285

Val Tyr Tyr Trp Ser Lys Asn Arg Lys Ala Lys Ala Lys Pro Val Thr
        290                 295                 300

Arg Gly Ala Gly Ala Gly Gly Arg Gln Arg Gly Gln Asn Lys Glu Arg
305                 310                 315                 320

Pro Pro Pro Val Pro Asn Pro Asp Tyr Glu Pro Ile Arg Lys Gly Gln
                325                 330                 335

Arg Asp Leu Tyr Ser Gly Leu Asn Gln Arg Arg Ile
            340                 345

<210> SEQ ID NO 9
<211> LENGTH: 1461
<212> TYPE: DNA
<213> ORGANISM: Artificial Sequence
<220> FEATURE:
<223> OTHER INFORMATION: CD3(Zeta)SS-Fc(Gamma)RI-CD3(Epsilon)

<400> SEQUENCE: 9
atgaagtgga aggcgctttt caccgcggcc atcctgcagg cacagttgcc gattacagag      60
gcagaagtgg ttaatgccac caaggctgtg atcaccttgc agcctccatg ggtcagtatt     120
ttccagaagg aaaatgtcac tttatggtgt gagggcctc acctgcctgg agacagttcc     180
acacaatggt ttatcaacgg aacagccgtt cagatctcca cgcctagtta tagcatccca     240
gaggccagtt tcaggacag tggcgaatac aggtgtcaga taggttcctc aatgccaagt     300
gaccctgtgc agttgcaaat ccacaatgat tggctgctac tccaggcctc ccgcagagtc     360
ctcacagaag gagaacccct ggccttgagg tgtcacggat ggaagaataa actggtgtac     420
aatgtggttt ctatagaaa tggaaaatcc tttcagtttt cttcagattc ggaggtcgcc     480
attctgaaaa ccaacctgag tcacagcggc atctaccact gctcaggcac gggaagacac     540
cgctacacat ctgcaggagt gtccatcacg tgaaagagc tgtttaccac gccagtgctg     600
agagcatccg tgtcatctcc cttcccggag gggagtctgg tcaccctgaa ctgtgagacg     660
aatttgctcc tgcagagacc cggcttacag cttcacttct ccttctacgt gggcagcaag     720

```
atcctggagt acaggaacac atcctcagag taccatatag caagggcgga aagagaagat    780
gctggattct actggtgtga ggtagccacg gaggacagca gtgtccttaa gcgcagccct    840
gagttggagc tccaagtgct tggtccccag tcatcagctc ctggttctgc ttctggttct    900
ggtgatggta atgaagaaat gggtggtatt acacagacac catataaagt ctccatctct    960
ggaaccacag taatattgac atgccctcag tatcctggat ctgaaatact atggcaacac   1020
aatgataaaa acataggcgg tgatgaggat gataaaaaca taggcagtga tgaggatcac   1080
ctgtcactga aggaatttc agaattggag caaagtggtt attatgtctg ctaccccaga    1140
ggaagcaaac cagaagatgc gaactttat ctctacctga gggcaagagt gtgtgagaac    1200
tgcatggaga tggatgtgat gtcggtggcc acaattgtca tagtggacat ctgcatcact   1260
gggggcttgc tgctgctggt ttactactgg agcaagaata gaaaggccaa ggccaagcct   1320
gtgacacgag gagcgggtgc tggcggcagg caaaggggac aaaacaagga gaggccacca   1380
cctgttccca acccagacta tgagcccatc cggaaaggcc agcgggacct gtattctggc   1440
ctgaatcaga gacgcatctg a                                             1461
```

<210> SEQ ID NO 10
<211> LENGTH: 486
<212> TYPE: PRT
<213> ORGANISM: Artificial Sequence
<220> FEATURE:
<223> OTHER INFORMATION: CD3(Zeta)SS-Fc(Gamma)RI-CD3(Epsilon) - AMINO ACID

<400> SEQUENCE: 10

```
Met Lys Trp Lys Ala Leu Phe Thr Ala Ala Ile Leu Gln Ala Gln Leu
1               5                   10                  15

Pro Ile Thr Glu Ala Glu Val Val Asn Ala Thr Lys Ala Val Ile Thr
                20                  25                  30

Leu Gln Pro Pro Trp Val Ser Ile Phe Gln Lys Glu Asn Val Thr Leu
            35                  40                  45

Trp Cys Glu Gly Pro His Leu Pro Gly Asp Ser Ser Thr Gln Trp Phe
        50                  55                  60

Ile Asn Gly Thr Ala Val Gln Ile Ser Thr Pro Ser Tyr Ser Ile Pro
65                  70                  75                  80

Glu Ala Ser Phe Gln Asp Ser Gly Glu Tyr Arg Cys Gln Ile Gly Ser
                85                  90                  95

Ser Met Pro Ser Asp Pro Val Gln Leu Gln Ile His Asn Asp Trp Leu
                100                 105                 110

Leu Leu Gln Ala Ser Arg Arg Val Leu Thr Glu Gly Glu Pro Leu Ala
            115                 120                 125

Leu Arg Cys His Gly Trp Lys Asn Lys Leu Val Tyr Asn Val Val Phe
        130                 135                 140

Tyr Arg Asn Gly Lys Ser Phe Gln Phe Ser Ser Asp Ser Glu Val Ala
145                 150                 155                 160

Ile Leu Lys Thr Asn Leu Ser His Ser Gly Ile Tyr His Cys Ser Gly
                165                 170                 175

Thr Gly Arg His Arg Tyr Thr Ser Ala Gly Val Ser Ile Thr Val Lys
                180                 185                 190

Glu Leu Phe Thr Thr Pro Val Leu Arg Ala Ser Val Ser Ser Pro Phe
            195                 200                 205

Pro Glu Gly Ser Leu Val Thr Leu Asn Cys Glu Thr Asn Leu Leu Leu
        210                 215                 220
```

Gln Arg Pro Gly Leu Gln Leu His Phe Ser Phe Tyr Val Gly Ser Lys
225                 230                 235                 240

Ile Leu Glu Tyr Arg Asn Thr Ser Ser Glu Tyr His Ile Ala Arg Ala
            245                 250                 255

Glu Arg Glu Asp Ala Gly Phe Tyr Trp Cys Glu Val Ala Thr Glu Asp
        260                 265                 270

Ser Ser Val Leu Lys Arg Ser Pro Glu Leu Glu Leu Gln Val Leu Gly
    275                 280                 285

Pro Gln Ser Ser Ala Pro Gly Ser Ala Ser Gly Ser Gly Asp Gly Asn
290                 295                 300

Glu Glu Met Gly Gly Ile Thr Gln Thr Pro Tyr Lys Val Ser Ile Ser
305                 310                 315                 320

Gly Thr Thr Val Ile Leu Thr Cys Pro Gln Tyr Pro Gly Ser Glu Ile
                325                 330                 335

Leu Trp Gln His Asn Asp Lys Asn Ile Gly Gly Asp Glu Asp Asp Lys
                340                 345                 350

Asn Ile Gly Ser Asp Glu Asp His Leu Ser Leu Lys Glu Phe Ser Glu
            355                 360                 365

Leu Glu Gln Ser Gly Tyr Tyr Val Cys Tyr Pro Arg Gly Ser Lys Pro
370                 375                 380

Glu Asp Ala Asn Phe Tyr Leu Tyr Leu Arg Ala Arg Val Cys Glu Asn
385                 390                 395                 400

Cys Met Glu Met Asp Val Met Ser Val Ala Thr Ile Val Ile Val Asp
                405                 410                 415

Ile Cys Ile Thr Gly Gly Leu Leu Leu Leu Val Tyr Tyr Trp Ser Lys
                420                 425                 430

Asn Arg Lys Ala Lys Ala Lys Pro Val Thr Arg Gly Ala Gly Ala Gly
            435                 440                 445

Gly Arg Gln Arg Gly Gln Asn Lys Glu Arg Pro Pro Pro Val Pro Asn
        450                 455                 460

Pro Asp Tyr Glu Pro Ile Arg Lys Gly Gln Arg Asp Leu Tyr Ser Gly
465                 470                 475                 480

Leu Asn Gln Arg Arg Ile
            485

<210> SEQ ID NO 11
<211> LENGTH: 1329
<212> TYPE: DNA
<213> ORGANISM: Artificial Sequence
<220> FEATURE:
<223> OTHER INFORMATION: CD3(Zeta)SS-Fc(gamma)RI-TRAC

<400> SEQUENCE: 11

| | | | | | |
|---|---|---|---|---|---|
| atgaagtgga | aggcgctttt | caccgcggcc | atcctgcagg | cacagttgcc | gattacagag | 60 |
| gcagaagtgg | ttaatgccac | caaggctgtg | atcaccttgc | agcctccatg | ggtcagtatt | 120 |
| ttccagaagg | aaaatgtcac | tttatggtgt | gaggggcctc | acctgcctgg | agacagttcc | 180 |
| acacaatggt | ttatcaacgg | aacagccgtt | cagatctcca | cgcctagtta | tagcatccca | 240 |
| gaggccagtt | tcaggacag | tggcgaatac | aggtgtcaga | taggttcctc | aatgccaagt | 300 |
| gaccctgtgc | agttgcaaat | ccacaatgat | tggctgctac | tccaggcctc | ccgcagagtc | 360 |
| ctcacagaag | gagaacccct | ggccttgagg | tgtcacggat | ggaagaataa | actggtgtac | 420 |
| aatgtggttt | tctatagaaa | tggaaaatcc | tttcagtttt | cttcagattc | ggaggtcgcc | 480 |
| attctgaaaa | ccaacctgag | tcacagcggc | atctaccact | gctcaggcac | gggaagacac | 540 |

```
cgctacacat ctgcaggagt gtccatcacg gtgaaagagc tgtttaccac gccagtgctg    600
agagcatccg tgtcatctcc cttcccggag gggagtctgg tcaccctgaa ctgtgagacg    660
aatttgctcc tgcagagacc cggcttacag cttcacttct ccttctacgt gggcagcaag    720
atcctggagt acaggaacac atcctcagag taccatatag caagggcgga agagaagat     780 gctggattct actggtgtga ggtagccacg gaggacagca gtgtccttaa cgcagccct     840 gagttggagc tccaagtgct tggtccccag tcatcagctc ctggttctgc ttctggttct    900
ggtccaaata tccagaaccc tgaccctgcc gtgtaccagc tgagagactc taaatccagt    960
gacaagtctg tctgcctatt caccgatttt gattctcaaa caaatgtgtc acaaagtaag   1020
gattctgatg tgtatatcac agacaaaact gtgctagaca tgaggtctat ggacttcaag   1080
agcaacagtg ctgtggcctg gagcaacaaa tctgactttg catgtgcaaa cgccttcaac   1140
aacagcatta ttccagaaga caccttcttc cccagcccag aaagttcctg tgatgtcaag   1200
ctggtcgaga aaagctttga aacagatacg aacctaaaact ttcaaaacct gtcagtgatt   1260
gggttccgaa tcctcctcct gaaagtggcc gggtttaatc tgctcatgac gctgcggctg   1320
tggtccagc                                                          1329
```

```
<210> SEQ ID NO 12
<211> LENGTH: 443
<212> TYPE: PRT
<213> ORGANISM: Artificial Sequence
<220> FEATURE:
<223> OTHER INFORMATION: CD3(Zeta)SS-Fc(Gamma)RI-TRAC - AMINO ACID

<400> SEQUENCE: 12
```

```
Met Lys Trp Lys Ala Leu Phe Thr Ala Ala Ile Leu Gln Ala Gln Leu
1               5                   10                  15

Pro Ile Thr Glu Ala Glu Val Val Asn Ala Thr Lys Ala Val Ile Thr
            20                  25                  30

Leu Gln Pro Pro Trp Val Ser Ile Phe Gln Lys Glu Asn Val Thr Leu
        35                  40                  45

Trp Cys Glu Gly Pro His Leu Pro Gly Asp Ser Ser Thr Gln Trp Phe
    50                  55                  60

Ile Asn Gly Thr Ala Val Gln Ile Ser Thr Pro Ser Tyr Ser Ile Pro
65                  70                  75                  80

Glu Ala Ser Phe Gln Asp Ser Gly Glu Tyr Arg Cys Gln Ile Gly Ser
                85                  90                  95

Ser Met Pro Ser Asp Pro Val Gln Leu Gln Ile His Asn Asp Trp Leu
            100                 105                 110

Leu Leu Gln Ala Ser Arg Arg Val Leu Thr Glu Gly Glu Pro Leu Ala
        115                 120                 125

Leu Arg Cys His Gly Trp Lys Asn Lys Leu Val Tyr Asn Val Val Phe
    130                 135                 140

Tyr Arg Asn Gly Lys Ser Phe Gln Phe Ser Ser Asp Ser Glu Val Ala
145                 150                 155                 160

Ile Leu Lys Thr Asn Leu Ser His Ser Gly Ile Tyr His Cys Ser Gly
                165                 170                 175

Thr Gly Arg His Arg Tyr Thr Ser Ala Gly Val Ser Ile Thr Val Lys
            180                 185                 190

Glu Leu Phe Thr Thr Pro Val Leu Arg Ala Ser Val Ser Ser Pro Phe
        195                 200                 205

Pro Glu Gly Ser Leu Val Thr Leu Asn Cys Glu Thr Asn Leu Leu Leu
```

```
                210                 215                 220
Gln Arg Pro Gly Leu Gln Leu His Phe Ser Phe Tyr Val Gly Ser Lys
225                 230                 235                 240

Ile Leu Glu Tyr Arg Asn Thr Ser Ser Glu Tyr His Ile Ala Arg Ala
                245                 250                 255

Glu Arg Glu Asp Ala Gly Phe Tyr Trp Cys Glu Val Ala Thr Glu Asp
                260                 265                 270

Ser Ser Val Leu Lys Arg Ser Pro Glu Leu Glu Leu Gln Val Leu Gly
                275                 280                 285

Pro Gln Ser Ser Ala Pro Gly Ser Ala Ser Gly Ser Gly Pro Asn Ile
                290                 295                 300

Gln Asn Pro Asp Pro Ala Val Tyr Gln Leu Arg Asp Ser Lys Ser Ser
305                 310                 315                 320

Asp Lys Ser Val Cys Leu Phe Thr Asp Phe Asp Ser Gln Thr Asn Val
                325                 330                 335

Ser Gln Ser Lys Asp Ser Asp Val Tyr Ile Thr Asp Lys Thr Val Leu
                340                 345                 350

Asp Met Arg Ser Met Asp Phe Lys Ser Asn Ser Ala Val Ala Trp Ser
                355                 360                 365

Asn Lys Ser Asp Phe Ala Cys Ala Asn Ala Phe Asn Asn Ser Ile Ile
                370                 375                 380

Pro Glu Asp Thr Phe Phe Pro Ser Pro Glu Ser Ser Cys Asp Val Lys
385                 390                 395                 400

Leu Val Glu Lys Ser Phe Glu Thr Asp Thr Asn Leu Asn Phe Gln Asn
                405                 410                 415

Leu Ser Val Ile Gly Phe Arg Ile Leu Leu Leu Lys Val Ala Gly Phe
                420                 425                 430

Asn Leu Leu Met Thr Leu Arg Leu Trp Ser Ser
                435                 440

<210> SEQ ID NO 13
<211> LENGTH: 1434
<212> TYPE: DNA
<213> ORGANISM: Artificial Sequence
<220> FEATURE:
<223> OTHER INFORMATION: CD3(Zeta)SS-Fc(Gamma)RI-TRBC1

<400> SEQUENCE: 13
atgaagtgga aggcgctttt caccgcggcc atcctgcagg cacagttgcc gattacagag    60
gcagaagtgg ttaatgccac caaggctgtg atcaccttgc agcctccatg ggtcagtatt   120
ttccagaagg aaaatgtcac tttatggtgt gaggggcctc acctgcctgg agacagttcc   180
acacaatggt ttatcaacgg aacagccgtt cagatctcca cgcctagtta tagcatccca   240
gaggccagtt tcaggacag tggcgaatac aggtgtcaga taggttcctc aatgccaagt   300
gaccctgtgc agttgcaaat ccacaatgat tggctgctac tccaggcctc ccgcagagtc   360
ctcacagaag gagaacccct ggccttgagg tgtcacggat ggaagaataa actggtgtac   420
aatgtggttt tctatagaaa tggaaaatcc tttcagtttt cttcagattc ggaggtcgcc   480
attctgaaaa ccaacctgag tcacagcggc atctaccact gctcaggcac gggaagacac   540
cgctacacat ctgcaggagt gtccatcacg gtgaaagagc tgtttaccac gccagtgctg   600
agagcatccg tgtcatctcc cttcccggag gggagtctgg tcaccctgaa ctgtgagacg   660
aatttgctcc tgcagagacc cggcttacag cttcacttct ccttctacgt gggcagcaag   720
atcctggagt acaggaacac atcctcagag taccatatag caagggcgga agagaagat   780
```

```
gctggattct actggtgtga ggtagccacg gaggacagca gtgtccttaa gcgcagccct    840
gagttggagc tccaagtgct tggtccccag tcatcagctc ctggttctgc ttctggttct    900
ggtgaggacc tgaacaaggt gttcccaccc gaggtcgctg tgtttgagcc atcagaagca    960
gagatctccc acacccaaaa ggccacactg gtgtgcctgg ccacaggctt cttccccgac   1020
cacgtggagc tgagctggtg ggtgaatggg aaggaggtgc acagtggggt cagcacagac   1080
ccgcagcccc tcaaggagca gcccgccctc aatgactcca gatactgcct gagcagccgc   1140
ctgagggtct cggccacctt ctggcagaac ccccgcaacc acttccgctg tcaagtccag   1200
ttctacgggc tctcggagaa tgacgagtgg acccaggata gggccaaacc cgtcacccag   1260
atcgtcagcg ccgaggcctg ggtagagca gactgtggct ttacctcggt gtcctaccag   1320 caagggtcc tgtctgccac catcctctat gagatcctgc tagggaaggc caccctgtat   1380
gctgtgctgg tcagcgccct tgtgttgatg gccatggtca agagaaagga tttc         1434
```

<210> SEQ ID NO 14
<211> LENGTH: 478
<212> TYPE: PRT
<213> ORGANISM: Artificial Sequence
<220> FEATURE:
<223> OTHER INFORMATION: CD3(Zeta)SS-Fc(Gamma)RI-TRBC1 - AMINO ACID

<400> SEQUENCE: 14

```
Met Lys Trp Lys Ala Leu Phe Thr Ala Ala Ile Leu Gln Ala Gln Leu
1               5                   10                  15

Pro Ile Thr Glu Ala Glu Val Val Asn Ala Thr Lys Ala Val Ile Thr
            20                  25                  30

Leu Gln Pro Pro Trp Val Ser Ile Phe Gln Lys Glu Asn Val Thr Leu
        35                  40                  45

Trp Cys Glu Gly Pro His Leu Pro Gly Asp Ser Ser Thr Gln Trp Phe
    50                  55                  60

Ile Asn Gly Thr Ala Val Gln Ile Ser Thr Pro Ser Tyr Ser Ile Pro
65                  70                  75                  80

Glu Ala Ser Phe Gln Asp Ser Gly Glu Tyr Arg Cys Gln Ile Gly Ser
                85                  90                  95

Ser Met Pro Ser Asp Pro Val Gln Leu Gln Ile His Asn Asp Trp Leu
            100                 105                 110

Leu Leu Gln Ala Ser Arg Arg Val Leu Thr Glu Gly Glu Pro Leu Ala
        115                 120                 125

Leu Arg Cys His Gly Trp Lys Asn Lys Leu Val Tyr Asn Val Val Phe
    130                 135                 140

Tyr Arg Asn Gly Lys Ser Phe Gln Phe Ser Ser Asp Ser Glu Val Ala
145                 150                 155                 160

Ile Leu Lys Thr Asn Leu Ser His Ser Gly Ile Tyr His Cys Ser Gly
                165                 170                 175

Thr Gly Arg His Arg Tyr Thr Ser Ala Gly Val Ser Ile Thr Val Lys
            180                 185                 190

Glu Leu Phe Thr Thr Pro Val Leu Arg Ala Ser Val Ser Ser Pro Phe
        195                 200                 205

Pro Glu Gly Ser Leu Val Thr Leu Asn Cys Glu Thr Asn Leu Leu Leu
    210                 215                 220

Gln Arg Pro Gly Leu Gln Leu His Phe Ser Phe Tyr Val Gly Ser Lys
225                 230                 235                 240

Ile Leu Glu Tyr Arg Asn Thr Ser Ser Glu Tyr His Ile Ala Arg Ala
```

|  | | 245 | | | | 250 | | | | 255 | |
|---|---|---|---|---|---|---|---|---|---|---|---|

Glu Arg Glu Asp Ala Gly Phe Tyr Trp Cys Glu Val Ala Thr Glu Asp
                260                 265                 270

Ser Ser Val Leu Lys Arg Ser Pro Glu Leu Glu Leu Gln Val Leu Gly
            275                 280                 285

Pro Gln Ser Ser Ala Pro Gly Ser Ala Ser Gly Ser Gly Glu Asp Leu
        290                 295                 300

Asn Lys Val Phe Pro Pro Glu Val Ala Val Phe Glu Pro Ser Glu Ala
305                 310                 315                 320

Glu Ile Ser His Thr Gln Lys Ala Thr Leu Val Cys Leu Ala Thr Gly
                325                 330                 335

Phe Phe Pro Asp His Val Glu Leu Ser Trp Trp Val Asn Gly Lys Glu
            340                 345                 350

Val His Ser Gly Val Ser Thr Asp Pro Gln Pro Leu Lys Glu Gln Pro
        355                 360                 365

Ala Leu Asn Asp Ser Arg Tyr Cys Leu Ser Ser Arg Leu Arg Val Ser
370                 375                 380

Ala Thr Phe Trp Gln Asn Pro Arg Asn His Phe Arg Cys Gln Val Gln
385                 390                 395                 400

Phe Tyr Gly Leu Ser Glu Asn Asp Glu Trp Thr Gln Asp Arg Ala Lys
            405                 410                 415

Pro Val Thr Gln Ile Val Ser Ala Glu Ala Trp Gly Arg Ala Asp Cys
        420                 425                 430

Gly Phe Thr Ser Val Ser Tyr Gln Gln Gly Val Leu Ser Ala Thr Ile
            435                 440                 445

Leu Tyr Glu Ile Leu Leu Gly Lys Ala Thr Leu Tyr Ala Val Leu Val
    450                 455                 460

Ser Ala Leu Val Leu Met Ala Met Val Lys Arg Lys Asp Phe
465                 470                 475

<210> SEQ ID NO 15
<211> LENGTH: 1020
<212> TYPE: DNA
<213> ORGANISM: Artificial Sequence
<220> FEATURE:
<223> OTHER INFORMATION: CD3(Zeta)SS-eMA-TRBC1

<400> SEQUENCE: 15
atgaagtgga aggcgctttt caccgcggcc atcctgcagg cacagttgcc gattacagag    60
gcattcgacg ccagcaactt caaggatttc tcgtccatcg cttccgcctc ctcctcctgg   120
caaaatcagc acggatcaac catgattatc caagtggact cgttcgggaa cgtgtcgggt   180
caatacgtga atcgcgccga gggaactggc tgtcagaact caccatatcc cctgaccgga   240
cgggtcaacg gcactttcat cgacttcagc gtgaagtgga caactccac ggaaaactgc   300 aacagcaaca cccagtggac tggatacgca caggtcaacg ggaacaacac cgagatcgtg   360
accagatgga acctcaaata cgagggcgga tccggtcctg cgatttggca gggccaggat   420
acatttcagt acgtgcctac aaccgaaggt tccaaggag gctcaggagg ttctgcttct   480
ggttctggtg aggaccctgaa caaggtgttc cacccgagg tcgctgtgtt tgagccatca   540
gaagcagaga tctcccacac ccaaaaggcc acactggtgt gcctggccac aggcttcttc   600
cccgaccacg tggagctgag ctggtgggtg aatgggaagg aggtgcacag tggggtcagc   660
acagaccccg agcccctcaa ggagcagccc gccctcaatg actccagata ctgcctgagc   720
agccgcctga gggtctcggc caccttctgg cagaacccc gcaaccactt ccgctgtcaa   780

```
gtccagttct acgggctctc ggagaatgac gagtggaccc aggataggc caaacccgtc    840 acccagatcg tcagcgccga ggcctggggt agagcagact gtggctttac ctcggtgtcc    900
taccagcaag ggtcctgtc tgccaccatc ctctatgaga tcctgctagg gaaggccacc    960
ctgtatgctg tgctggtcag cgcccttgtg ttgatggcca tggtcaagag aaaggatttc   1020
```

<210> SEQ ID NO 16
<211> LENGTH: 340
<212> TYPE: PRT
<213> ORGANISM: Artificial Sequence
<220> FEATURE:
<223> OTHER INFORMATION: CD3(Zeta)SS-eMA-TRBC1 - AMINO ACID

<400> SEQUENCE: 16

```
Met Lys Trp Lys Ala Leu Phe Thr Ala Ala Ile Leu Gln Ala Gln Leu
1               5                   10                  15

Pro Ile Thr Glu Ala Phe Asp Ala Ser Asn Phe Lys Asp Phe Ser Ser
                20                  25                  30

Ile Ala Ser Ala Ser Ser Trp Gln Asn Gln His Gly Ser Thr Met
            35                  40                  45

Ile Ile Gln Val Asp Ser Phe Gly Asn Val Ser Gly Gln Tyr Val Asn
        50                  55                  60

Arg Ala Glu Gly Thr Gly Cys Gln Asn Ser Pro Tyr Pro Leu Thr Gly
65                  70                  75                  80

Arg Val Asn Gly Thr Phe Ile Asp Phe Ser Val Lys Trp Asn Asn Ser
                85                  90                  95

Thr Glu Asn Cys Asn Ser Asn Thr Gln Trp Thr Gly Tyr Ala Gln Val
            100                 105                 110

Asn Gly Asn Asn Thr Glu Ile Val Thr Arg Trp Asn Leu Lys Tyr Glu
        115                 120                 125

Gly Gly Ser Gly Pro Ala Ile Trp Gln Gly Gln Asp Thr Phe Gln Tyr
    130                 135                 140

Val Pro Thr Thr Glu Gly Ser Lys Gly Gly Ser Gly Gly Ser Ala Ser
145                 150                 155                 160

Gly Ser Gly Glu Asp Leu Asn Lys Val Phe Pro Pro Glu Val Ala Val
                165                 170                 175

Phe Glu Pro Ser Glu Ala Glu Ile Ser His Thr Gln Lys Ala Thr Leu
            180                 185                 190

Val Cys Leu Ala Thr Gly Phe Phe Pro Asp His Val Glu Leu Ser Trp
        195                 200                 205

Trp Val Asn Gly Lys Glu Val His Ser Gly Val Ser Thr Asp Pro Gln
    210                 215                 220

Pro Leu Lys Glu Gln Pro Ala Leu Asn Asp Ser Arg Tyr Cys Leu Ser
225                 230                 235                 240

Ser Arg Leu Arg Val Ser Ala Thr Phe Trp Gln Asn Pro Arg Asn His
                245                 250                 255

Phe Arg Cys Gln Val Gln Phe Tyr Gly Leu Ser Glu Asn Asp Glu Trp
            260                 265                 270

Thr Gln Asp Arg Ala Lys Pro Val Thr Gln Ile Val Ser Ala Glu Ala
        275                 280                 285

Trp Gly Arg Ala Asp Cys Gly Phe Thr Ser Val Ser Tyr Gln Gln Gly
    290                 295                 300

Val Leu Ser Ala Thr Ile Leu Tyr Glu Ile Leu Leu Gly Lys Ala Thr
305                 310                 315                 320
```

Leu Tyr Ala Val Leu Val Ser Ala Leu Val Leu Met Ala Met Val Lys
            325                 330                 335

Arg Lys Asp Phe
            340

<210> SEQ ID NO 17
<211> LENGTH: 918
<212> TYPE: DNA
<213> ORGANISM: Artificial Sequence
<220> FEATURE:
<223> OTHER INFORMATION: CD3(Zeta)SS-eMA-CD3(Zeta)

<400> SEQUENCE: 17

| | | |
|---|---|---|
| atgaagtgga aggcgctttt caccgcggcc atcctgcagg cacagttgcc gattacagag | 60 |
| gcattcgacg ccagcaactt caaggatttc tcgtccatcg cttccgcctc ctcctcctgg | 120 |
| caaaatcagc acggatcaac catgattatc caagtggact cgttcgggaa cgtgtcgggt | 180 |
| caatacgtga atcgcgccga gggaactggc tgtcagaact caccatatcc cctgaccgga | 240 |
| cgggtcaacg gcactttcat cgacttcagc gtgaagtgga caactccac ggaaaactgc | 300 |
| aacagcaaca cccagtggac tggatacgca caggtcaacg gaacaacac cgagatcgtg | 360 |
| accagatgga acctcaaata cgagggcgga tccggtcctg cgatttggca gggccaggat | 420 |
| acatttcagt acgtgcctac aaccgaaggt tccaaggag ctcaggagg ttctgcttct | 480 |
| ggttctggtc agagctttgg cctgctggat cccaaactct gctacctgct ggatggaatc | 540 |
| ctcttcatct atggtgtcat tctcactgcc ttgttcctga gagtgaagtt cagcaggagc | 600 |
| gcagacgccc ccgcgtacca gcagggccag aaccagctct ataacgagct caatctagga | 660 |
| cgaagagagg agtacgatgt tttggacaag agacgtggcc gggaccctga tggggggga | 720 |
| aagccgcaga gaaggaagaa ccctcaggaa ggcctgtaca tgaactgca gaaagataag | 780 |
| atggcggagg cctacagtga gattgggatg aaaggcgagc gccggagggg caaggggcac | 840 |
| gatggccttt accagggtct cagtacagcc accaaggaca cctacgacgc ccttcacatg | 900 |
| caggccctgc cccctcgc | 918 |

<210> SEQ ID NO 18
<211> LENGTH: 306
<212> TYPE: PRT
<213> ORGANISM: Artificial Sequence
<220> FEATURE:
<223> OTHER INFORMATION: CD3(Zeta)SS-eMA-CD3(Zeta) - AMINO ACID

<400> SEQUENCE: 18

Met Lys Trp Lys Ala Leu Phe Thr Ala Ala Ile Leu Gln Ala Gln Leu
1               5                   10                  15

Pro Ile Thr Glu Ala Phe Asp Ala Ser Asn Phe Lys Asp Phe Ser Ser
            20                  25                  30

Ile Ala Ser Ala Ser Ser Ser Trp Gln Asn Gln His Gly Ser Thr Met
        35                  40                  45

Ile Ile Gln Val Asp Ser Phe Gly Asn Val Ser Gly Gln Tyr Val Asn
    50                  55                  60

Arg Ala Glu Gly Thr Gly Cys Gln Asn Ser Pro Tyr Pro Leu Thr Gly
65                  70                  75                  80

Arg Val Asn Gly Thr Phe Ile Asp Phe Ser Val Lys Trp Asn Asn Ser
                85                  90                  95

Thr Glu Asn Cys Asn Ser Asn Thr Gln Trp Thr Gly Tyr Ala Gln Val
            100                 105                 110

```
                    -continued

Asn Gly Asn Asn Thr Glu Ile Val Thr Arg Trp Asn Leu Lys Tyr Glu
        115                 120             125

Gly Gly Ser Gly Pro Ala Ile Trp Gln Gly Gln Asp Thr Phe Gln Tyr
130             135                 140

Val Pro Thr Thr Glu Gly Ser Lys Gly Gly Ser Gly Gly Ser Ala Ser
145                 150             155                 160

Gly Ser Gly Gln Ser Phe Gly Leu Leu Asp Pro Lys Leu Cys Tyr Leu
                165             170             175

Leu Asp Gly Ile Leu Phe Ile Tyr Gly Val Ile Leu Thr Ala Leu Phe
            180             185             190

Leu Arg Val Lys Phe Ser Arg Ser Ala Asp Ala Pro Ala Tyr Gln Gln
            195             200             205

Gly Gln Asn Gln Leu Tyr Asn Glu Leu Asn Leu Gly Arg Arg Glu Glu
        210             215             220

Tyr Asp Val Leu Asp Lys Arg Arg Gly Arg Asp Pro Glu Met Gly Gly
225             230             235             240

Lys Pro Gln Arg Arg Lys Asn Pro Gln Glu Gly Leu Tyr Asn Glu Leu
                245             250             255

Gln Lys Asp Lys Met Ala Glu Ala Tyr Ser Glu Ile Gly Met Lys Gly
            260             265             270

Glu Arg Arg Arg Gly Lys Gly His Asp Gly Leu Tyr Gln Gly Leu Ser
        275             280             285

Thr Ala Thr Lys Asp Thr Tyr Asp Ala Leu His Met Gln Ala Leu Pro
        290             295             300

Pro Arg
305
```

PROGRAMMABLE IMMUNOCYTE RECEPTOR COMPLEX SYSTEM

CROSS-REFERENCE TO RELATED APPLICATIONS

This patent application is a divisional of U.S. patent application Ser. No. 16/353,337 filed on Mar. 14, 2019 and entitled "Programmable Immunocyte Receptor Complex System", which claimed the benefit of U.S. Provisional Patent Application Ser. No. 62/643,378 filed on Mar. 15, 2018 and entitled "Programmable Immunocyte Receptor Complex System", and U.S. Provisional Patent Application Ser. No. 62/651,916 filed on Apr. 3, 2018 and entitled "Programmable Immunocyte Receptor Complex System", the disclosures of which are hereby incorporated by reference herein in their entirety and made part of the present U.S. utility patent application for all purposes.

REFERENCE TO A SEQUENCE LISTING

A sequence listing in computer readable form (CRF) is on file. The sequence listing is in an ASCII text (.txt) file entitled SEQ ID NO 1-18_ST25.txt created on Mar. 14, 2019 and is 47 KB in size. The sequence listing is incorporated by reference as if fully recited herein.

BACKGROUND OF THE INVENTION

The described invention relates in general to chimeric antigenic immunoreceptors and more specifically to a programmable immunocyte receptor complex system that may be used with a target detector molecule that is specific to a target of interest for both diagnostic and therapeutic applications.

Chimeric antigen receptors (CARs, also referred to as chimeric immunoreceptors, chimeric T cell receptors, artificial T cell receptors, or CAR T) are engineered receptors that confer arbitrary specificity (e.g. of a monoclonal antibody) to an immune effector cell (i.e., a T cell). Such receptors are referred to as "chimeric" because these receptors include components derived from different sources. CAR T cells have become one of the most important tools in cancer therapeutics. In its basic form, CAR therapy adapts human immune cells to recognize and kill cells that are cancerous or that harbor dangerous pathogens in the body. This process is accomplished by genetic engineering to generate recombinant receptors on the surface of T lymphocytes and other immune cells, thereby redirecting their function and specificity. A CAR therapy for cancer, using a technique called adoptive cell transfer has been used to treat acute lymphoblastic leukemia. This therapy involves removing T cells from a patient and modifying those cells so that they express receptors specific to the patient's cancer. The modified T cells, which can effectively recognize and kill the cancer cells, are reintroduced into the patient. Adoptive transfer of T cells that express chimeric antigen receptors is very promising as an anti-cancer therapeutic because CAR-modified T cells can be engineered to target virtually any tumor associated antigen.

Engineering CAR T cells for cancer immunotherapy may include the use of viral vectors such as retrovirus, lentivirus or transposons, that integrate a transgene into the host cell genome. However, this approach has the potential to negatively affect the T cell's endogenous gene expression possibly resulting in genotoxicity, wherein the engineered cells become tumorigenic. Alternate approaches utilize non-integrating vectors such as plasmids or mRNA; however, these types of episomal DNA/RNA are typically lost upon repeated cell division and the engineered CAR T cells will likely lose their CAR expression after a relatively short period of time. Another approach involves the use of a vector that is stably maintained in the T cell, without being integrated in its genome. This method enables long-term transgene expression without the risk of insertional mutagenesis or genotoxicity, thereby providing a safer approach to producing CAR T cells for cancer immunotherapy.

Construction of CAR cells has overwhelmingly relied on T cells, although macrophages, dendritic cells and natural killer cells have been used. Most CAR T cells include an antibody single-chain variable fragment (scFv) on the surface for antigen-recognition, although different proteins can also be used. Inside the CAR T cells, these antigen-recognition domains are linked to the CD3ζ-chain for intracellular signaling. The CD3ζ ζ-chain is the primary transmitter of signals from endogenous T cell receptors (TCRs). Upon binding of a specific antigen by the surface receptor, the signaling domain activates cytokine release, target cell lysis and T-cell proliferation. Different design strategies have been used to improve the safety and antitumor efficacy of CAR T cells resulting in four generations of CAR design. First-generation CARs include a target detection domain and one signaling domain. Second-generation CARs include a target detection domain, a signaling domain and a co-stimulatory signaling domain (e.g., CD28, 41BB, ICOS). Preclinical studies indicated that the second generation improved the antitumor activity of T cells. Third-generation CARs include a target detection domain, a signaling domain and two co-stimulatory signaling domains (e.g., CD3z-CD28-41BB or CD3z-CD28-OX40). FIG. 1 provides an illustration of a standard third generation CAR showing only 6 ITAMs and a permanent, covalently attached scFv for targeting. During the evolution of this technology, the PI3K binding site used was identified in co-receptor CD28, while the ITAM motifs were identified as a target of the CD4- and CD8-p561ck complexes. Fourth-generation CARs differ greatly from the first three generation due to their cytokine release function.

The small molecule drug conjugates (SMDCs) platform in immuno-oncology involves the engineering of a single universal CAR T cell, which binds with extraordinarily high affinity to a benign molecule referred to as a FITC molecule. These cells are then used to treat various cancer types when co-administered with bispecific SMDC adaptor molecules. These unique bispecific adaptors are constructed with a FITC molecule and a tumor-homing molecule to precisely direct the universal CAR T cell to the cancer cells, which results in localized T cell activation. Anti-tumor activity is induced only when both the universal CAR T cells and the correct antigen-specific adaptor molecules are present. Anti-tumor activity and toxicity can be controlled by adjusting the administered adaptor molecule dosing. Treatment of antigenically heterogeneous tumors can be achieved by administration of a mixture of the desired antigen-specific adaptors. However, limitations and difficulties associated with this therapeutic methodology include: (i) the inability to control the rate of cytokine release and tumor lysis; and (ii) the absence of an "off switch" that can terminate cytotoxic activity when tumor eradication is complete.

Adverse events have occurred while using second and third generation CAR Ts. One patient died five days after cyclophosphamide chemotherapy followed by infusion of CAR Ts recognizing the antigen ERBB2 (HER-2/neu). The toxicity led to a clinically significant release of pro-inflammatory cytokines, pulmonary toxicity, multi-organ failure and eventual patient death. This "cytokine storm" (cytokine release syndrome) was thought to be due to CAR T cell cytotoxicity against normal lung epithelial cells, known to express low levels of ERBB2. This and other adverse events underscore the need for caution when utilizing CAR Ts, as unlike antibodies against tumor-associated antigens, these cells are not cleared from the body quickly. Long exposure to CAR Ts is necessary for good clinical outcome, but is not feasible due to adverse effects. The great promise of cancer immunotherapy is to clear the tumor without the toxicity of conventional treatments. The treatment of cancer with CAR Ts has several advantages: HLA-independent recognition of antigen, broad applicability for many patients and rapid delivery. Successful application of CAR Ts will require the identification of a tumor-associated antigen that is expressed only on tumor cells, thereby minimizing toxicity risk.

Despite great success, efforts to develop and improve the CAR T cell system have been hindered by multiple challenges: (i) The functionality of the system requires separate cell development paths for each target antigen because it lacks a platform for rapid adaptability of different detectors; (ii) the single antigen specificity of the CAR T cell system can be a problem in cases of tumor heterogeneity and when cancer cells stop expressing some of the CAR-targeted markers, thereby evading the immune response; (iii) unregulated persistence of CAR activity can cause cytokine release syndrome and other toxicities; (iv) the current system is heavily focused on using T cells, with a very small percentage of the field trying to use other cell types; (v) most CAR T cells are developed for cancer treatment with little or no attention paid to treatment of infectious diseases; (vi) CAR T cells can sometimes bind and react to weakly expressed off-tumor targets resulting in undesirable effects ("on-target off-tumor" reaction) and (vii) engineered cells can have low signaling capacity, reduced cell proliferation and persistence. Accordingly, there is an ongoing need for another generation of more predictable, effective and reliable CAR T cells or for a different system that overcomes the aforementioned deficiencies.

SUMMARY OF THE INVENTION

The following provides a summary of certain exemplary embodiments of the present invention. This summary is not an extensive overview and is not intended to identify key or critical aspects or elements of the present invention or to delineate its scope. However, it is to be understood that the use of indefinite articles in the language used to describe and claim the present invention is not intended in any way to limit the described system. Rather the use of "a" or "an" should be interpreted to mean "at least one" or "one or more".

In accordance with one aspect of the present invention, a programmable immunocyte receptor complex expressed by an immunocyte is provided. This programmable immunocyte receptor complex includes a plurality of native or endogenously expressed receptor subunits, wherein at least one of the plurality of native or endogenously expressed receptor subunits has been engineered or modified to include a biotin-binding component (or biotin analogue-binding component), and wherein the biotin-binding component is operative to bind to a target detector molecule that binds to or otherwise interacts with a predetermined target.

In accordance with another aspect of the present invention, a programmable immunocyte receptor complex cell system is provided. This programmable immunocyte receptor complex cell system includes an immunocyte; and a programmable receptor complex expressed by the immunocyte, wherein the programmable receptor complex includes a plurality of native or endogenously expressed receptor subunits, wherein at least one of the plurality of native or endogenously expressed receptor subunits has been engineered or modified to include a biotin-binding component (or biotin analogue-binding component), and wherein the biotin-binding component is operative to bind to a target detector molecule that binds to or otherwise interacts with a predetermined target.

In yet another aspect of this invention, a programmable immunocyte receptor complex cell system is provided. This programmable immunocyte receptor complex cell system includes an immunocyte; and a programmable receptor complex expressed by the immunocyte, wherein the programmable receptor complex includes a plurality of native or endogenously expressed receptor subunits, wherein at least one of the plurality of native or endogenously expressed receptor subunits has been engineered or modified to include an FcγRI receptor component, and wherein the FcγRI receptor component is operative to bind to a target detector molecule that binds to or otherwise interacts with a predetermined target.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein:

FIG. 101A is the unstained sample; FIG. 101B is the secondary Ab alone; and FIG. 101C is the primary Ab plus the secondary Ab;

FIGS. 106-107 are images of SDS-PAGE gel and Western-blot analysis of purified, biotinylated mouse mAb against *E. coli* O111 LPS (1F11) IgG2a; wherein FIG. 106 is a photograph of a 4-20% SDS-PAGE gel showing the protein standard in lane 1, the purified, non-biotinylated protein in lane 2 and the purified, biotinylated protein in lane 3; and wherein FIG. 107 is a photograph of a Western-blot analysis showing the protein standard in lane 1, the purified, non-biotinylated protein in lane 2 and the purified, biotinylated protein in lane 3;

FIGS. 114-116 are graphs showing the results of an activation marker expression assay (expression levels of CD69 on eMA-CD3ε cells upon activation using mouse Anti-*E. coli* O111 LPS and *E. coli* O111 LPS), wherein FIG. 114 shows the results for cells incubated with LPS only; FIG. 115 shows the results for cells incubated with antibody only; and FIG. 116 shows the results for cells incubated with antibody and LPS;

FIGS. 117-119 are graphs showing the results of an activation marker expression assay (expression levels of CD62L on eMA-CD3ε cells upon activation using mouse Anti-*E. coli* O111 LPS and *E. coli* O111 LPS), wherein FIG. 117 shows the results for cells incubated with LPS only; FIG. 118 shows the results for cells incubated with antibody only; and FIG. 119 shows the results for cells incubated with antibody and LPS.

DETAILED DESCRIPTION OF THE INVENTION

Figure 1:
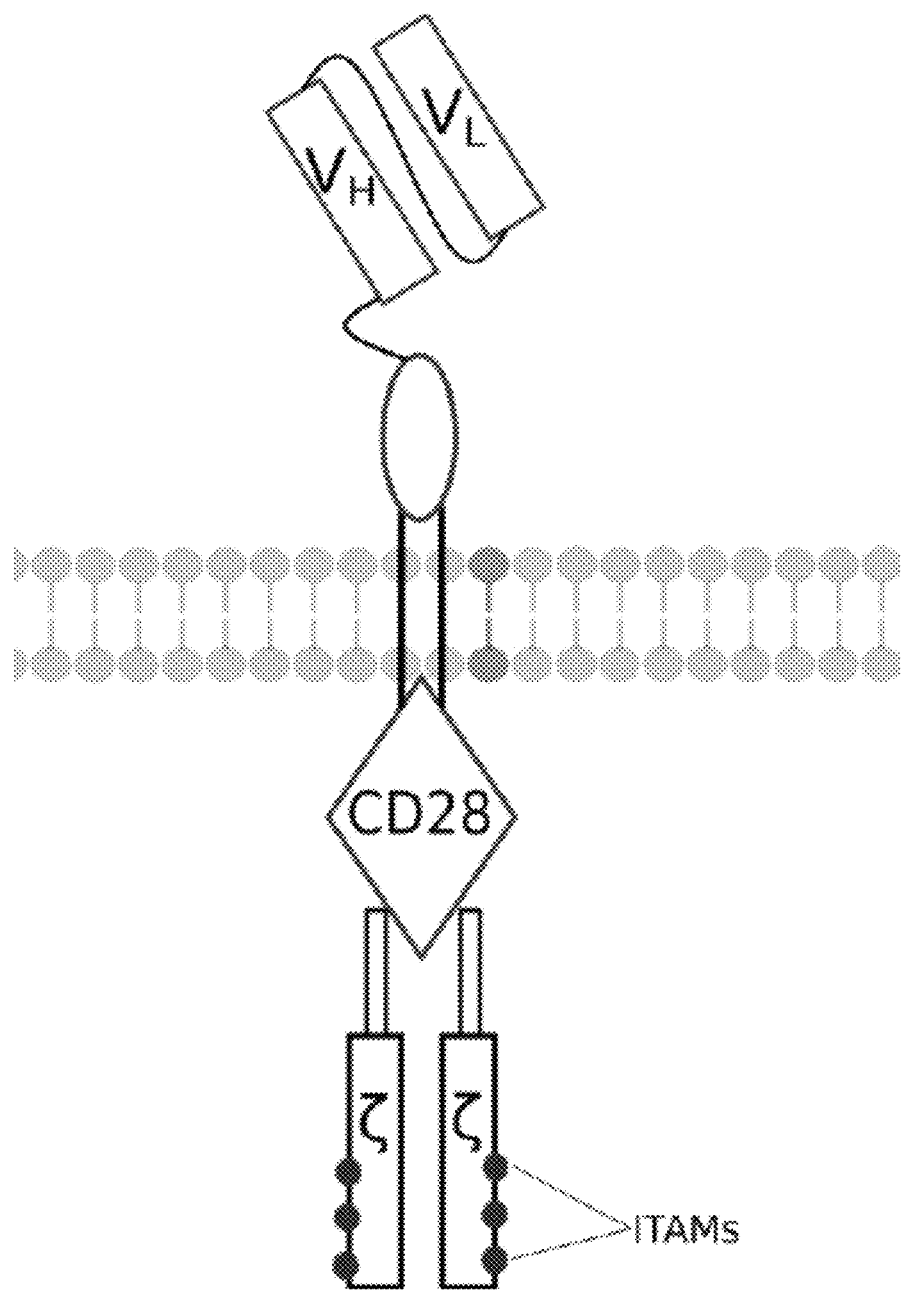
FIG. 1 is an illustration of a standard third generation (prior art) CAR showing six ITAMs and a permanent, covalently attached scFv for targeting.

Exemplary embodiments of the present invention are now described with reference to the Figures. Reference numerals are used throughout the detailed description to refer to the various elements and structures. Although the following detailed description contains many specifics for the purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

As previously discussed, chimeric antigen receptor T cells (CAR T cells) are very important in cancer therapeutics. CAR therapy involves adapting human immune cells to recognize and kill cells that are cancerous or harbor dangerous pathogens in the body. This process is accomplished through genetic engineering that generates recombinant receptors on the surface of T lymphocytes and other immune cells, thereby redirecting their function and specificity. Following this modification, cells are re-introduced into a patient to seek certain known "fixed targets". These cells are then able to identify and kill the "bad" cells in the body that carry these "fixed targets". However, current CAR T systems lack a platform for rapid adaptability of different detectors and requires separate cell development paths for each "fixed target". Additionally, CAR T cell activities cannot be modulated or turned off to stop adverse reactions such as those discussed above, once administered. Moreover, excessive engineering and highly invasive manipulations of the T cell diminish cellular signaling capacity, cell proliferation, survival and persistence. Accordingly, the programmable, universal, adaptable TCR complexes of the present invention are designed to overcome the deficiencies of existing CAR T systems by providing a novel cell system that includes a programmable immunocyte receptor complex.

EXAMPLE I mFcγRI-CD3ζ

Figure 2:
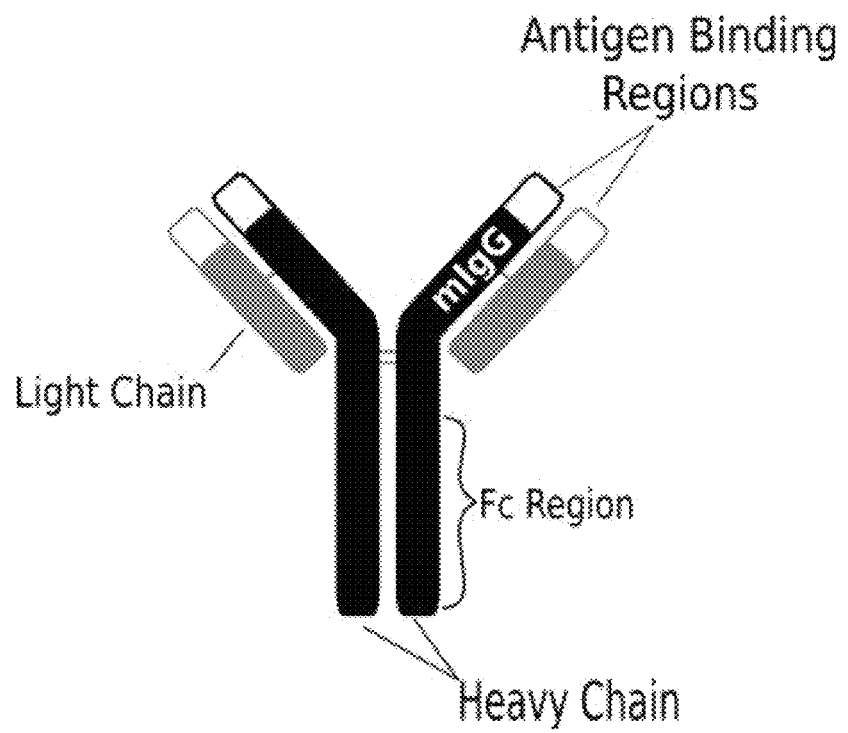
FIG. 2 is an illustration of a mouse IgG antibody showing the antigen binding regions.

A first exemplary embodiment of the present invention includes a programmable, universal, adaptable TCR complex system that includes modification of the TCR complex by fusing mouse FcγRI (mFcγRI) to CD3ζ of the human TCR complex to generate mFcγRI-CD3ζ. The expressed universal receptor (mFcγRI) can bind to the Fc region of some mouse immunoglobulins with a high affinity and redirect the adaptor TCR complex cells to target specific antigens. FIG. 2 is an illustration of a mIgG antibody showing the antigen binding regions. The FcγRI-CD3ζ gene was delivered into CD4+ T cells by electroporation and added as a random insert. FIGS. 6-27 are illustrations of exemplary embodiments of the mFcγRI variant of the engineered receptors of the present invention, based either on the endogenous αβ T cell receptor complex or the endogenous γδ T cell receptor complex. A variant of this embodiment is further described in U.S. Pat. Nos. 9,752,199; 9,850,546; 9,850,547; and 9,850,548, which are incorporated by reference herein, in their entirety, for all purposes.

EXAMPLE II mSA2-CD3ζ

Figure 3:
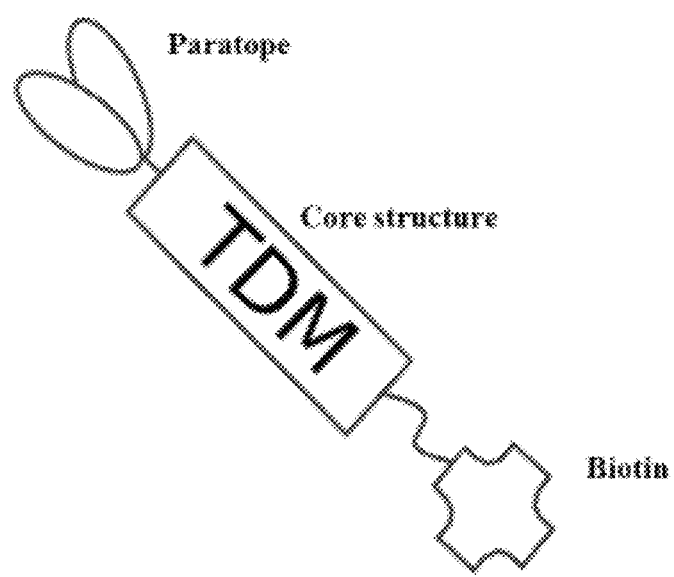
FIG. 3 is an illustration of an exemplary target detector molecule of the present invention showing the paratope for binding to target epitopes, the overall core structure for stability, and biotin, which binds to a portion of the engineered receptors of the present invention.
Figure 4:
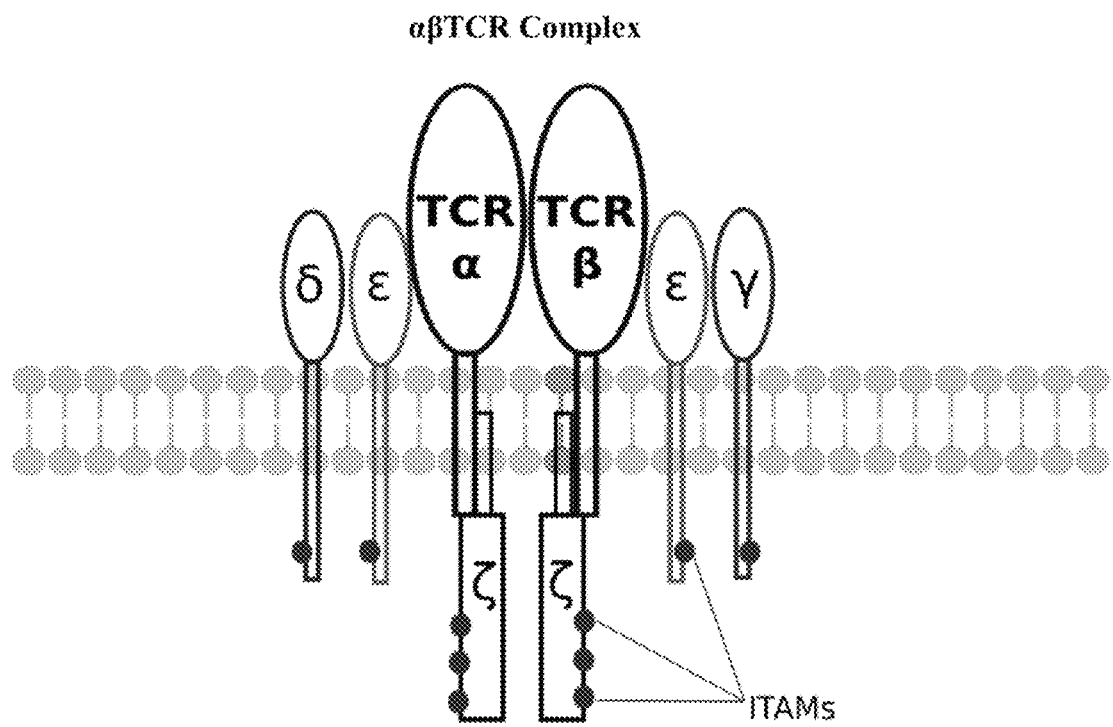
FIG. 4 is an illustration of an exemplary native or endogenously expressed αβ T cell receptor complex.
Figure 5:
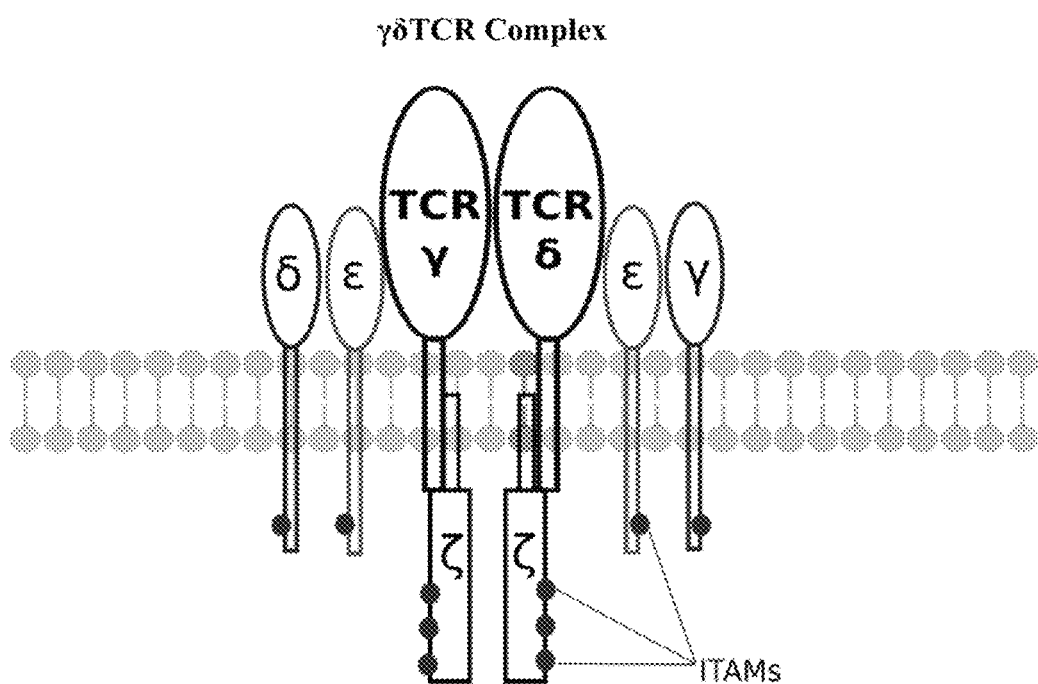
FIG. 5 is an illustration of an exemplary native or endogenously expressed γδ T cell receptor complex.

A second exemplary embodiment of this invention includes a programmable, universal, adaptable TCR complex system that was developed through modification of the TCR complex by fusing monomeric streptavidin 2 (mSA2) and the endogenous CD3ζ of the human TCR complex. The mSA2-CD3ζ gene was introduced into CD4+ T cells as a heterozygous insert by replacing the endogenous CD3ζ using CRISPR/Cas9 technology through electroporation. In this design, the surface-expressed universal receptors (mSA2) can bind to any biotinylated target detector molecule (TDM) and redirect the adaptor TCR complex cells to target specific antigens. FIG. 3 is an illustration of an exemplary target detector molecule showing the paratope (or other ligand) for binding to target epitopes, the overall core structure for stability and biotin, the binding site for attaching to the engineered receptor. This version of the adaptor TCR complex differs from a standard CAR T cell in the following ways: (i) the mSA2 receptor is universal (can bind to any biotinylated TDM) and (ii) the mSA2 receptor is directly attached to the TCR complex via CD3ζ in a way designed to harness the TCR complex for maximum signaling capacity because the engineered cell utilizes all 10 ITAMs of the complex. FIGS. 28-45 are illustrations of exemplary embodiments of the mSA2-CD3ζ variant of the engineered receptors of the present invention, based either on the endogenous αβ T cell receptor complex or the endogenous γδ T cell receptor complex. A variant of this embodiment is further described in U.S. Pat. Nos. 9,752,199; 9,850,546; 9,850,547; and 9,850,548, which are incorporated by reference herein, in their entirety, for all purposes.

EXAMPLE III eMA-CD3ε

Figure 46:
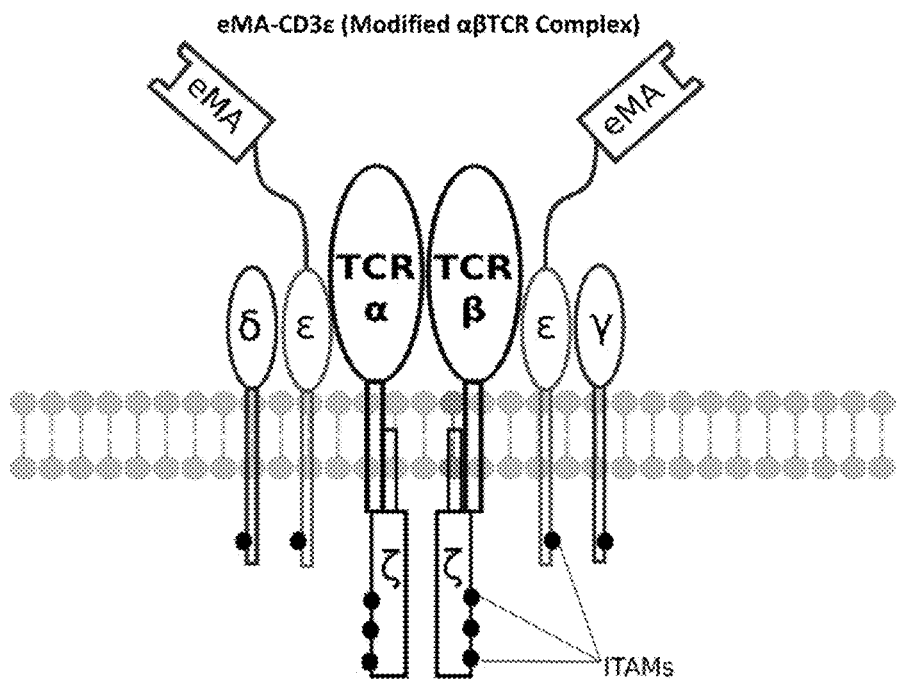
FIGS. 46-57 are illustrations of exemplary embodiments of the eMA variant of the engineered receptors of the present invention, based either on the endogenous αβ T cell receptor complex or the endogenous γδ T cell receptor complex.
Figure 47:
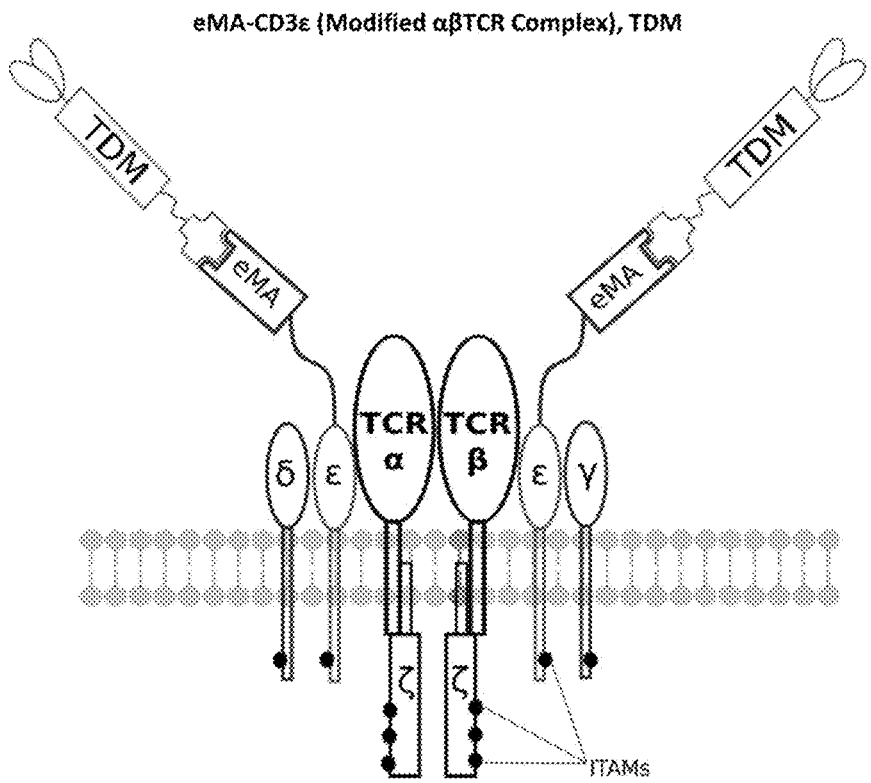
Figure 48:
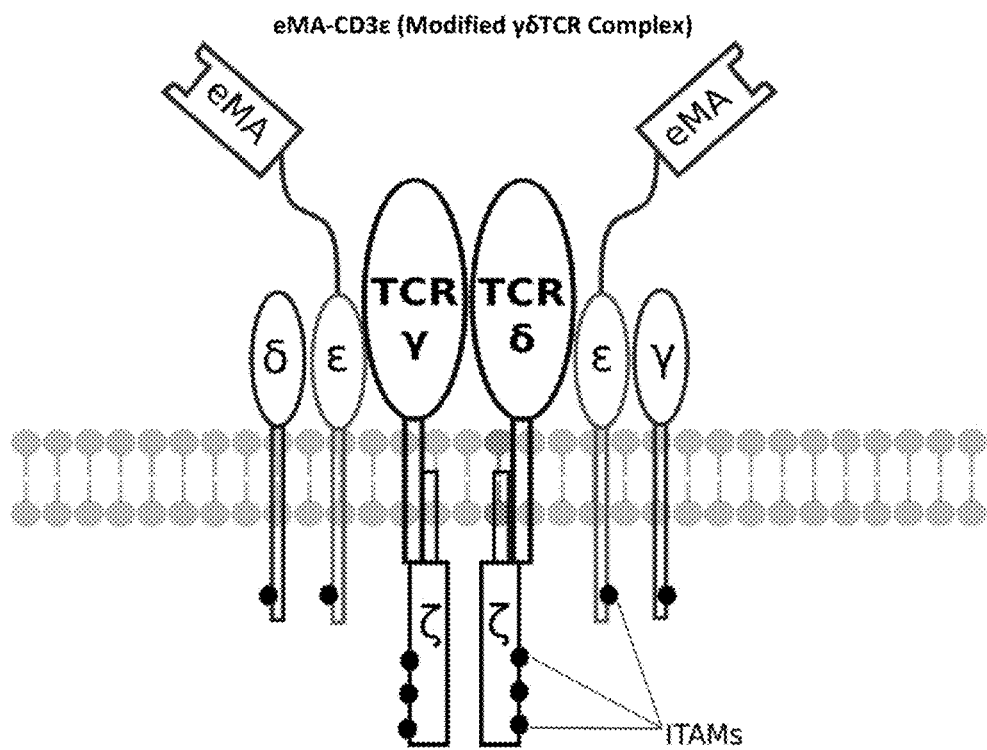
Figure 49:
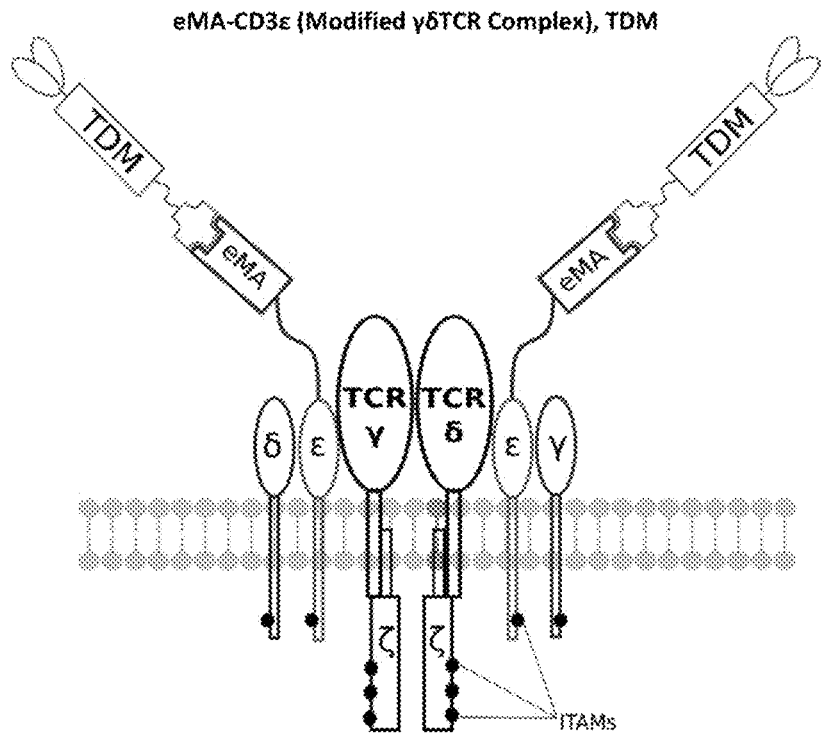
Figure 50:
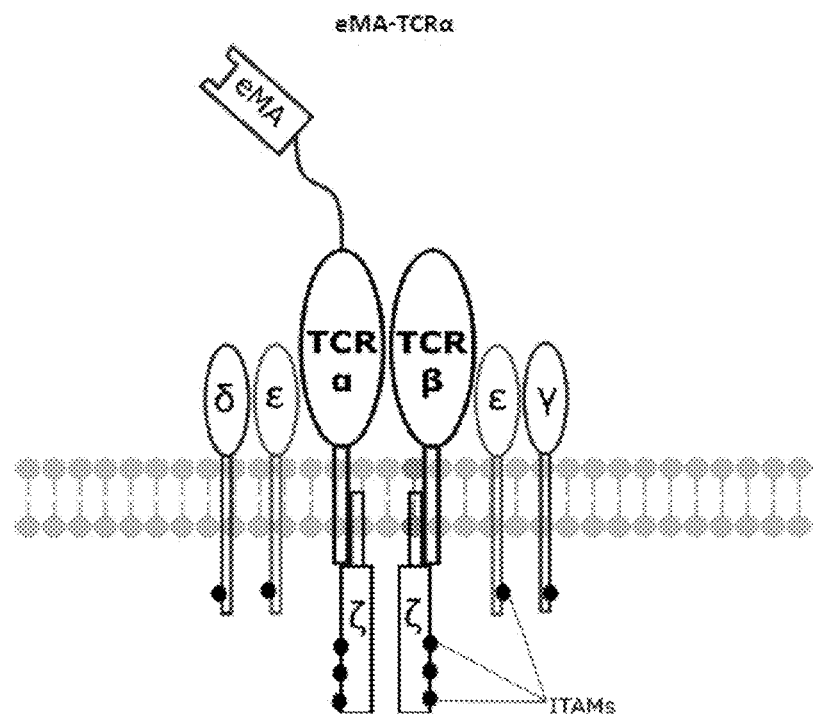
Figure 51:
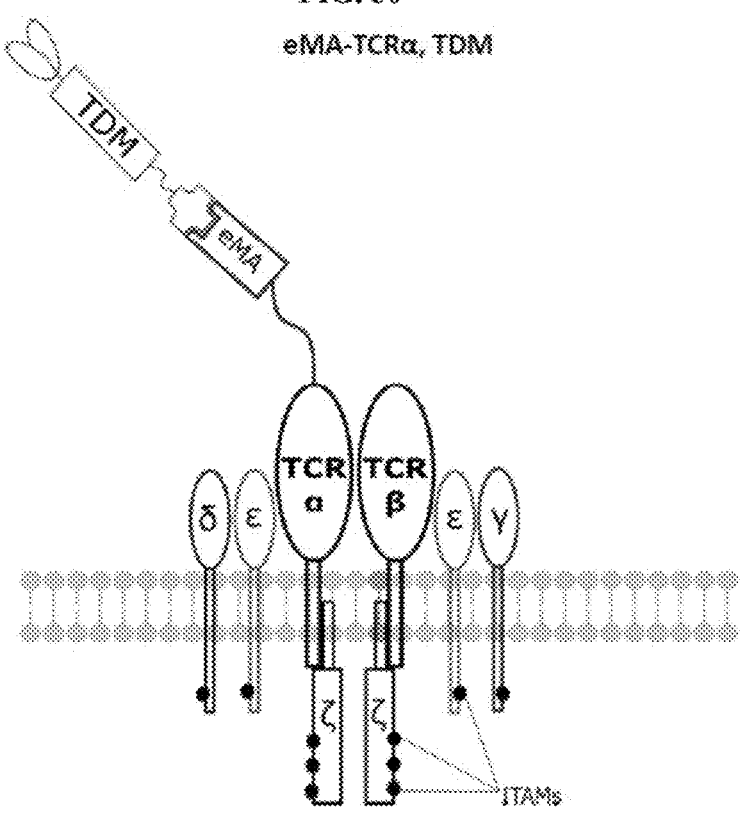
Figure 66:
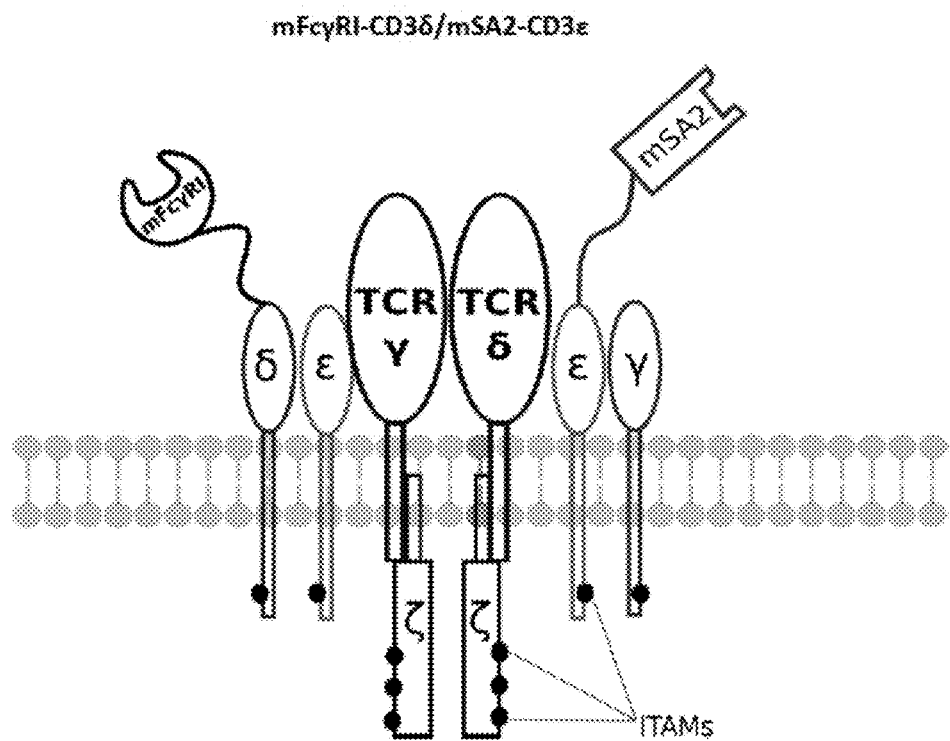
Figure 67:
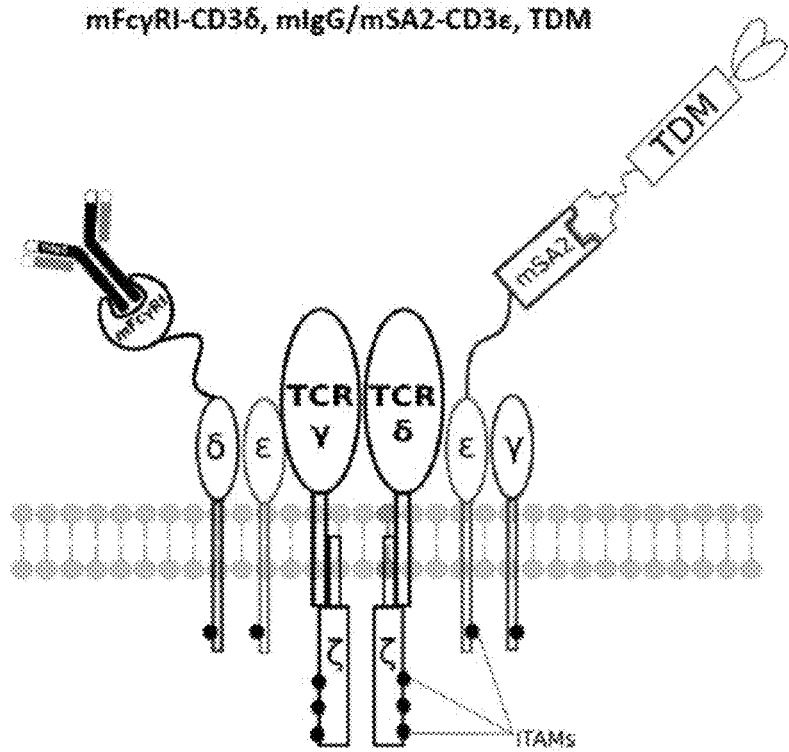
Figure 68:
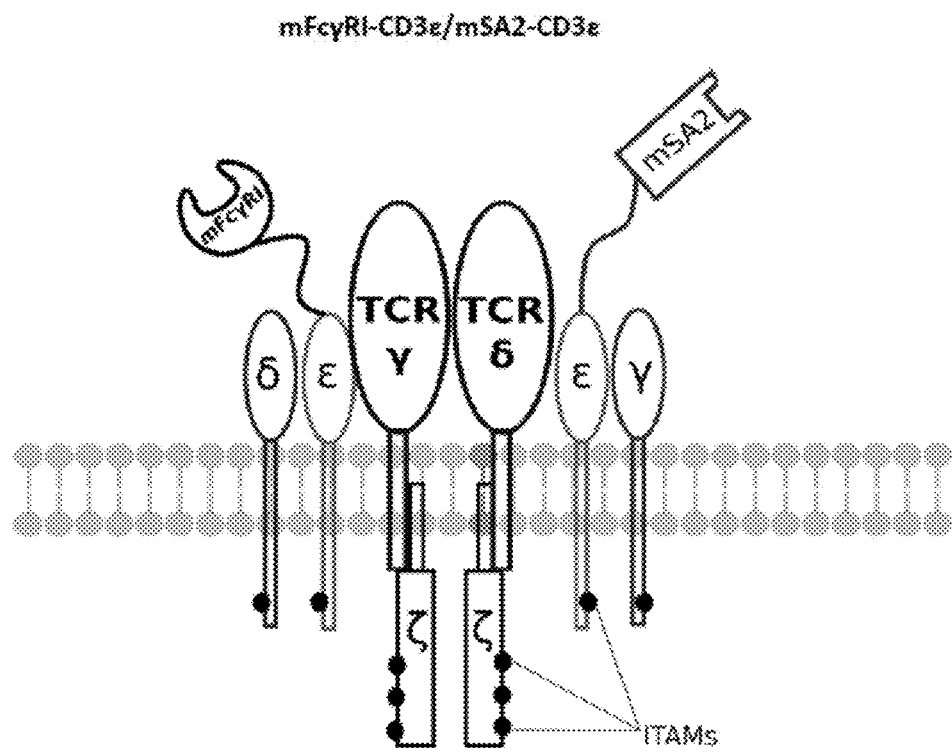
Figure 69:
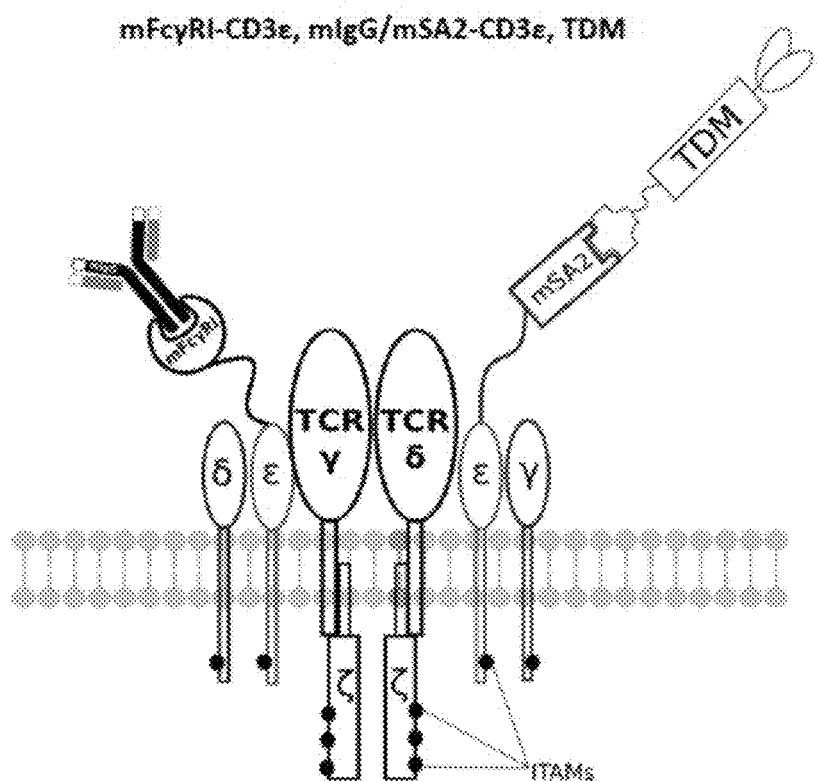
Figure 70:
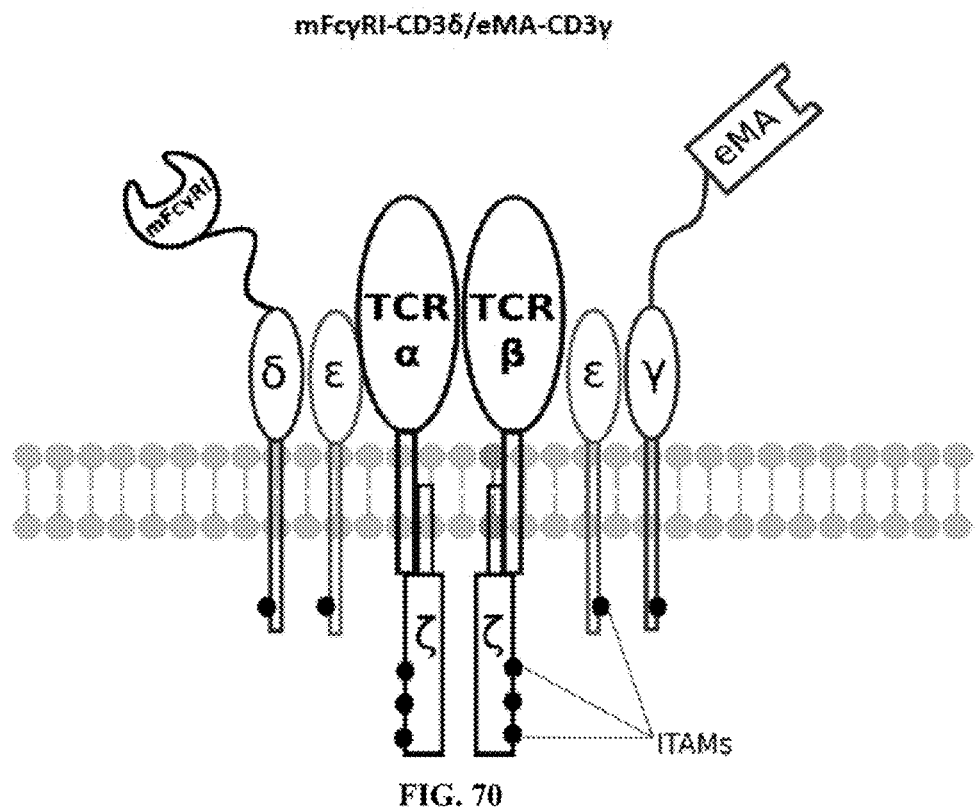
FIGS. 70-89 are illustrations of exemplary embodiments of the FcγRI/eMA combination variant of the present invention, based either on the endogenous αβ T cell receptor complex or the endogenous γδ T cell receptor complex.
Figure 71:
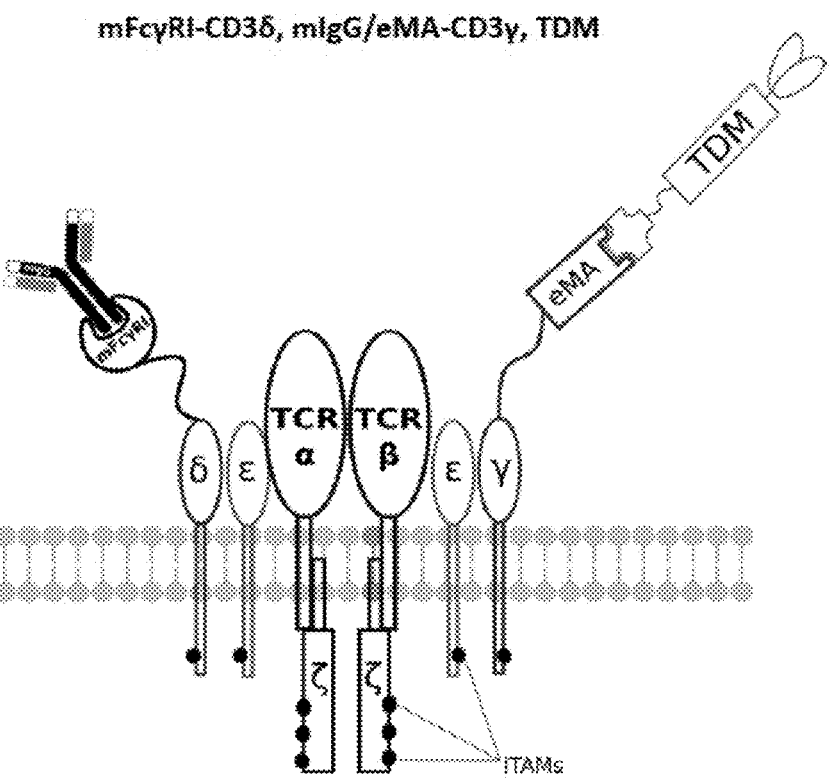
Figure 72:
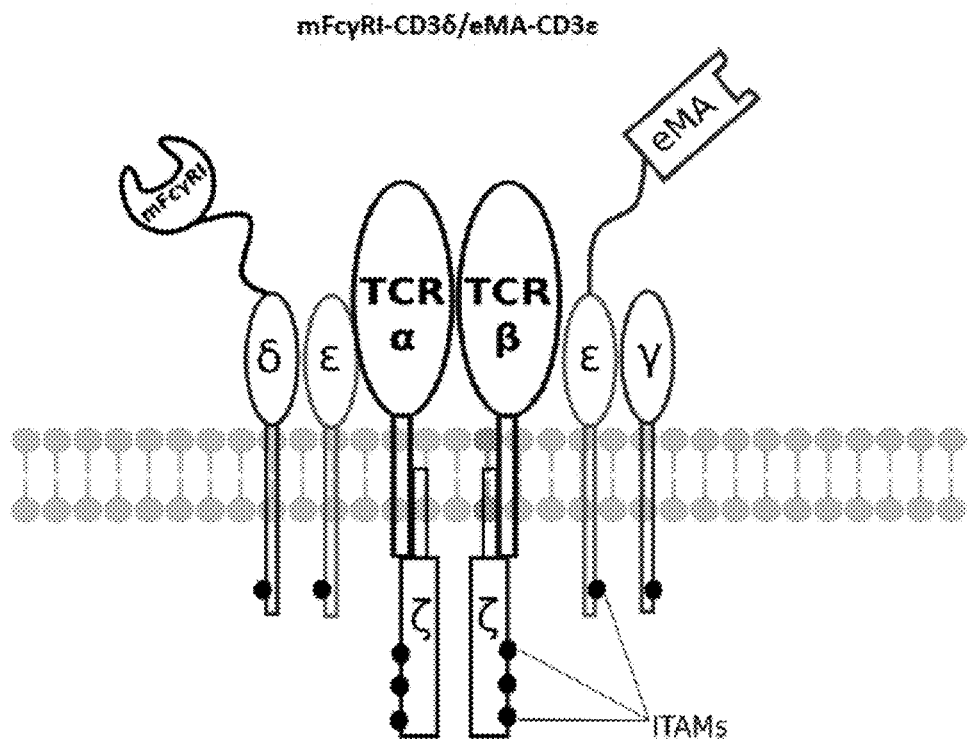
Figure 73:
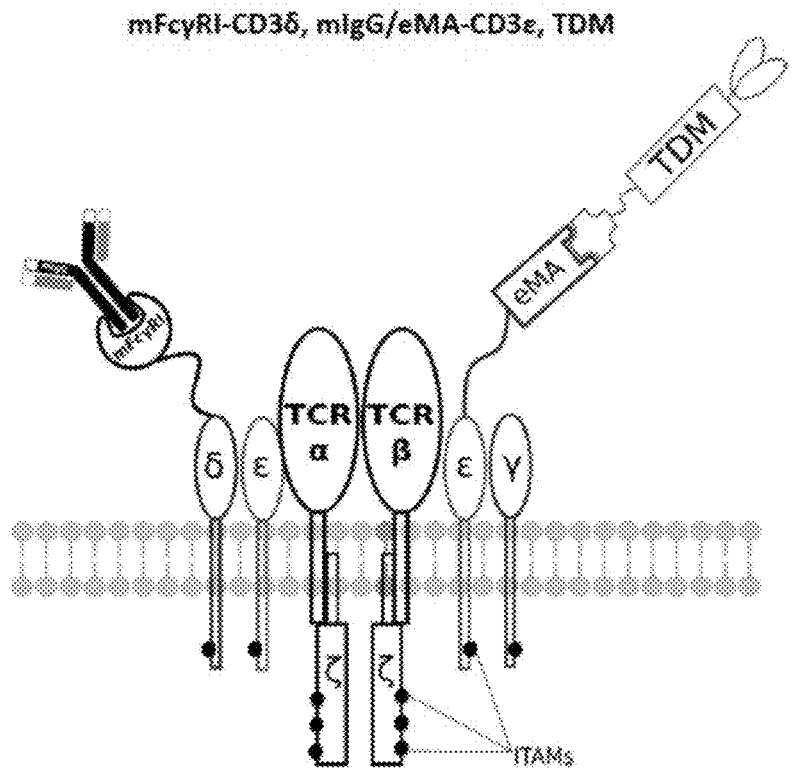
Figure 75:
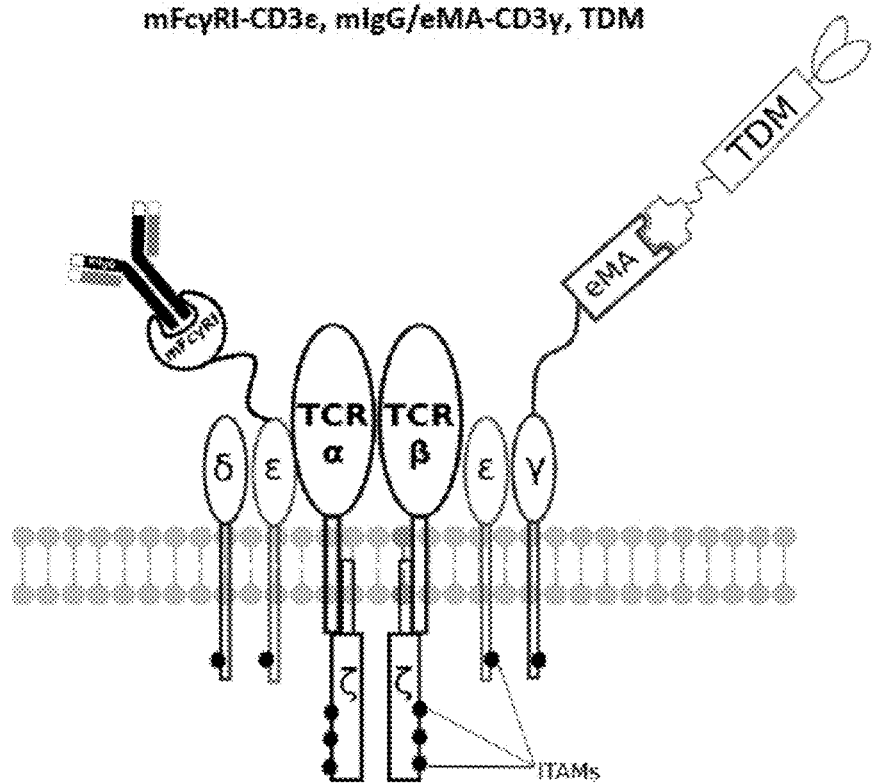
Figure 76:
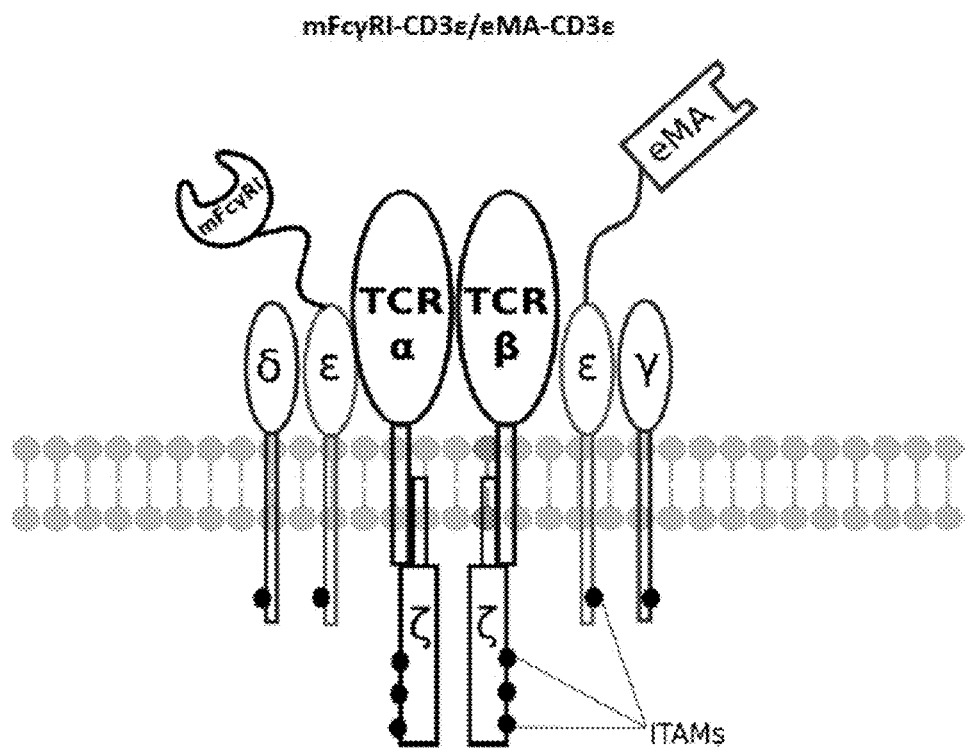

A third exemplary embodiment of this invention includes a programmable, universal, adaptable TCR complex system that was developed through modification of the TCR complex by fusing enhanced monoavidin (eMA) and the endogenous CD3ε of the human T cell receptor complex to form eMA-CD3ε (see FIGS. 46 and 48, which illustrates the design of the eMA-CD3ε adaptor TCR complex expression construct showing all 10 retained ITAMs). The universal receptor eMA can bind to any biotin-conjugated TDM with very high affinity, thereby enabling the modified T cells to target any antigen whose biotinylated TDM is loaded. In this embodiment, CD4+ T cells have been genetically engineered to express eMA-CD3ε on the cell surface. Following activation, the engineered CD4+ T cells recruit other immune cells to go after different cancer targets or pathogens. The eMA-CD3ε gene was introduced into T cells as a homozygous insert by replacing the endogenous CD3ε using CRISPR/Cas9 technology and by design, both CD3εs of the T cell receptor complex are utilized (see FIGS. 46 and 48). The gene construct was delivered by electroporation. This engineered cell is different from a standard CAR T cell in three fundamental ways: (i) the eMA receptor is universal (can bind to any biotinylated TDM); (ii) the eMA receptor is directly attached to the TCR complex through the endogenous CD3ε in a way that is designed to harness the TCR complex for maximum signaling capacity because the engineered cell utilizes all 10 ITAMs of the complex; and (iii) by linking eMA to the endogenous CD3ε of the TCR complex, two universal receptors are created for every TCR complex. FIGS. 46-57 are illustrations of exemplary embodiments of the eMA-CD3ε variant of the engineered receptors of the present invention, based either on the endogenous αβ T cell receptor complex or the endogenous γδ T cell receptor complex;

The eMA-CD3ε embodiment is non-invasive, does not interfere with the TCR complex and utilizes all 10 ITAMs of the TCR complex, thereby resulting in maximum signaling. In a set of in vitro experiments, biotinylated TDMs and specific targets were used to activate the adaptor TCR complex cells (see FIG. 102). Experimentation demonstrated that activation of all three exemplary embodiments resulted in cytokine production (see FIGS. 75-76). Furthermore, biotin competition and inhibition assays demonstrated that activities of cells modified in accordance with this invention can be modulated (see FIGS. 66-68).

Figure 65:
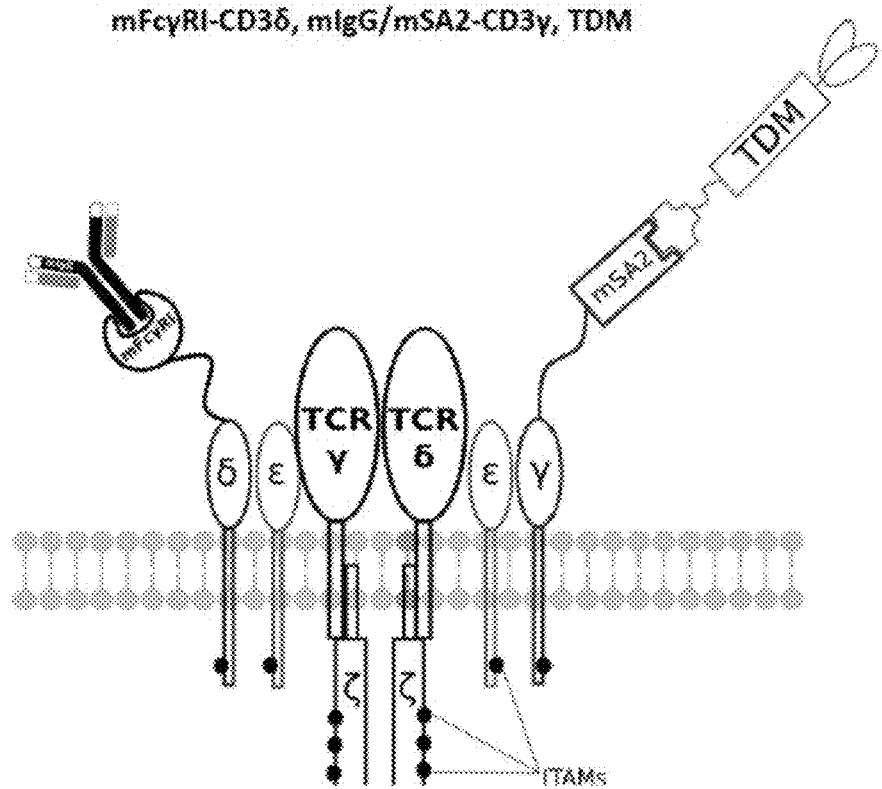

Regarding the third embodiment, the universal receptor (eMA) can bind to any biotin-conjugated programming TDM, thereby enabling the modified T cells to target any antigen or cancer cell when the specific/right biotinylated TDM is bound on the cell surface. FIG. 47 illustrates a fully loaded eMA-CD3ε interacting with the target detector molecule, wherein there are two universal receptors for every TCR complex and all 10 ITAMs of the TCR complex are retained. As a safety measure, after administration of these engineered cells in the body, biotin can be used as an inhibitor/competitor, to modulate cell activities in cases of adverse reactions. Compared to a standard CAR T cell, this design is non-invasive and enables the modified T cells to function naturally at their maximum signaling capacity resulting in improved cell proliferation, survival and persistence. In developing the eMA-CD3ε embodiment, T cells expressing eMA-CD3ε were activated using a biotinylated mAb against *E. coli* O111 and *E. coli* O111 bacteria as a target antigen. Furthermore, as discussed below, biotin was used in a competition and inhibition study to modulate cell activation. T cells that include the programmable immunocyte receptor complex of the present invention can be used in therapeutics as a safer and adaptable treatment for cancer, and as a pathogen detector in diagnostics. Cell activation and cytokine release assays performed on the modified T cells (see FIGS. 65 and 75-76) successfully demonstrated the functionality and performance of the cells.

The programmable immunocyte receptor complex of the present invention effectively addresses many challenges affecting current CAR T cell systems and provides significant improvements over existing systems and methods. The advantages and improvements over existing CAR T cell systems include the following: (i) separate cell development paths for each "fixed target" are not required; (ii) multiplexing blends of different targets can be applied; (iii) the "on-target off-tumor" problems associated with existing CAR T cells can be avoided by using programmable immunocyte receptor complex cells and TDMs with higher specificity for tumor antigens; (iv) the described programmable immunocyte receptor complex cells have been designed for use in companion diagnostics because they can be used for antigen detection in any given sample and at the same time administered as treatment to target the detected pathogen/biomarker in the body; (v) the described programmable immunocyte receptor complex cell system can be used as a universal/programmable configuration for addressing a variety of cancers, infectious diseases (e.g. TB and HIV) and other patient specific needs; (vi) this invention offers safer deployment as the system activity can be modulated or turned off (using biotin) after administration with the ability to stop adverse reactions; (vii) as an additional safety measure, the activity of the described system can be regulated in a dose-dependent administration of the biotinylated TDM; (viii) the versatility and improved safety of the described system allows for better outcomes and better prospects for accelerated clinical testing and ability to aggressively go after a wider range of targets; (ix) due to the safety features in the design, faster validation of biological targets in humans can be achieved without going through lengthy (and often misleading) animal studies; (x) re-usable components of the described system can enable new configurations to be brought to market by changing the targeting antibodies while keeping the underlying universal technology; (xi) the universal, adaptor receptor system of this invention is easily adaptable to different immune cell types e.g. CD4+ T cells, CD8+ T cells, γδ T cells, macrophages, B cells, NK cells and dendritic cells; and (xii) the described system is substantially "non-invasive" in T cells (i.e., minimal addition to the T cell).

Construction of the Programmable Immunocyte Receptor Complex

Jurkat Clone E6-1 cells [Cat. ATCC TIB152] were purchased from ATCC. The following cell lines and reagents were ordered from ThermoFisher Scientific (Waltham, MA): FreeStyle™ HEK 293-F cells [Cat. R79007]; FreeStyle™ 293 Expression Medium [Cat. 12338001]; OptiPRO™ SFM medium [Cat. 12309019]; FreeStyle™ MAX Reagent [Cat. 16447750]; biotinylated mouse anti-goat IgG [Cat. 31730]; Pierce™ protein G plus agarose; Sodium periodate; Hydrazide-PEG4-Biotin; BCA protein assay kit; and Pierce biotin quantitation kit. All restriction enzymes were obtained from New England Biolabs. The goat anti-mouse IgG Alexa-Flour647 [Cat. 115-605-062] was purchased from Jackson ImmunoResearch. The Coelenterazine-h [Cat. S20011] and the Wizard® SV Gel and PCR Clean-up Kit [Cat. A9281] were ordered from Promega. The QiaFilter Plasmid Midi and Maxi Kit [Cat. 12243] and the DNeasy® Blood & Tissue Kit [Cat #69504] were purchased from Qiagen. The Amaxa® Cell Line Nucleofector® Kit V [Cat #VCA-1003] was sourced from Lonza. The Pluronic-F68 [Cat #A1288] was obtained from Applichem and the BirA-500 kit was purchased from Avidity, Aurora, CO Biotinylated 1F11 scFv antibodies were extracted by BugBuster Master Mix from MilliporeSigma, Burlington, MA and purified using streptavidin mutein matrix from Sigma-Aldrich, St. Louis, MO Streptavidin [Cat. 85878] and *E. coli* O111 LPS [Cat: L3024-5MG] were also sourced from Sigma while *E. coli* O157 LPS was purchased from List Biological Laboratories [Cat: 206]. HRP conjugated anti-biotin antibody was purchased from Abcam (Cambridge, MA). MERS-CoV spike protein and SARS-CoV spike protein were purchased from Sino Biological (Beijing, China) while RPMI 1640 was purchased from Gibco (Cat: A1049-01). In some embodiments, chicken avidin may be used.

Genes were designed and constructed to generate universal adaptor TCR complex cells from T cells. A luminescent reporter enzyme Aequorin, and three different universal (programmable) receptors: mouse FcγRI-CD3ζ; mSA2-CD3ζ; and eMA-CD3ε, were constructed using different vectors as described below. The receptor constructs were used in transfection of Jurkat cells resulting in receptor expression. The Aequorin gene construct was also used to transfect Jurkat cells as a reporter gene for detecting cell activation. Two constructs, eMA-CD3ε and mSA2-CD3ζ, were inserted through CRISPR/Cas9 technology while mFcγRI-CD3ζ and Aequorin were introduced through random insertion. All the constructs were delivered by electroporation.

Figure 90A:
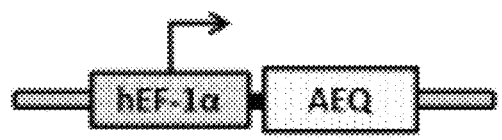
FIG. 90A is an illustration of a gene construct for the luminescent reporter enzyme aequorin, in accordance with an exemplary embodiment of the present invention.
Figure 90B:
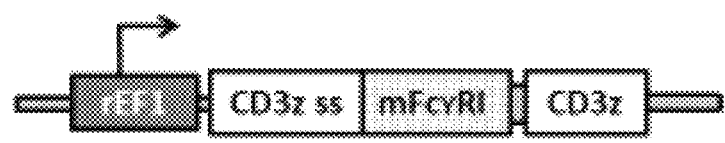
FIG. 90B is an illustration of a gene construct for the universal or programmable TCR complex mFcγRI-CD3ζ, in accordance with an exemplary embodiment of the present invention.
Figure 90C:
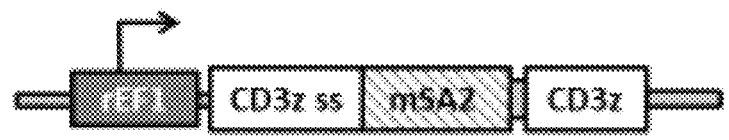
FIG. 90C is an illustration of a gene construct for the universal or programmable TCR complex mSA2-CD3ζ in accordance with another exemplary embodiment of the present invention.
Figure 90D:
FIG. 90D is an illustration of a gene construct for the universal or programmable TCR complex eMA-CD3ε, in accordance with still another exemplary embodiment of the present invention.

FIG. 90A is an illustration of a gene construct for the luminescent reporter enzyme aequorin; FIG. 90B is an illustration of a gene construct for the universal or programmable TCR complex mFcγRI-CD3ζ; FIG. 90C is an illustration of a gene construct for the universal or programmable TCR complex mSA2-CD3ζ; and FIG. 90D is an illustration of a gene construct for the universal or programmable TCR complex eMA-CD3ε.

Figure 91:
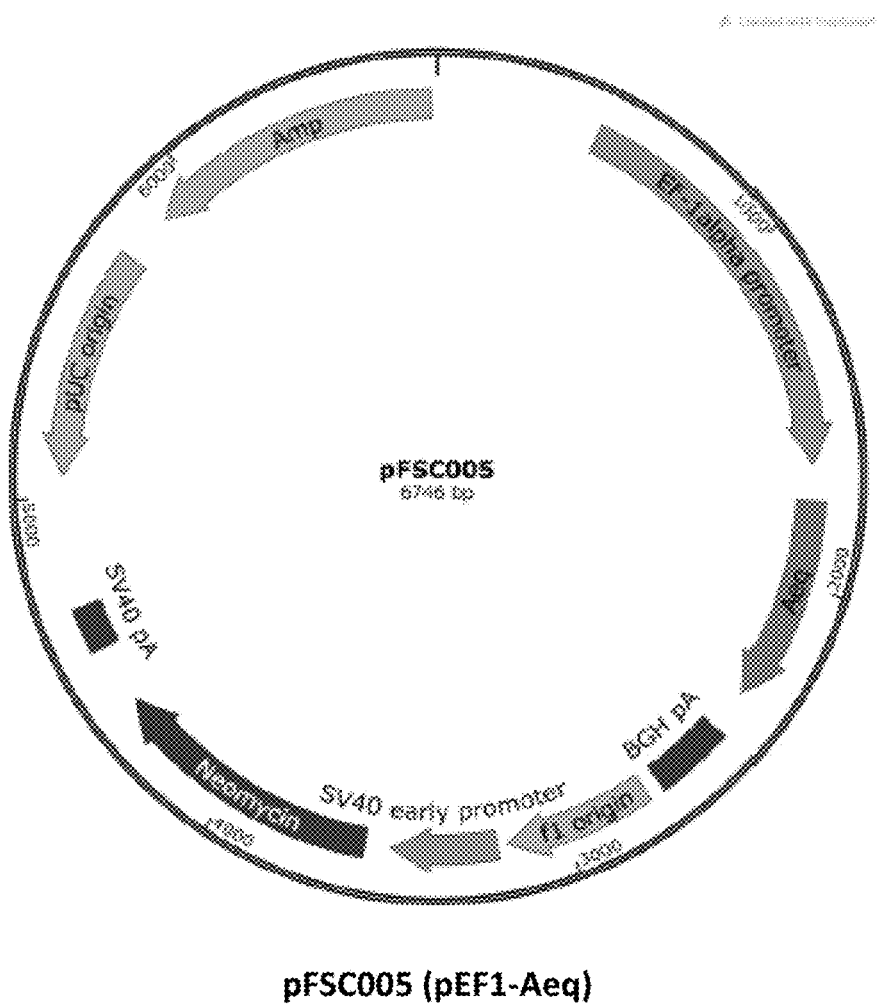
FIG. 91 is an illustration of plasmid pFSC005 (pEF1-Aeq)

FIG. 91 illustrates plasmid pFSC005 (pEF1-Aeq), which is the Aeq expression vector. The Aeq DNA sequence ordered from DNA2.0 was cloned into an Invitrogen pEF1/myc-His B vector. SEQ ID NO: 1 provides the DNA sequence for AEQ and SEQ ID NO: 2 provides the amino acid sequence for AEQ.

Plasmid pFSC005 includes the following components. A first component is the EF-1α promoter, which is the human elongation factor 1α-subunit (hEF-1α) promoter for high-level expression across a broad range of species and cell types. A second component is AEQ, which is the aequorin gene. The aequorin gene encodes a jellyfish (*Aequorea victoria*) calcium activatable photoprotein and was codon optimized and synthesized by DNA2.0. Active aequorin enzyme is formed by a complex between apoaequorin (APO), oxygen, and externally infused coelenterazine. When apoaequorin binds intracellular calcium released from the endoplasmic reticulum, the enzyme is activated and coelenterazine is oxidized, emitting light and releasing free apoaequorin and coelenterazine.

Construction of mFcγRI-CD3ζ

Figure 92:
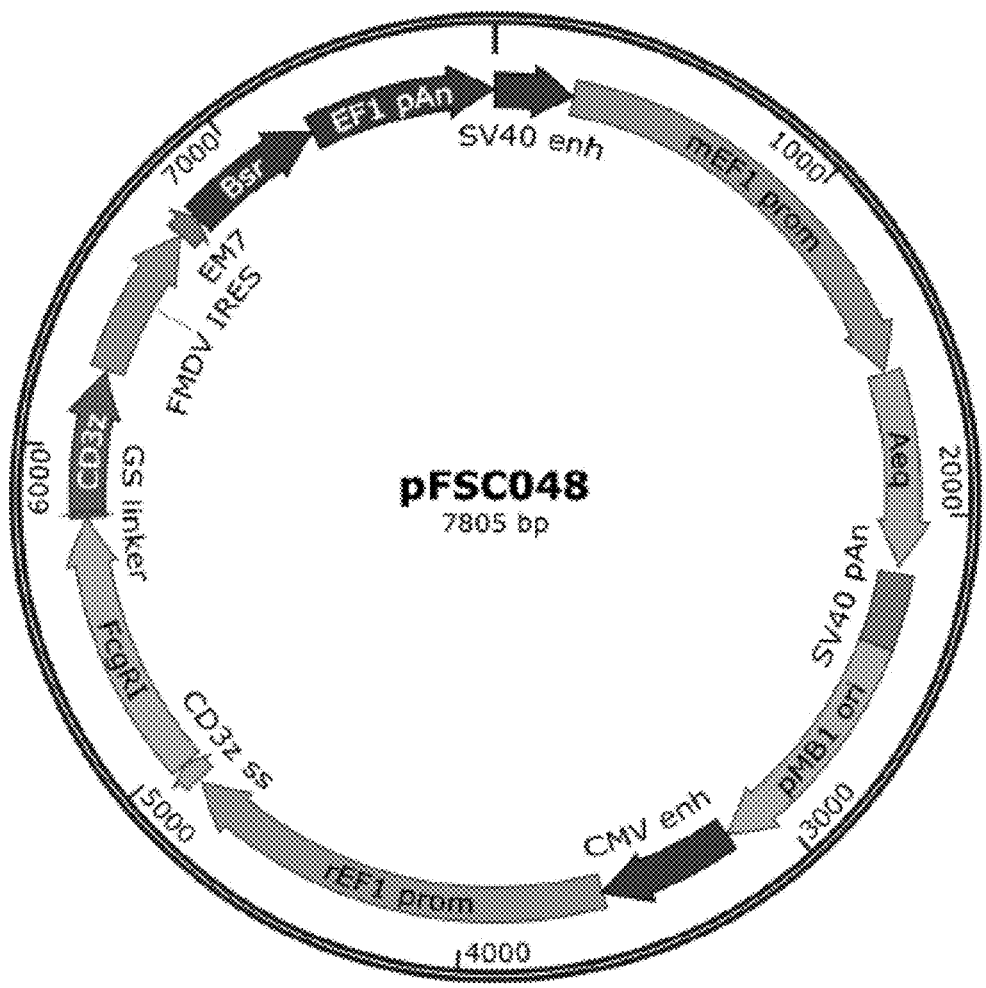
FIG. 92 is an illustration of plasmid pFSC048 (pVitro-blasti-Aeq-FcγRI-CD3ζ) (FcγRI-CD3ζ)

FIG. 92 illustrates plasmid pFSC048 (pVitro-blasti-Aeq-FcγRI-CD3ζ) (mFcγRI-CD3ζ), which is the mFcγRI-CD3ζ fusion protein expression vector. The T-cell CD3ζ subunit was genetically engineered to be expressed as a fusion protein where the extracellular domain of CD3ζ was fused with mouse FcγRI. The surface-expressed mFcγRI is specific for binding to the Fc region of mouse IgG2a. A short GS linker was genetically introduced to separate the antibody binding domain mFcγRI from the signal-transducing protein element CD3ζ. The CD3ζ signal peptide sequence was used for mFcγRI-linker-CD3ζ fusion protein T-cell surface expression. SEQ ID NO. 3 provides the DNA sequence for CD3ζSS-FcγRI-CD3ζ and SEQ ID NO. 4 provides the amino acid sequence for CD3ζSS-FcγRI-CD3ζ.

Plasmid pFSC048 includes the following components. A first component is CD3ζ SP, which is the CD3ζ signal peptide sequence. The DNA sequence was synthesized by DNA2.0. The CD3ζ signal peptide is used for eMA-linker-CD3ε fusion protein T-cell surface expression. A second component CD3ζ, which is the T-cell CD3 zeta subunit coding sequence. CD3ζ cDNA was purchased from MyBioSource.com (CAT #: MBS1278153). A third component is mFcγRI (FcgammaRI), which is a mouse T-cell surface FcγRI receptor. The DNA was ordered from GeneCopoeia, Inc (CAT #: EX-Mm02462-M02). A fourth component is the rEF1 promoter which is derived from the InvivoGen pVITRO1-blasti-mcs vector and is of rat origin. Like its human counterpart, this promoter displays a strong activity that yields similar levels of expression. EF-1α promoters are expressed at high levels in all cell cycles and lower levels during G0 phase. EF-1α promoters are also non-tissue specific and are highly expressed in all cell types. A fifth component is the CMV enhancer, which is the major immediate early enhancer of the human cytomegalovirus (HCMV), which is located between nucleotides −118 and −524, and is composed of unique and repeated sequence motifs. The HCMV enhancer can substitute for the 72-bp repeats of SV40 and is several folds more active than the SV40 enhancer. A sixth component is FMDV IRES, which is the internal ribosome entry site of the Foot and Mouth Disease Virus and which enables the translation of two open reading frames from one mRNA with high levels of expression. A seventh component is EM7, which is a bacterial promoter that enables the constitutive expression of the antibiotic resistance gene in *E. coli*. An eighth component is Blasti, wherein resistance to Blasticidin S is conferred by the bsr gene from *Bacillus cereus*. In bacteria, bsr is expressed from the constitutive *E. coli* EM7 promoter. In mammalian cells, bsr is transcribed from the rat EF-1α promoter as a polycistronic mRNA and translated by way of the FMDV IRES. A ninth component is EF1 pAn, which is a strong polyadenylation signal. InvivoGen uses a sequence starting after the stop codon of the EF1 cDNA and finishing after a bent structure rich in GT.

Construction of mSA2-CD3ζ

Figure 93:
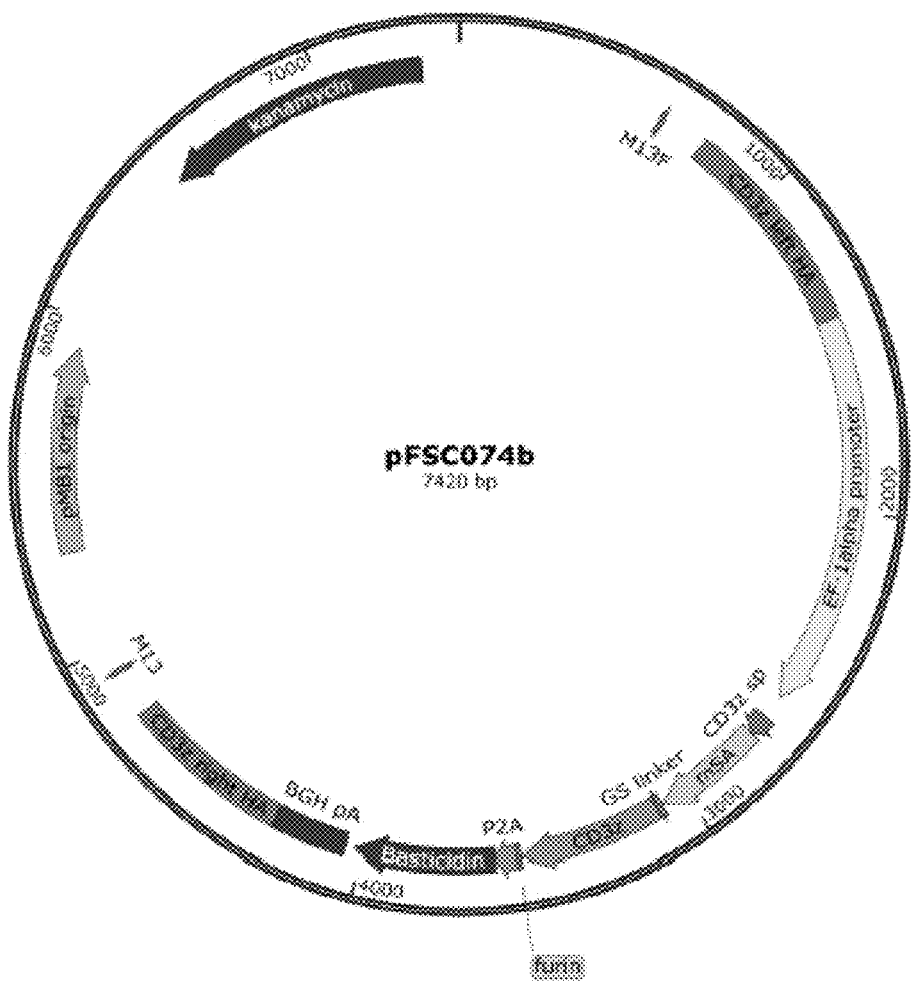
FIG. 93 is an illustration of plasmid pFSC074b (pUC-Kan-mSA2-CD3ζ-2A-Blasti) (mSA2-CD3ζ)
Figure 94:
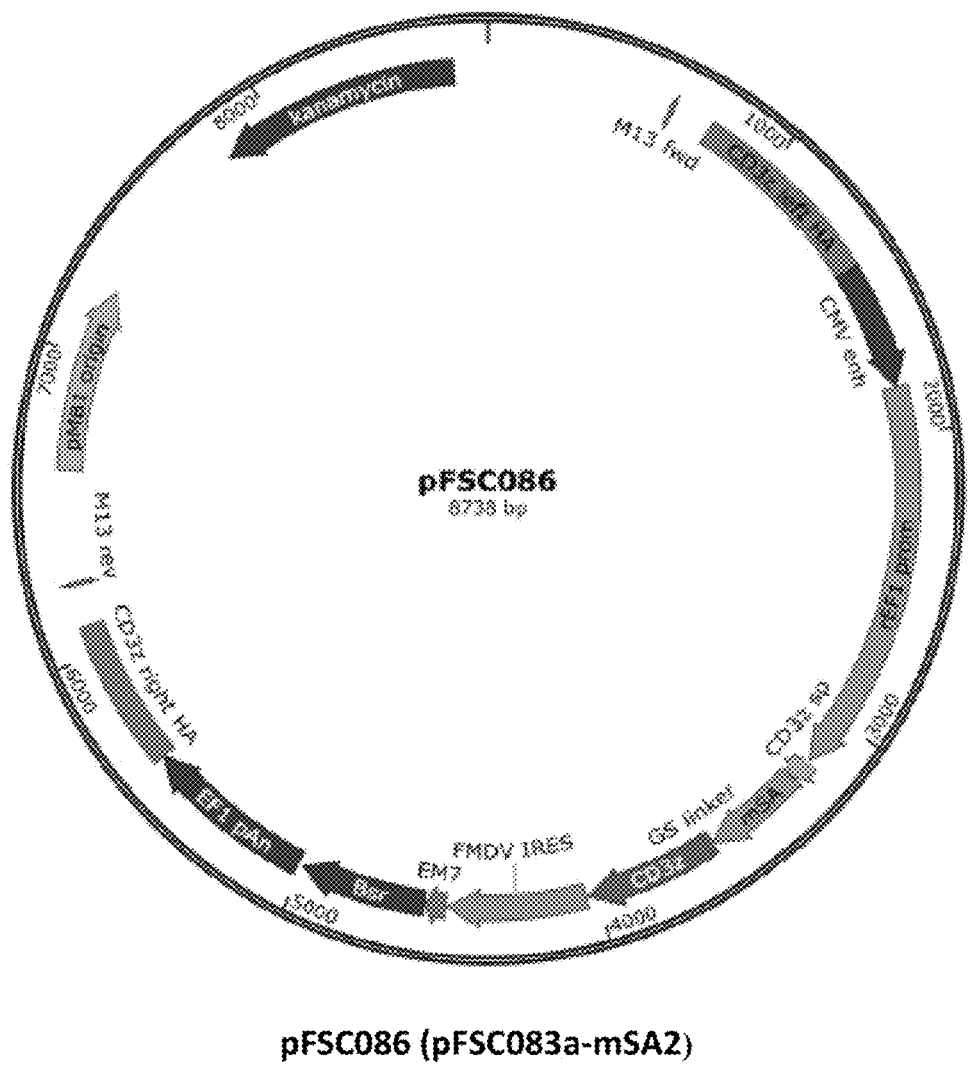
FIG. 94 is an illustration of plasmid pFSC086 (pUC-Kan-mSA2-CD3ζ-IRES-Blasti)

FIGS. 93-94 illustrate plasmids pFSC074b (pUC-Kan-mSA2-CD3ζ-2A-Blasti) (mSA2-CD3ζ) and pFSC086 (pUC-Kan-mSA2-CD3ζ-IRES-Blasti), which are the CD3ζ locus knock in donor plasmids. These plasmids contain CD3ζ homology arms flanking the T-cell CD3ζ subunit gene, which was genetically fused with biotin binding protein mSA2 (Monomeric Streptavidin 2) on N-terminus of CD3ζ through a GS linker. The mSA2-linker-CD3ζ cassette is driven by a human EF1α promoter in pFSC074b, and a rat EF1α promoter was used in pFSC086 to drive the transcription of mSA2-linker-CD3ζ. A signal peptide from CD3ζ was used for mSA2-linker-CD3ε fusion protein T-cell surface expression and a blasticidin gene was used as a selection marker. A furin-P2A peptide sequence was used in pFSC074b to co-express blasticidin with mSA2-linker-CD3ζ, while IRES was used in pFSC086 to co-express blasticidin with mSA2-linker-CD3ζ. SEQ. ID NO. 5 provides the DNA sequence for CD3ζSS-mSA2-CD3ζ and SEQ ID NO. 6 provides the amino acid sequence for CD3ζSS-mSA2-CD3ζ.

Plasmids pFSC074b and pFSC086 include the following components. A first component is CD3ζ SP, which is the CD3ζ signal peptide sequence. The DNA sequence was synthesized by DNA2.0. The CD3ζ signal peptide is used for mSA2-linker-CD3ε fusion protein T-cell surface expression. A second component is CD3ζ, which is CD3 zeta coding sequence. CD3ζ cDNA was purchased from MyBioSource.com (CAT #: MBS1278153). A third component is mSA2 biotin binding protein mSA2 (Monomeric Streptavidin 2). The DNA sequence for mSA2 was synthesized by DNA 2.0. The mSA2 amino acid sequence was obtained from the scientific literature (see Lim et al., *Stable, high-affinity streptavidin monomer for protein labeling and monovalent biotin detection*, Biotechnol Bioeng. (110):57-67 (2013)). A fourth component is CD3ζ crispr left HA and right HA, wherein the sequence was obtained from NCBI (access number: NG_007384.1) and the DNA sequence was synthesized by DNA2.0. The CD3ζ homology arms were used for modifying CD3ζ locus with CRISPR-cas9 gene editing system. Endogenous CD3ζ subunit was disrupted after mSA2-linker-CD3ζ integration into CD3ζ locus through homologous recombination. Mutations were introduced into the synthetic DNA sequence of CD3ζ crispr homology arms to prevent CRISPR/Cas9 from re-modifying the target sequence once the desired edit has been introduced. A fourth component is the EF-1α promoter, which is the human elongation factor 1α-subunit (hEF-1α) promoter for high-level expression across a broad range of species and cell types. A fifth component is P2A, which is the 2A peptide derived from the porcine teschovirus-1. A sixth component is Furin, which is the furin cleavage site. A seventh component is the rEF1 promoter, which is derived from the InvivoGen pVITRO1-blasti-mcs vector and is of rat origin. Like its human counterpart, it displays a strong activity that yields similar levels of expression. EF-1α promoters are expressed at high levels in all cell cycles and lower levels during G0 phase. EF-1α promoters are also non-tissue specific and are highly expressed in all cell types. An eighth component is the CMV enhancer, which is the major immediate early enhancer of the human cytomegalovirus (HCMV), is located between nucleotides −118 and −524, and is composed of unique and repeated sequence motifs. The HCMV enhancer can substitute for the 72-bp repeats of SV40 and is several folds more active than the SV40 enhancer. A ninth component is FMDV IRES, which is the internal ribosome entry site of the Foot and Mouth Disease Virus, and which enables the translation of two open reading frames from one mRNA with high levels of expression. A tenth component is EM7, which is a bacterial promoter that enables the constitutive expression of the antibiotic resistance gene in *E. coli*. An eleventh component is Blasti, wherein resistance to Blasticidin S is conferred by the bsr gene from *Bacillus cereus*. In bacteria, bsr is expressed from the constitutive *E. coli* EM7 promoter. In mammalian cells, bsr is transcribed from the rat EF-1aα promoter as a polycistronic mRNA and translated by way of the FMDV IRES. A twelfth component is EF1 pAn, which is a strong polyadenylation signal. InvivoGen uses a sequence starting after the stop codon of the EF1 cDNA and finishing after a bent structure rich in GT.

Construction of eMA-CD3ε

Figure 95:
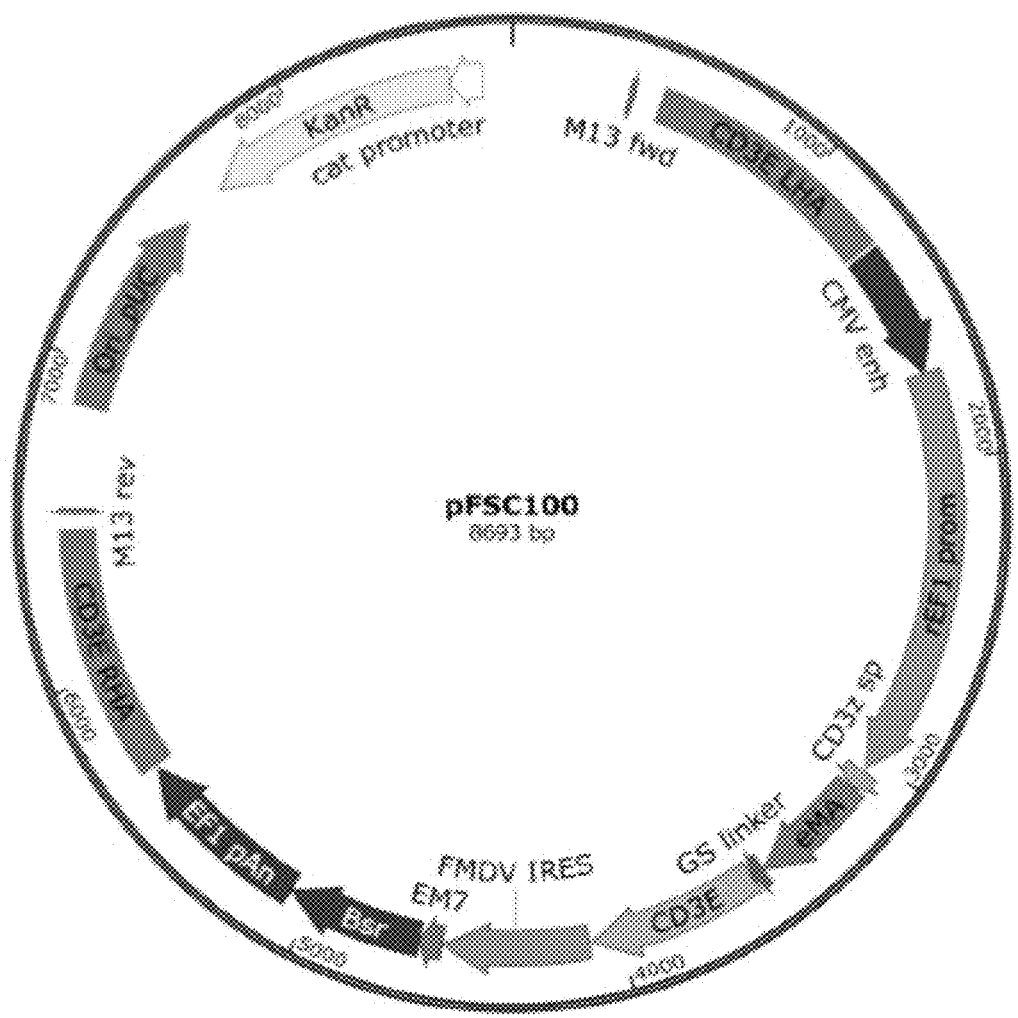
FIG. 95 is an illustration of plasmid pFSC100 (pFSC095-eMA-LL-CD3e-IRES-Blast) (eMA-CD3ε)

FIG. 95 illustrates plasmid pFSC100 (pFSC095-eMA-LL-CD3e-IRES-Blast) (eMA-CD3ε). This plasmid is the CD3ε locus knock in donor plasmid that contains CD3ε homology arms flanking the T-cell CD3ε subunit coding sequence genetically fused with biotin binding protein eMA gene on N-terminus of CD3ε through a GS linker. The eMA-linker-CD3ε cassette is driven by a rat EF1α promoter rEF1; a signal peptide from CD3ζ was used for eMA-linker-CD3ε fusion protein T-cell surface expression; blasticidin gene was used as a selection marker. SEQ ID NO. 7 provides the DNA sequence for CD3ζSS-eMA-CD3ε and SEQ ID NO. 8 provides the amino acid sequence for CD3ζSS-eMA-CD3ε.

Plasmid pFSC100 includes the following components. A first component is eMA, which is enhanced monoavidin (eMA). The amino acid sequence was derived from the scientific literature (see Lee et al., *A Rhizavidin Monomer with Nearly Multimeric Avidin-Like Binding Stability Against Biotin Conjugates*, Angew. Chem. Int. Ed. (55): 3393-3397 (2016) and the DNA sequence was codon-optimized and synthesized by DNA2.0. eMA has strong binding affinity for biotin. A second component is CD3ζSP, which is the CD3ζ signal peptide sequence. The DNA sequence was synthesized by DNA2.0. The CD3ζ signal peptide was used to export the eMA-CD3ε fusion protein to the T-cell surface. A third component is CD3ε, which is the CD3 epsilon coding sequence. The CD3ε coding sequence was obtained from NCBI (access number: NM_000733.3) and the DNA sequence was synthesized by IDT. CD3ε is part of the T cell receptor complex and it is used for signal transduction. A fourth component is CD3ε crispy left HA and right HA, which are the CD3ε homology arms. The sequence was obtained from NCBI (access number: NG_007383.1) and the DNA sequence was synthesized by IDT. CD3ε homology arms are used for modifying CD3ε locus with the CRISPR-cas9 gene editing system. Endogenous CD3ε subunit was disrupted after eMA-linker-CD3ε integration into CD3ε locus through homologous recombination. Mutations were introduced into the synthetic DNA sequence of CD3ε CRISPR homology arms to prevent CRISPR/Cas9 from re-modifying the target sequence once the desired edit has been introduced. A fifth component is the rEF1 promoter, which is from the InvivoGen pVITRO1-blasti-mcs vector and it is of rat origin. Like its human counterpart, this promoter displays a strong activity that yields similar levels of expression. EF-1α promoters are expressed at high levels in all cell cycles and lower levels during G0 phase. EF-1α promoters are also non-tissue specific and they are highly expressed in all cell types. A sixth component is the CMV enhancer, which is the major immediate early enhancer of the human cytomegalovirus (HCMV), located between nucleotides −118 and −524, and is composed of unique and repeated sequence motifs. The HCMV enhancer can substitute for the 72-bp repeats of SV40 and is several folds more active than the SV40 enhancer. A seventh component is FMDV IRES, which is the internal ribosome entry site of the Foot and Mouth Disease Virus and that enables the translation of two open reading frames from one mRNA with high levels of expression. An eighth component is EM7, which is a bacterial promoter that enables the constitutive expression of the antibiotic resistance gene in *E. coli*. The ninth component is Blasti, wherein resistance to Blasticidin S is conferred by the bsr gene from *Bacillus cereus*. In bacteria, bsr is expressed from the constitutive *E. coli* EM7 promoter. In mammalian cells, bsr is transcribed from the rat EF-1aα promoter as a polycistronic mRNA and translated by way of the FMDV IRES. A tenth component is EF1 pAn, which is a strong polyadenylation signal. InvivoGen uses a sequence starting after the stop codon of the EF1 cDNA and finishing after a bent structure rich in GT.

Figure 6:
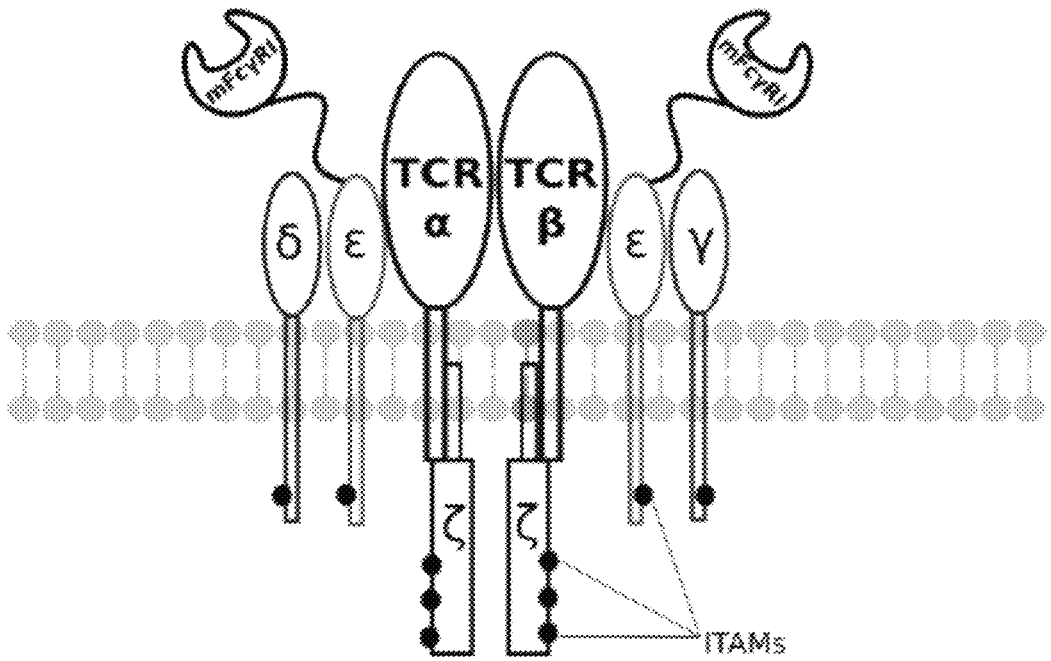
FIGS. 6-27 are illustrations of exemplary embodiments of the mouse FcγRI variant of the engineered receptors of the present invention, based either on the endogenous αβ T cell receptor complex or the endogenous γδ T cell receptor complex.
Figure 7:
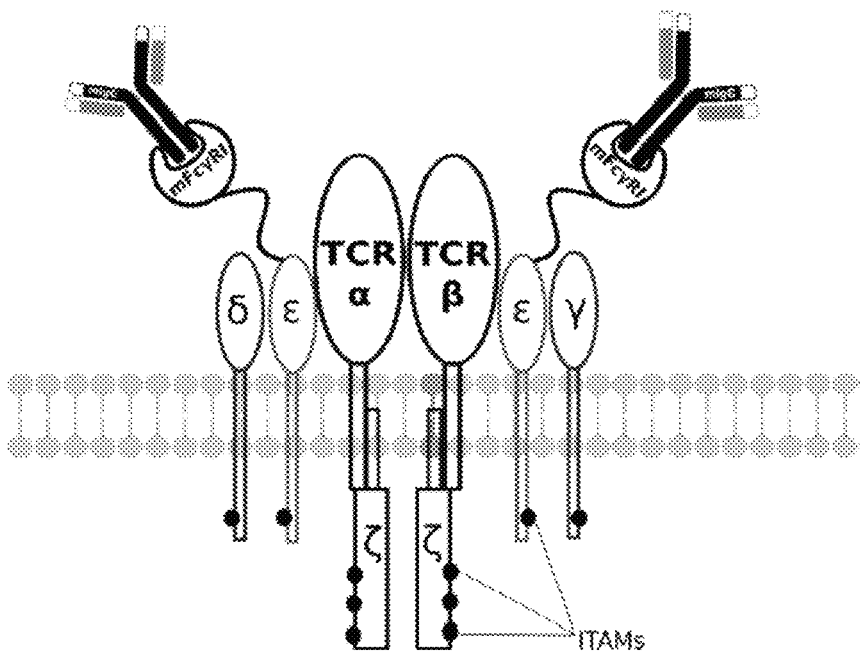
Figure 8:
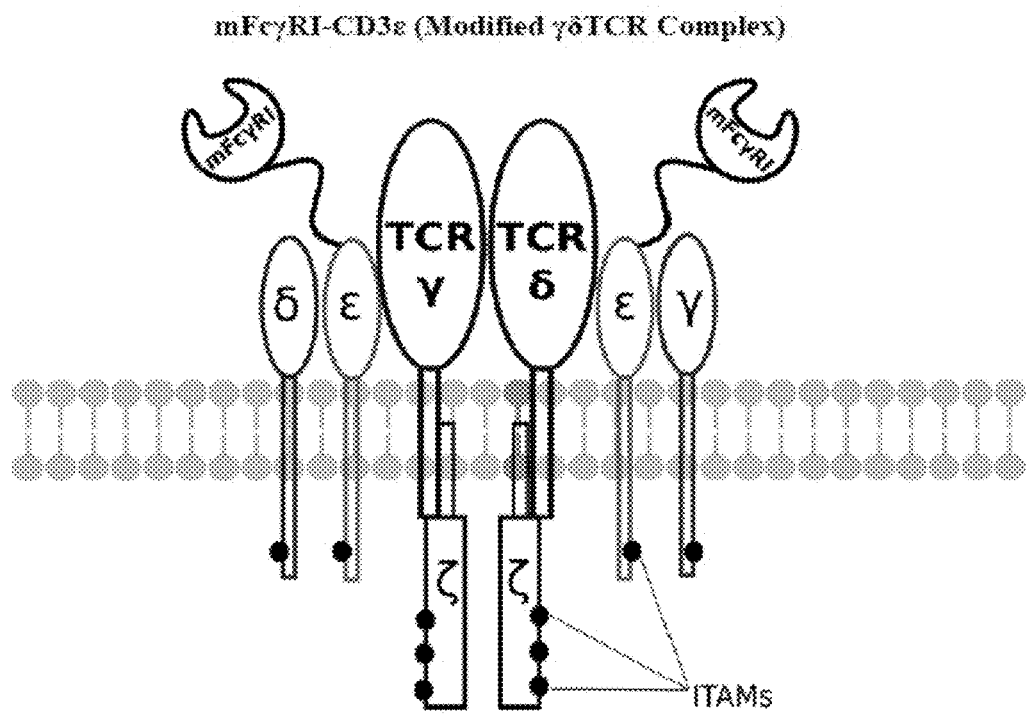
Figure 9:
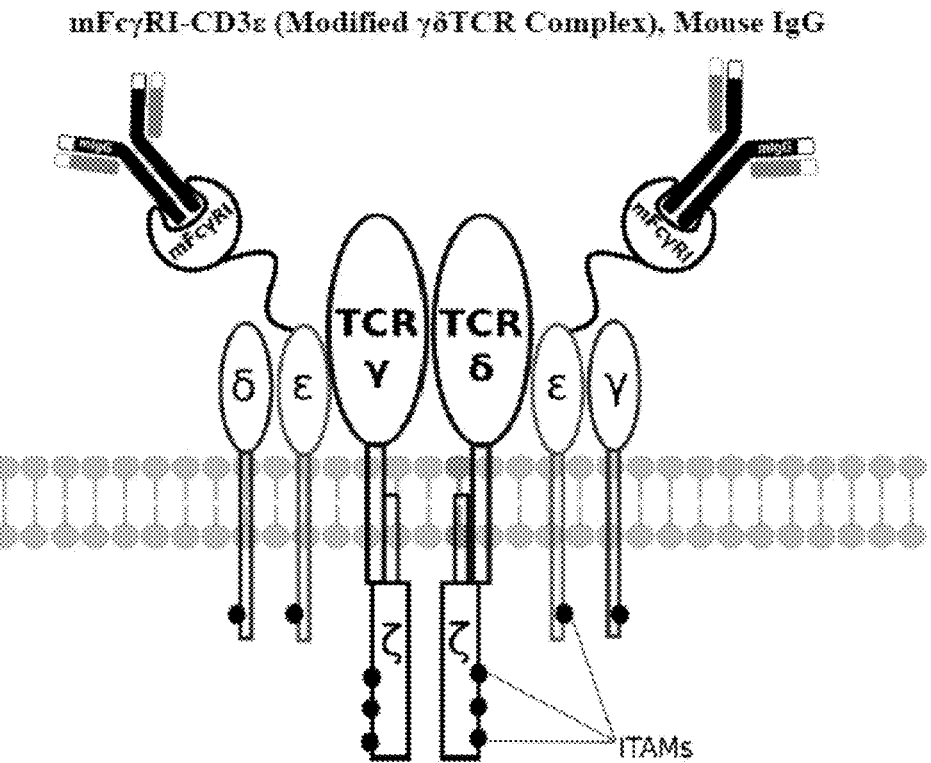
Figure 10:
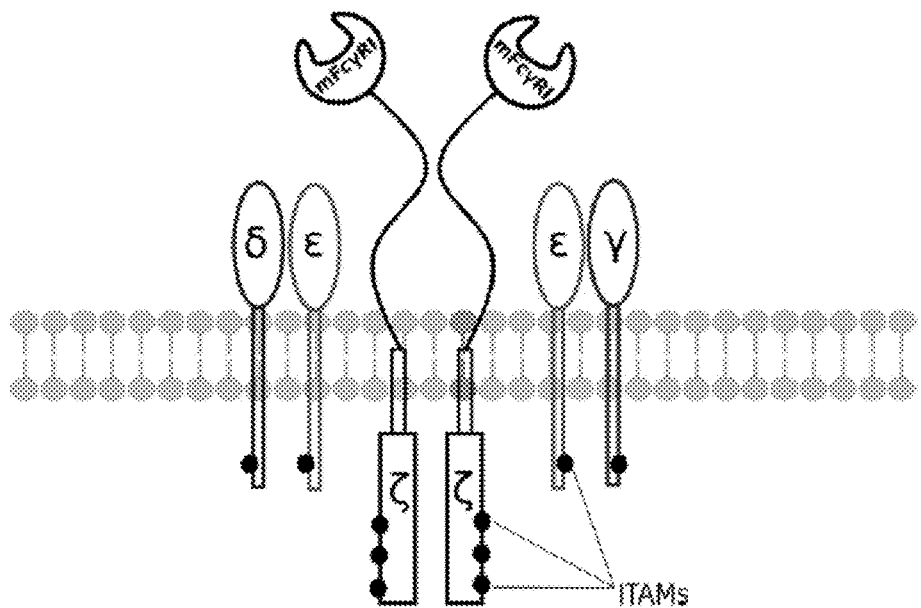
Figure 11:
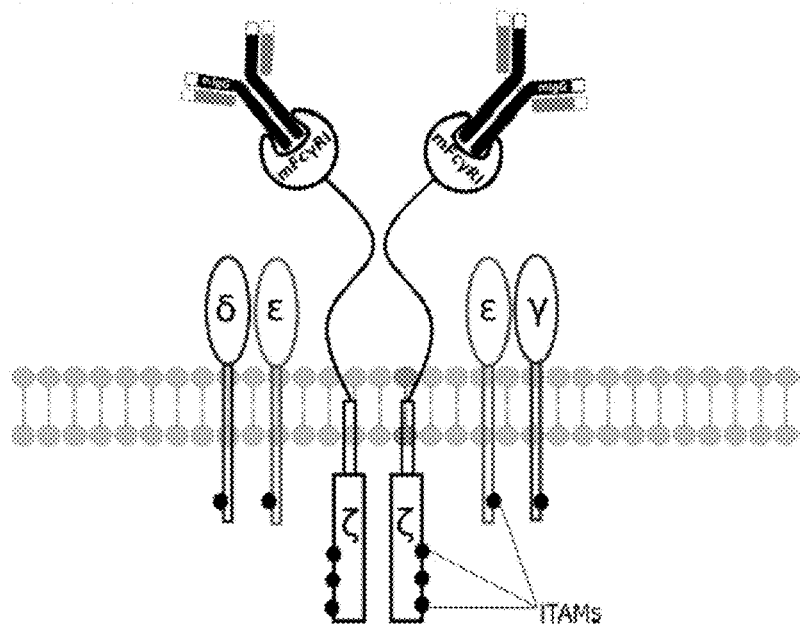
Figure 12:
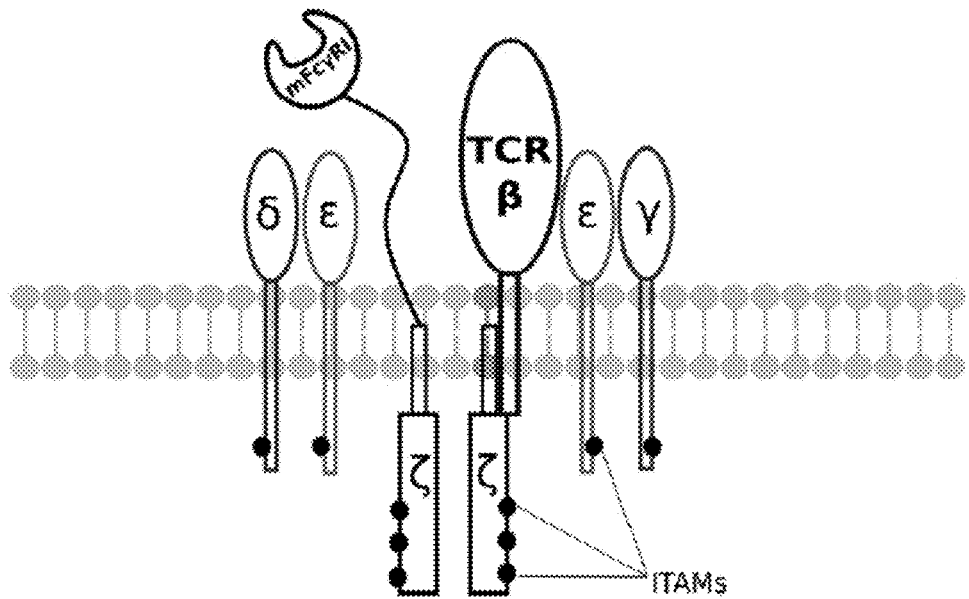
Figure 13:
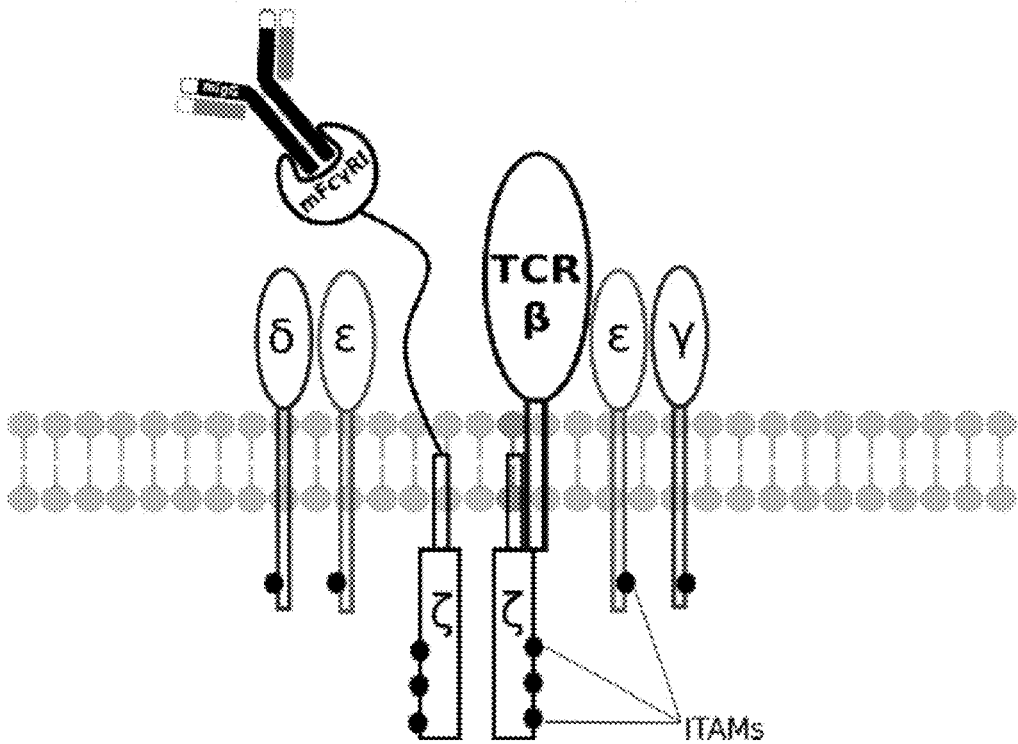
Figure 14:
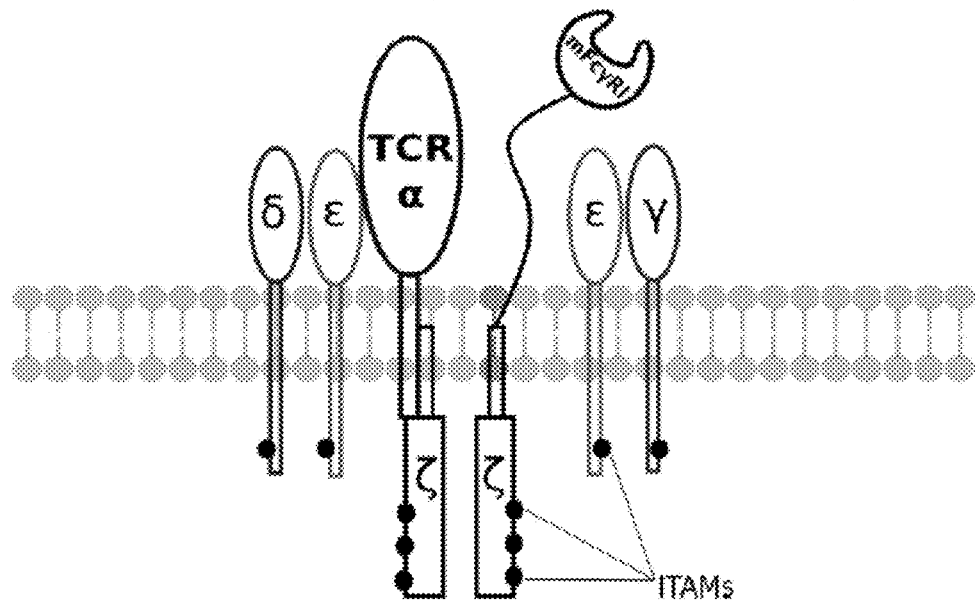
Figure 15:
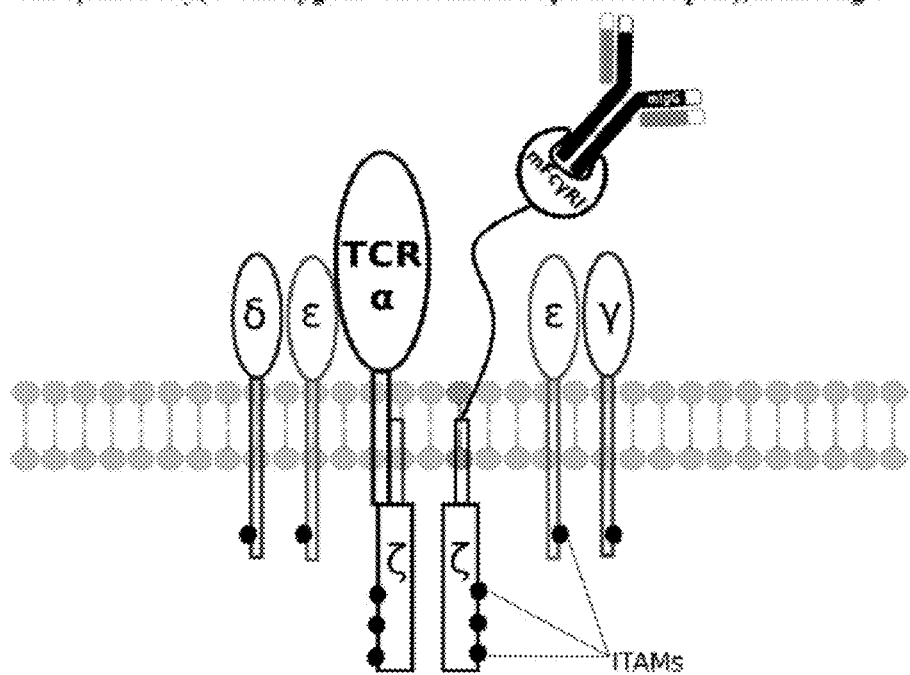
Figure 16:
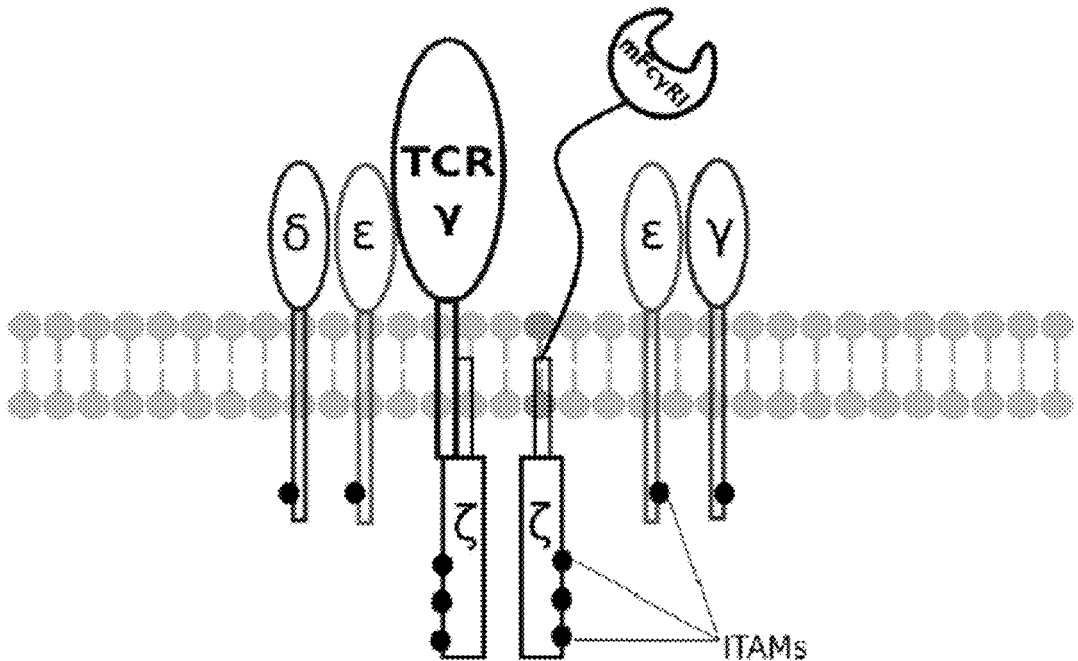
Figure 17:
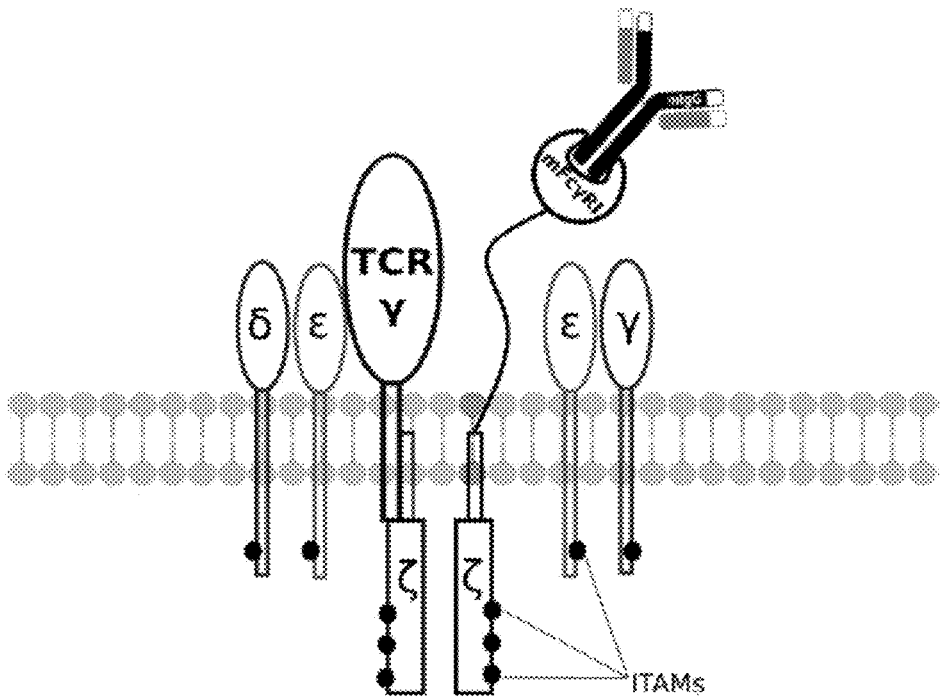
Figure 18:
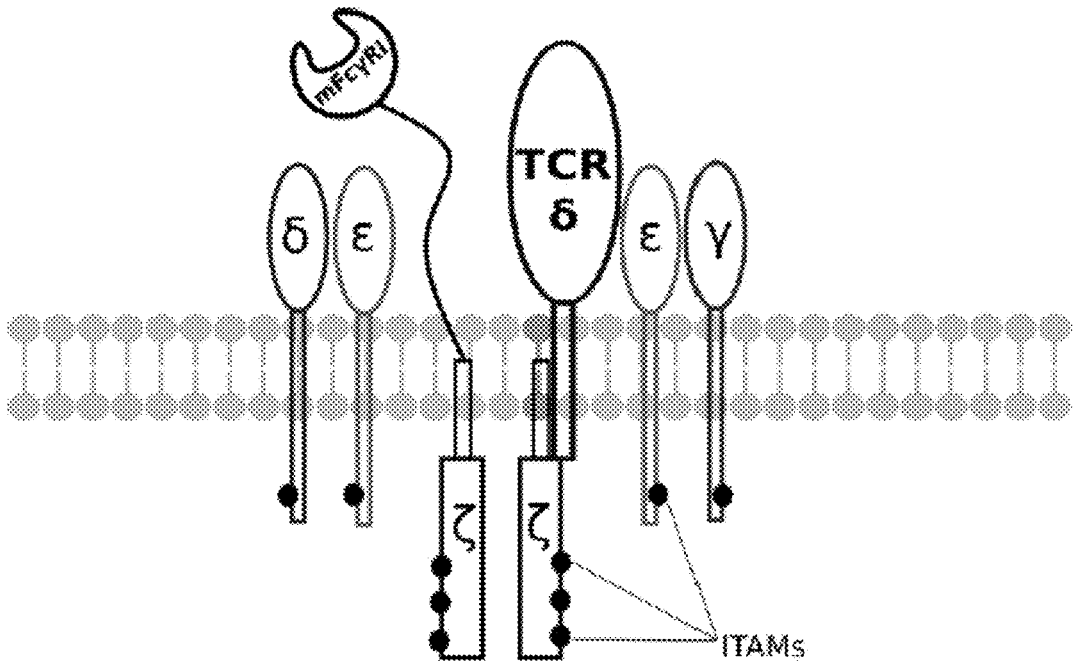
Figure 19:
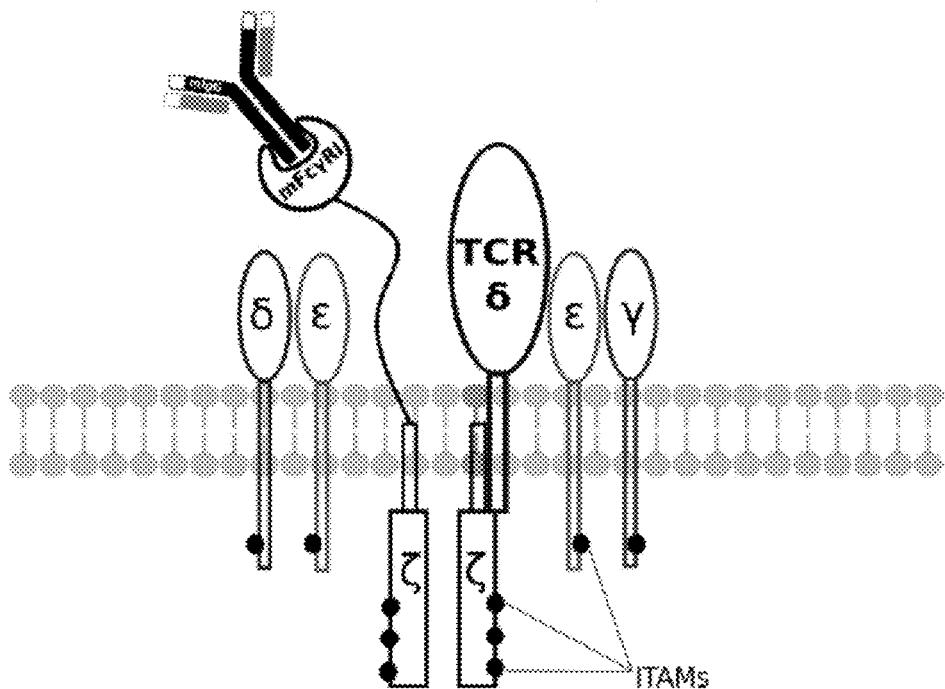
Figure 20:
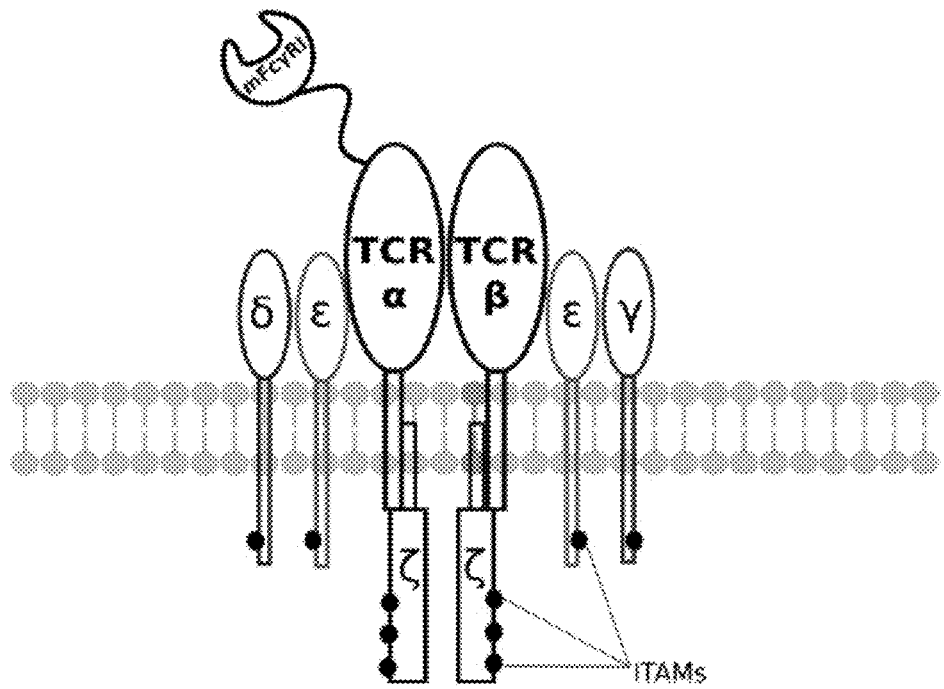
Figure 21:
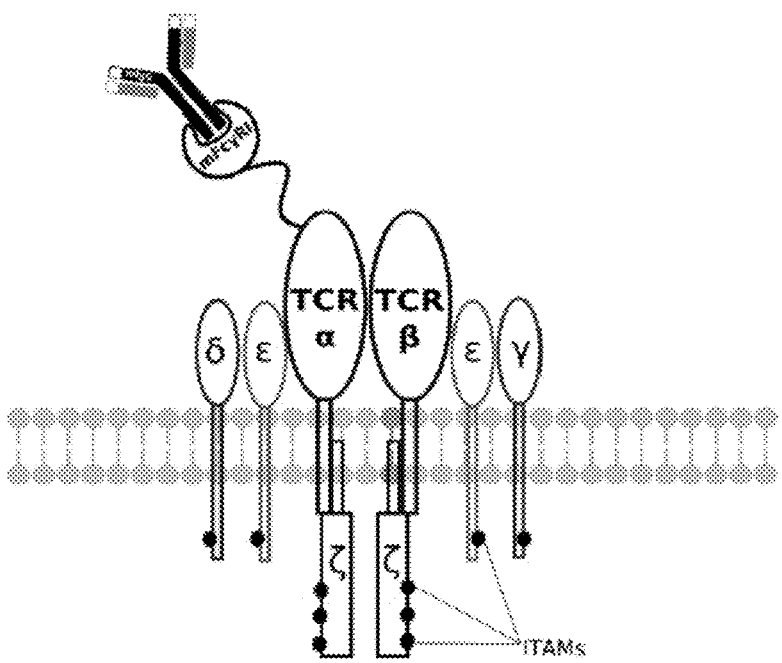
Figure 22:
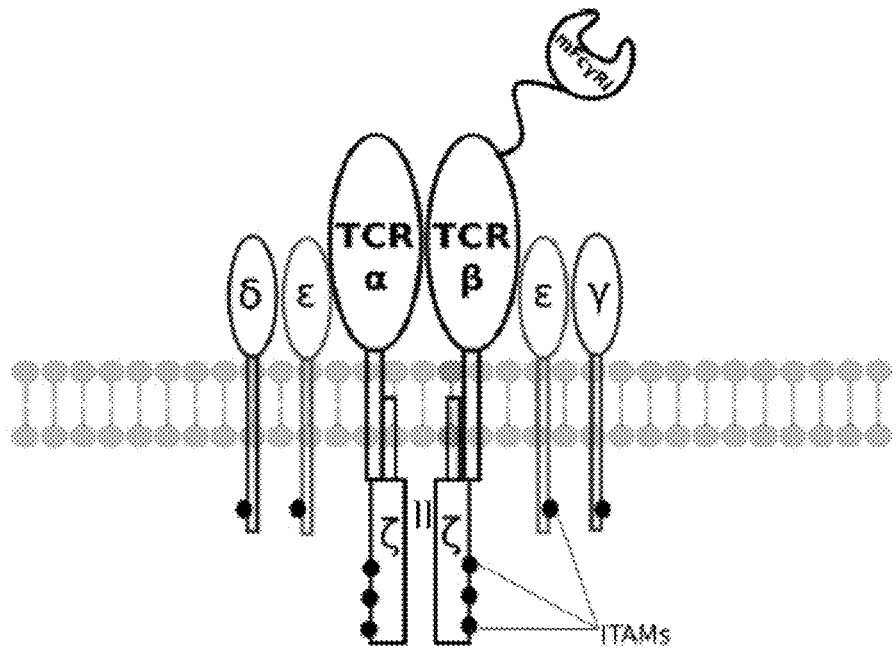
Figure 23:
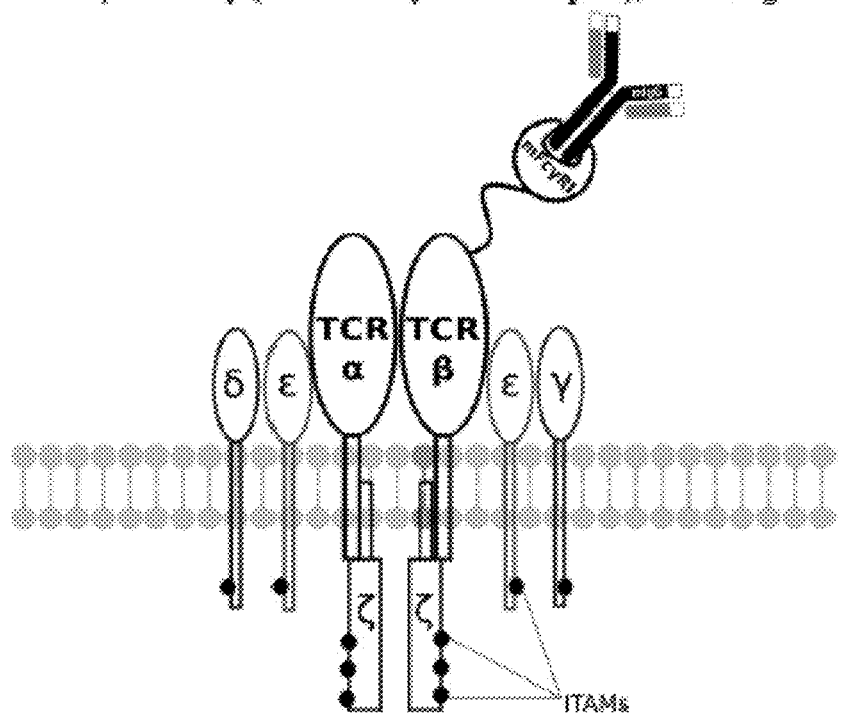
Figure 24:
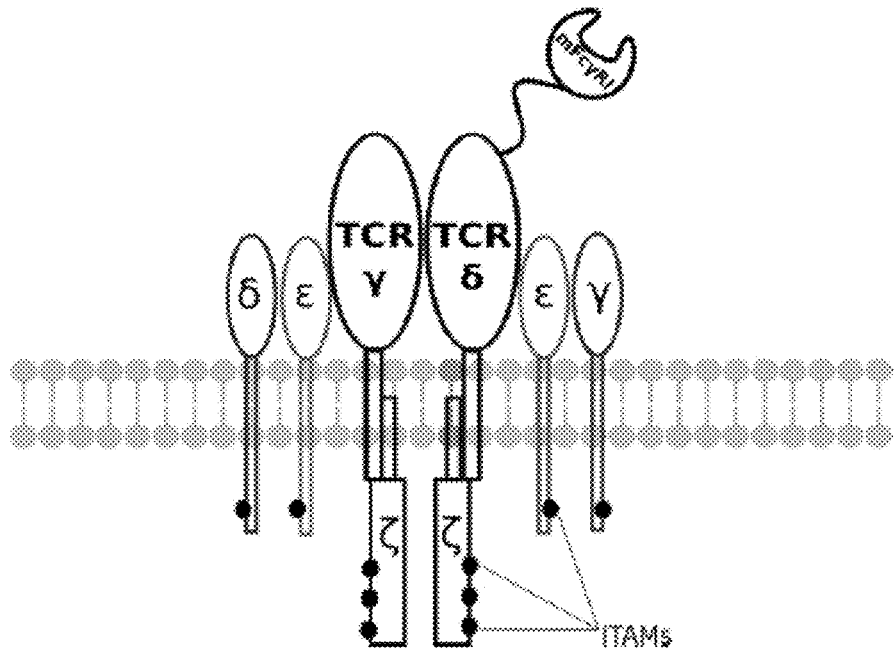
Figure 25:
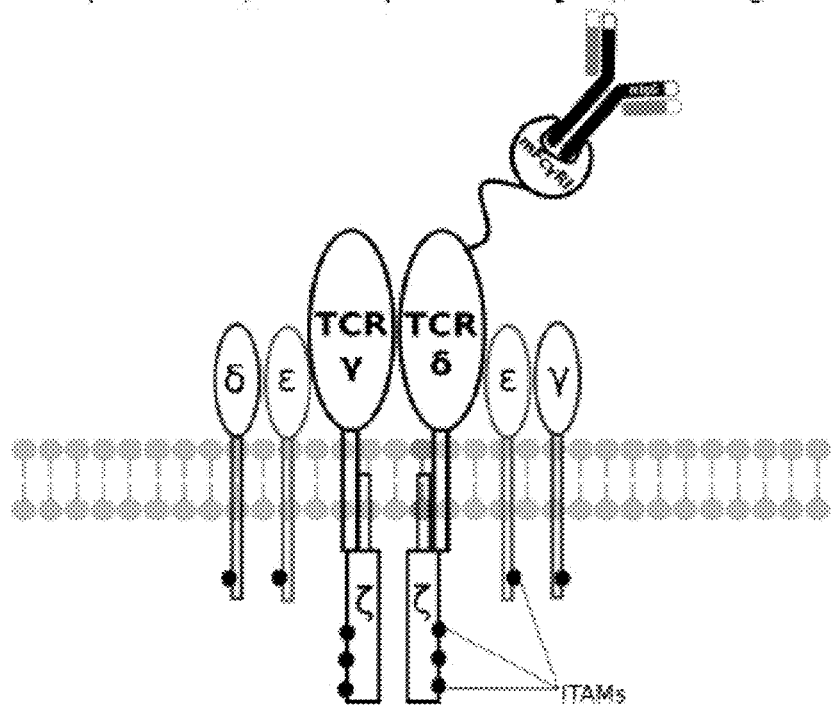
Figure 26:
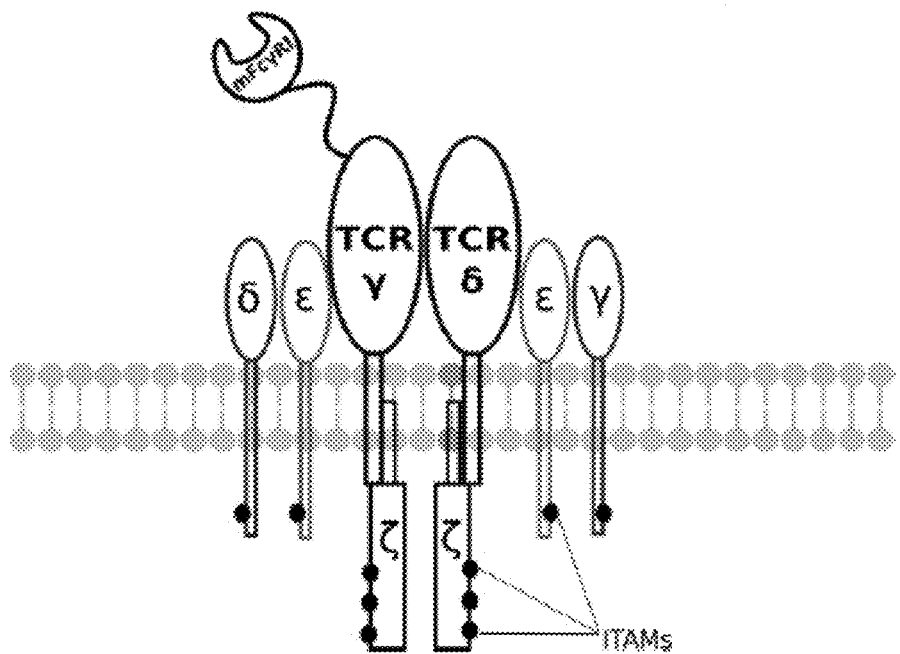
Figure 27:
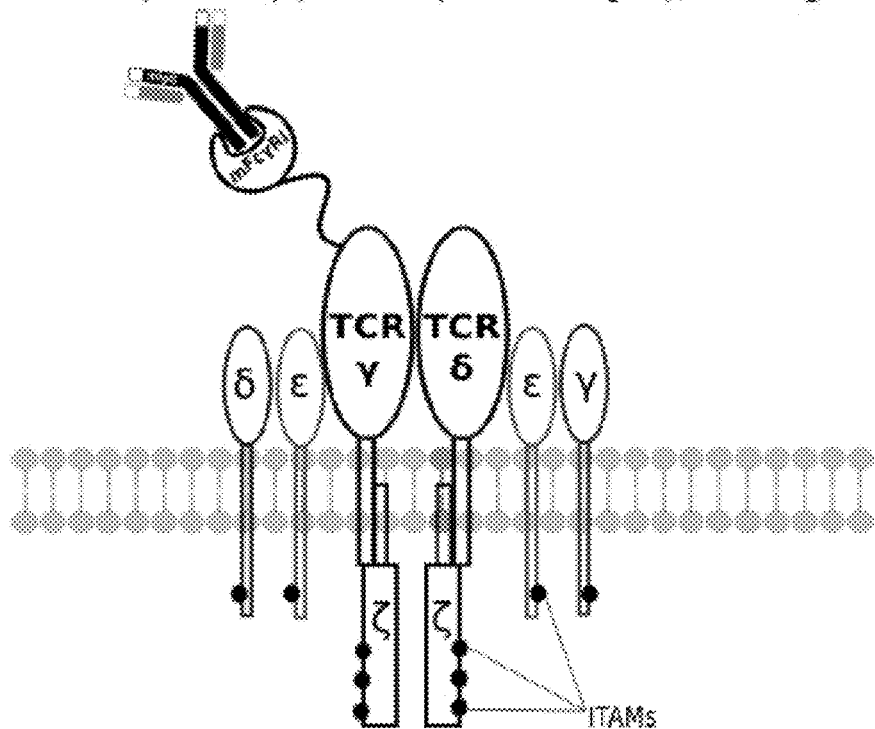
Figure 28:
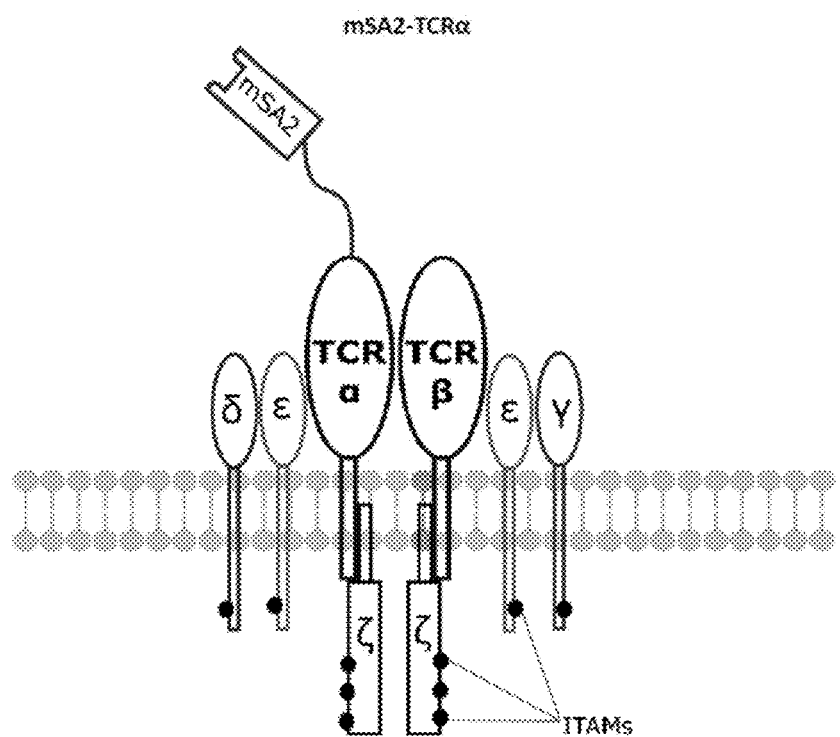
FIGS. 28-45 are illustrations of exemplary embodiments of the mSA2 variant of the engineered receptors of the present invention, based either on the endogenous αβ T cell receptor complex or the endogenous γδ T cell receptor complex.
Figure 29:
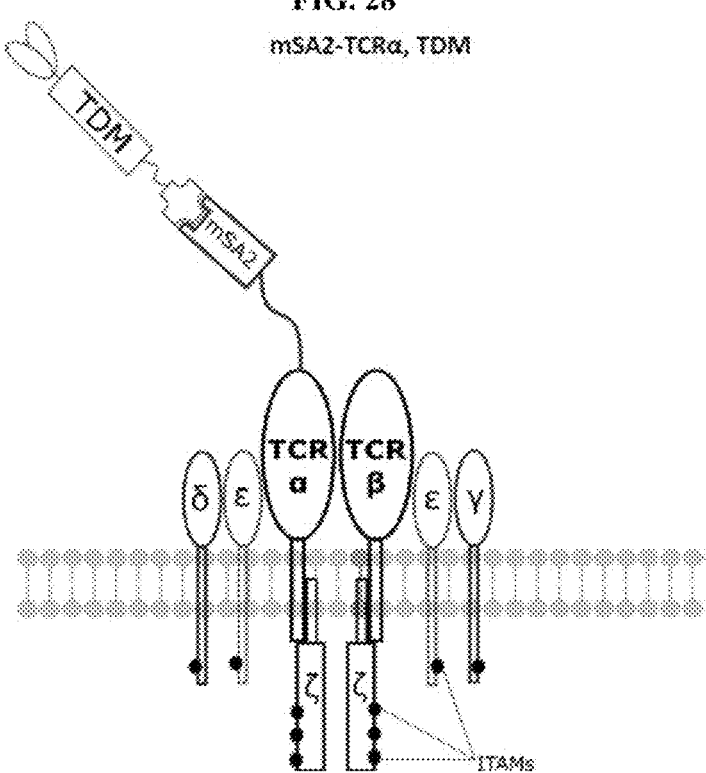
Figure 30:
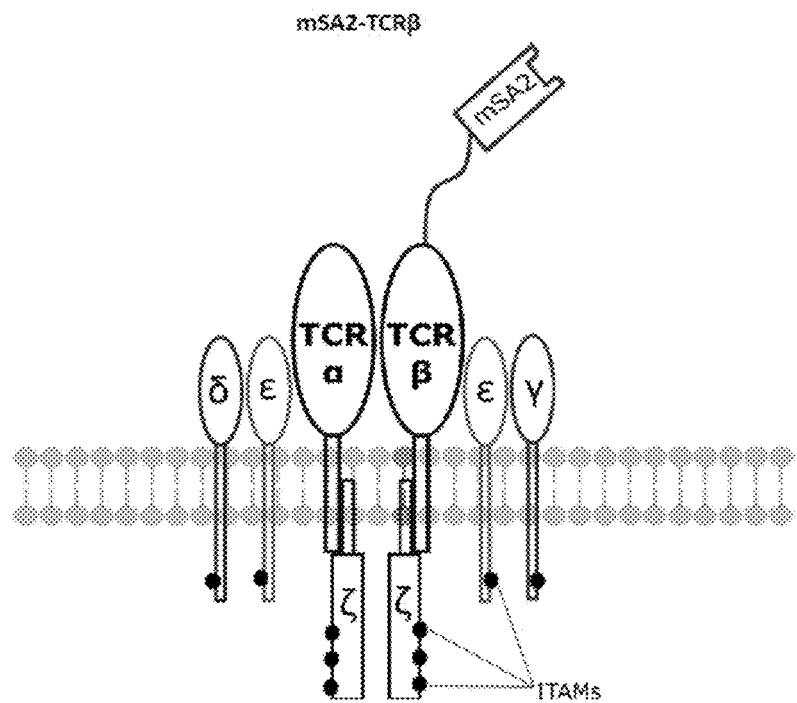
Figure 31:
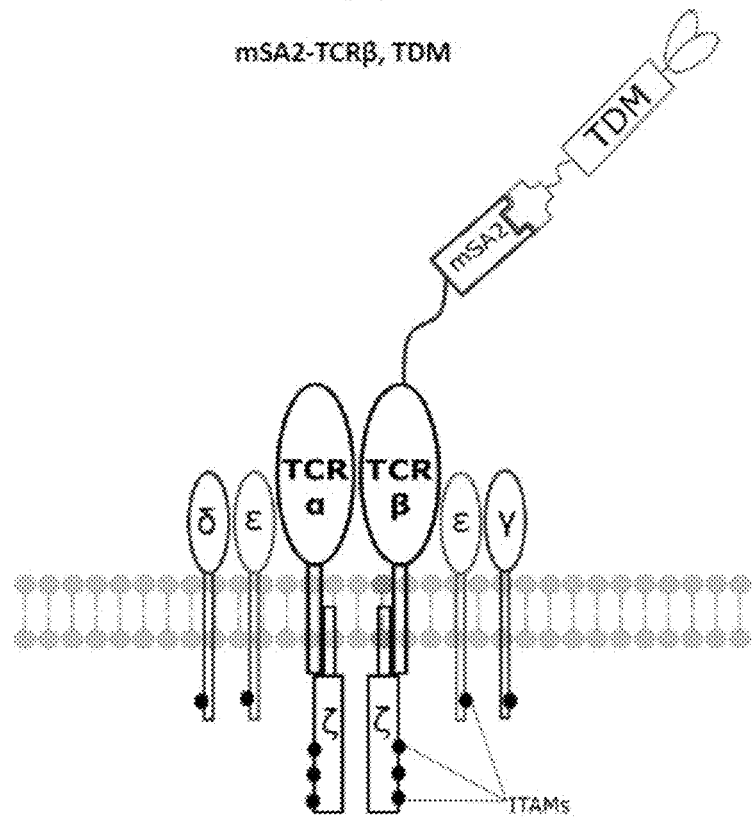
Figure 32:
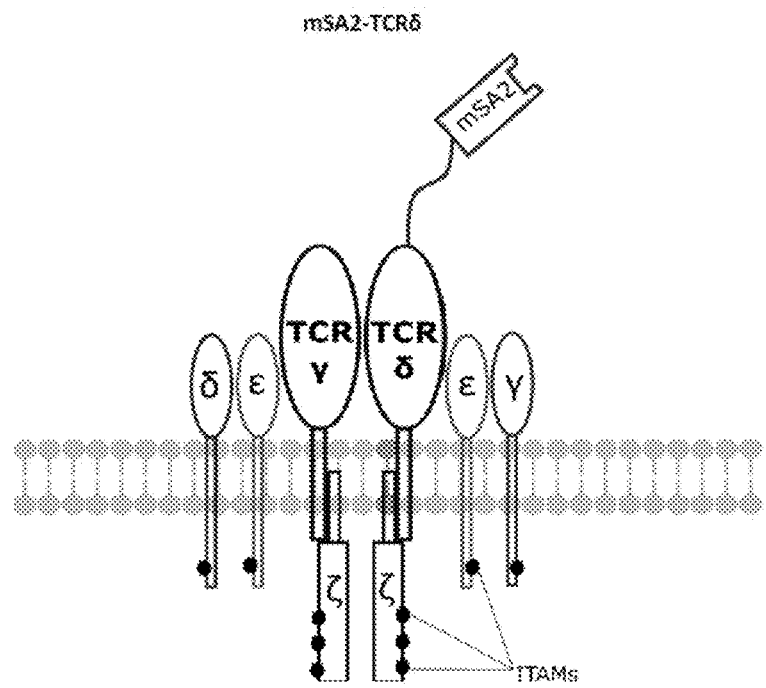
Figure 33:
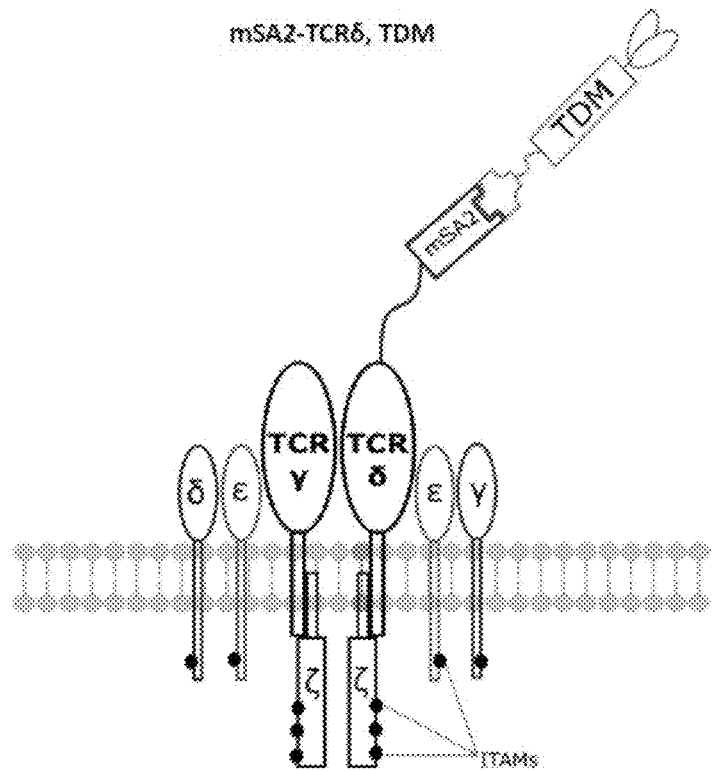
Figure 34:
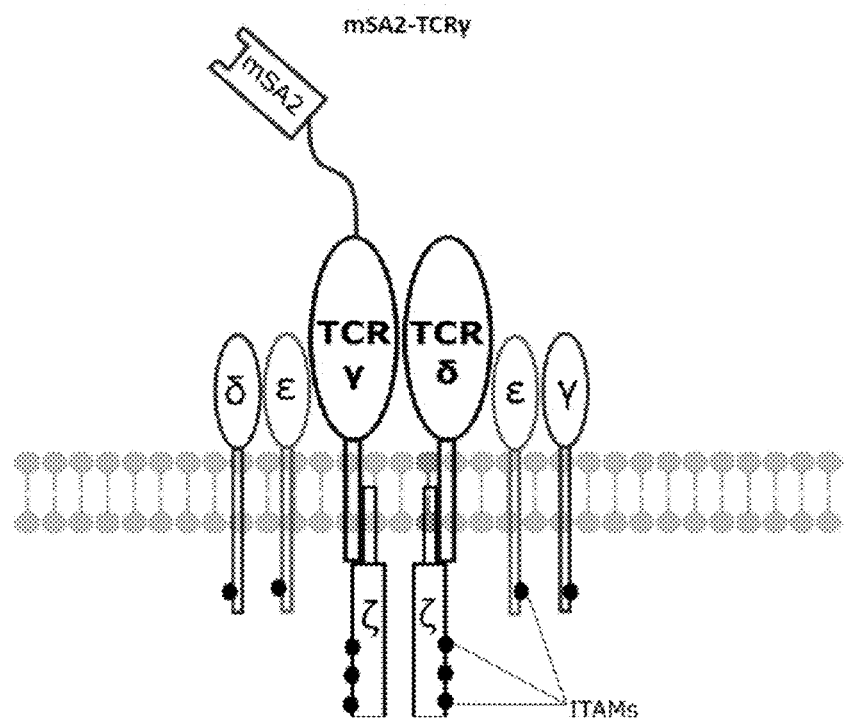
Figure 35:
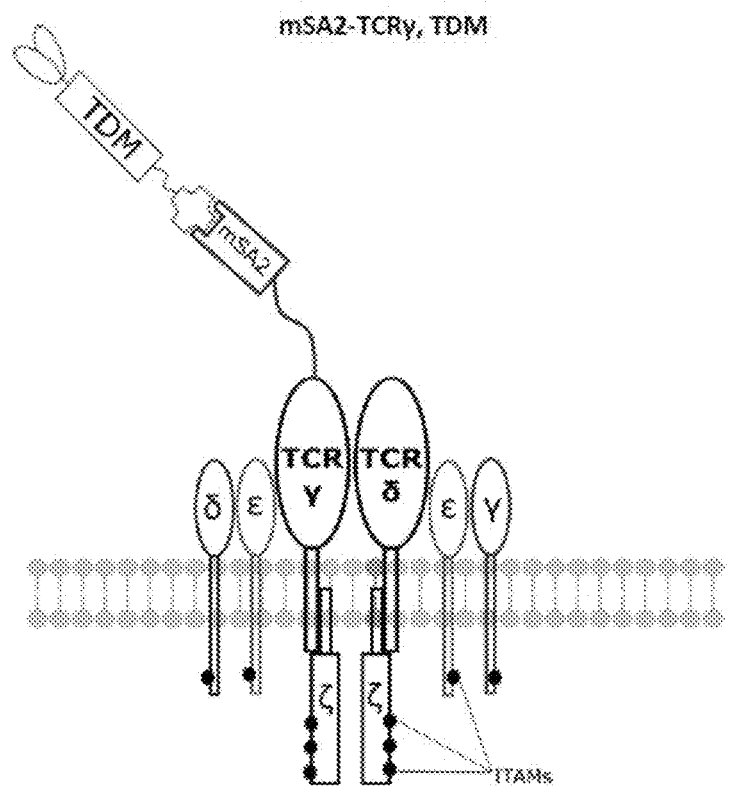
Figure 36:
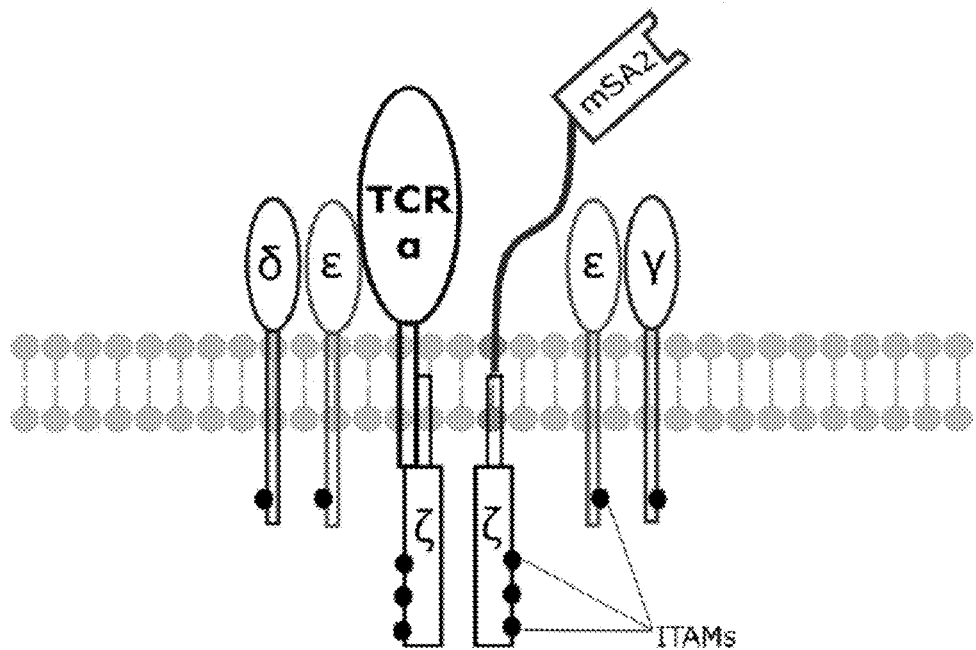
Figure 37:
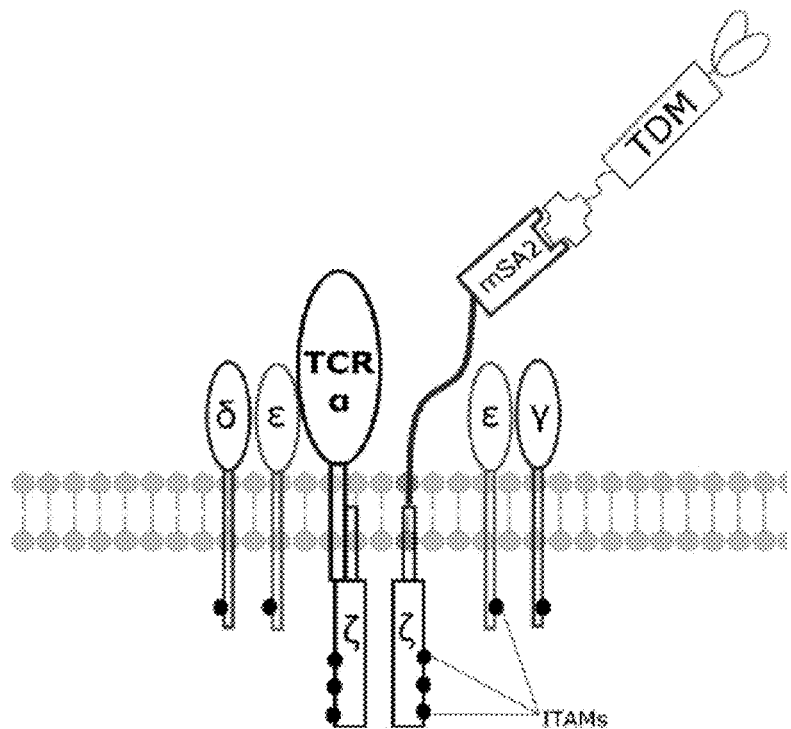
Figure 38:
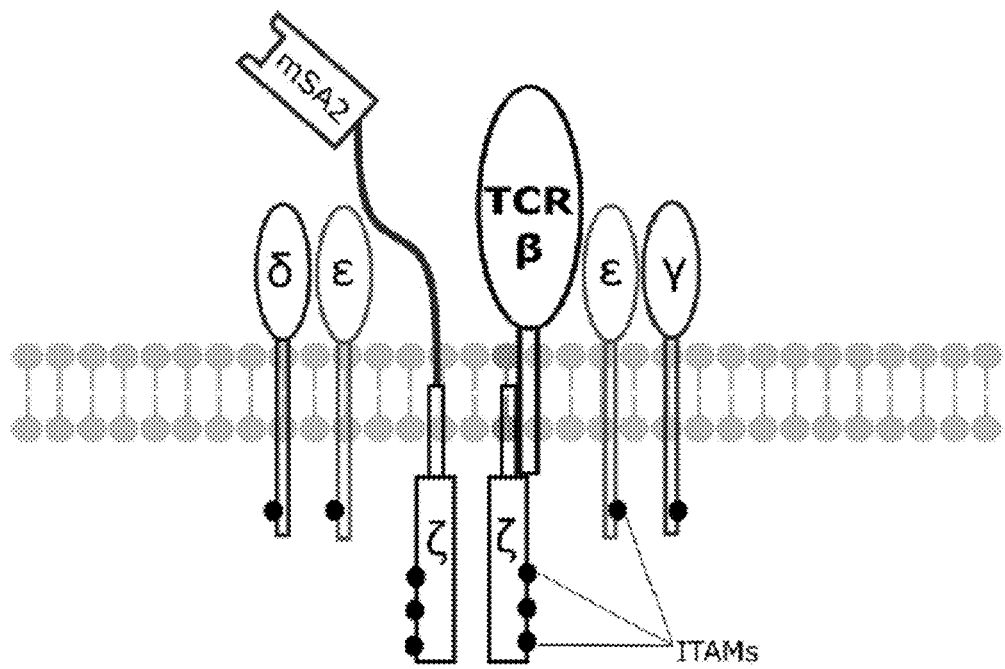
Figure 39:
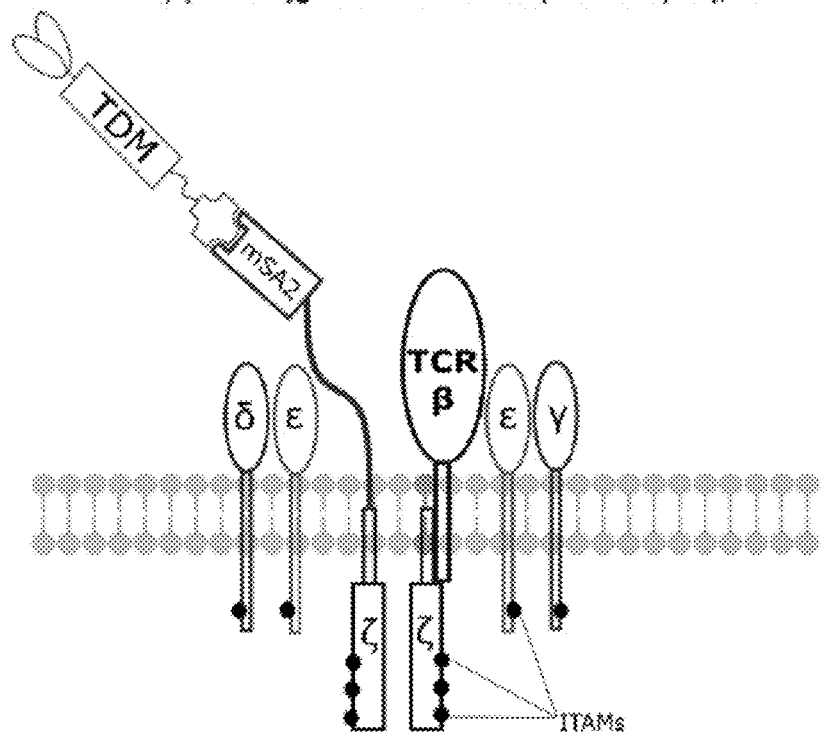
Figure 40:
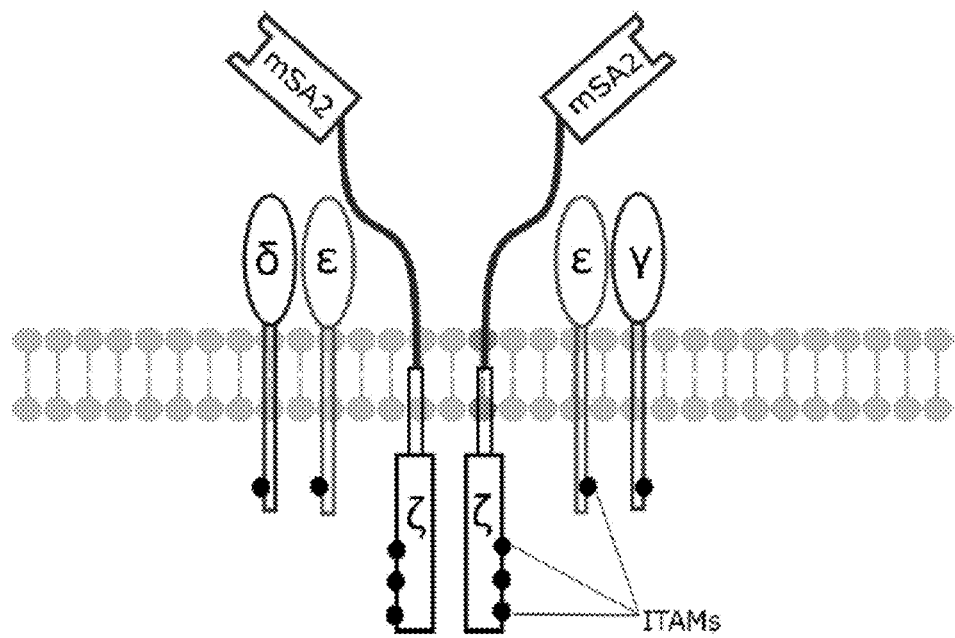
Figure 41:
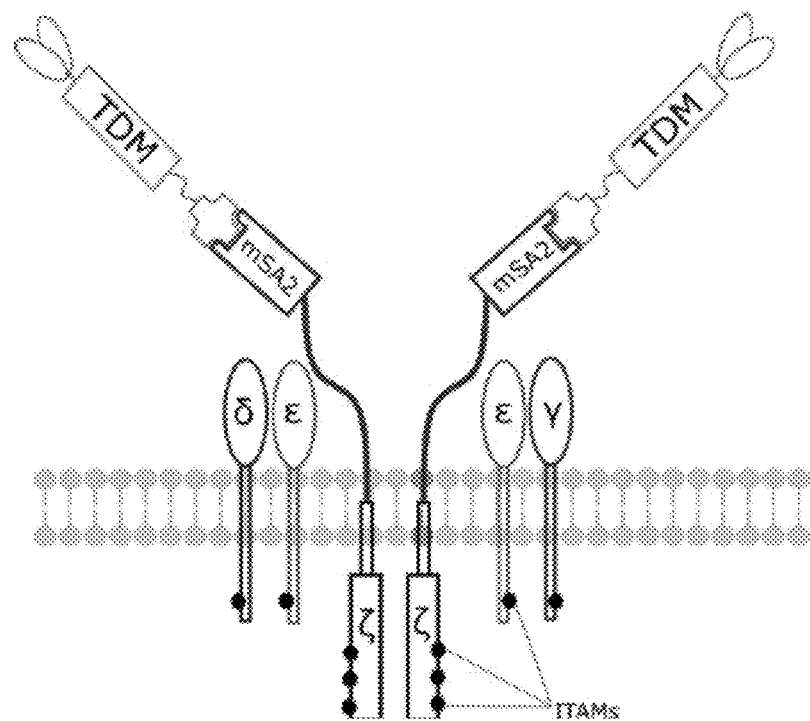
Figure 42:
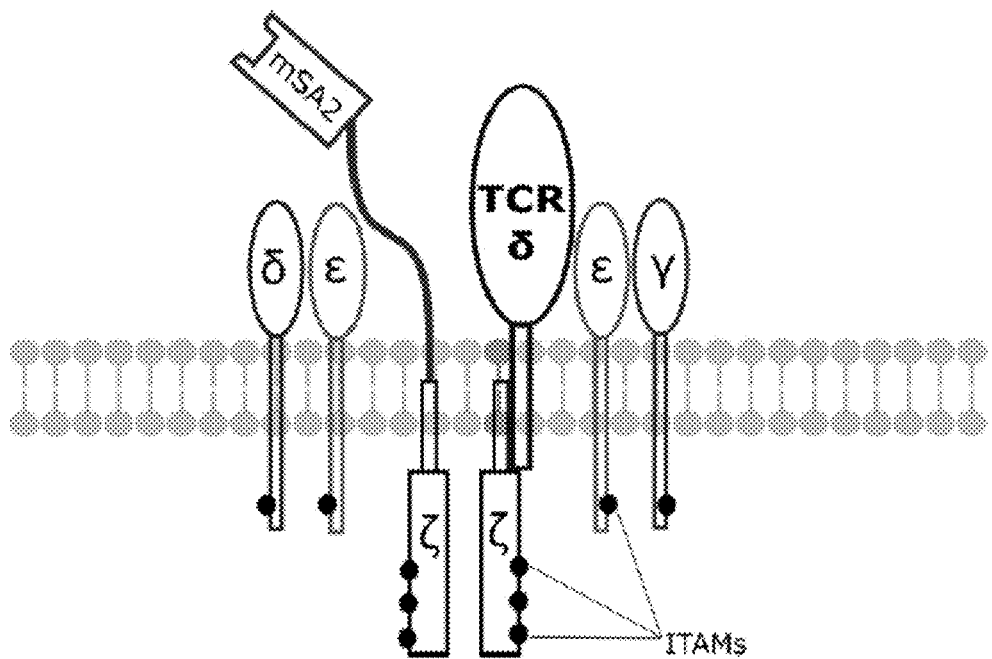
Figure 43:
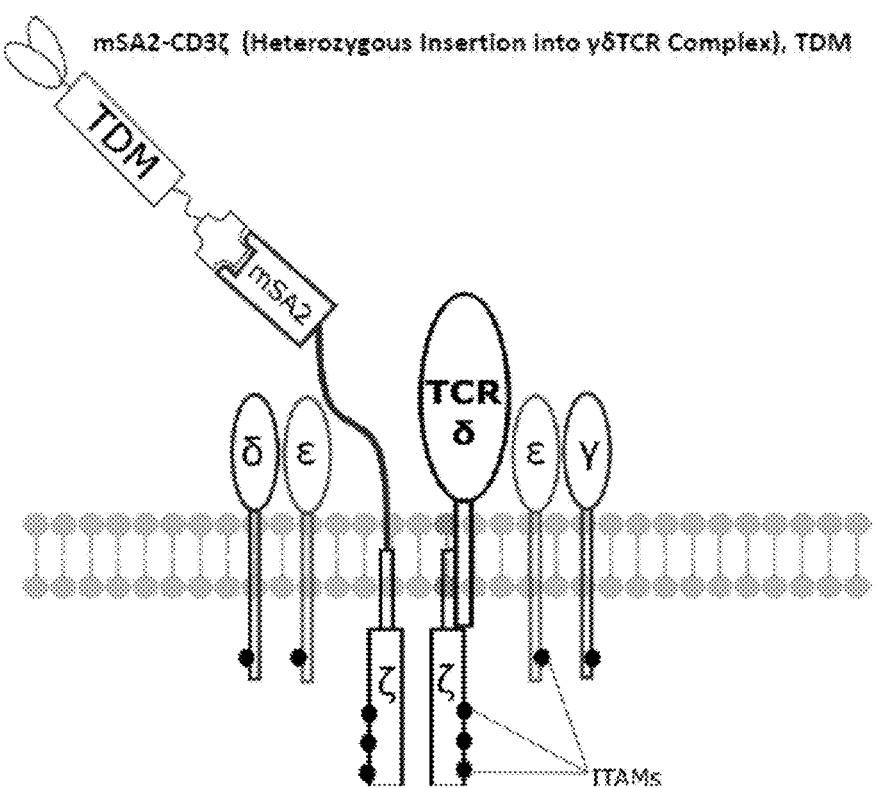
Figure 44:
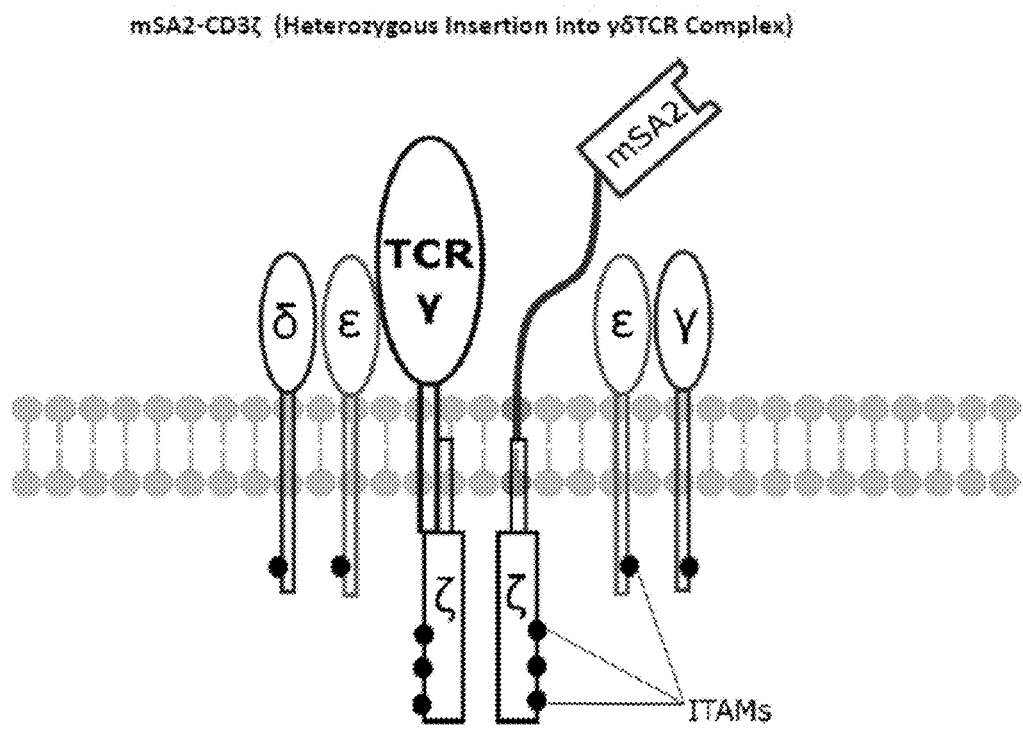
Figure 45:
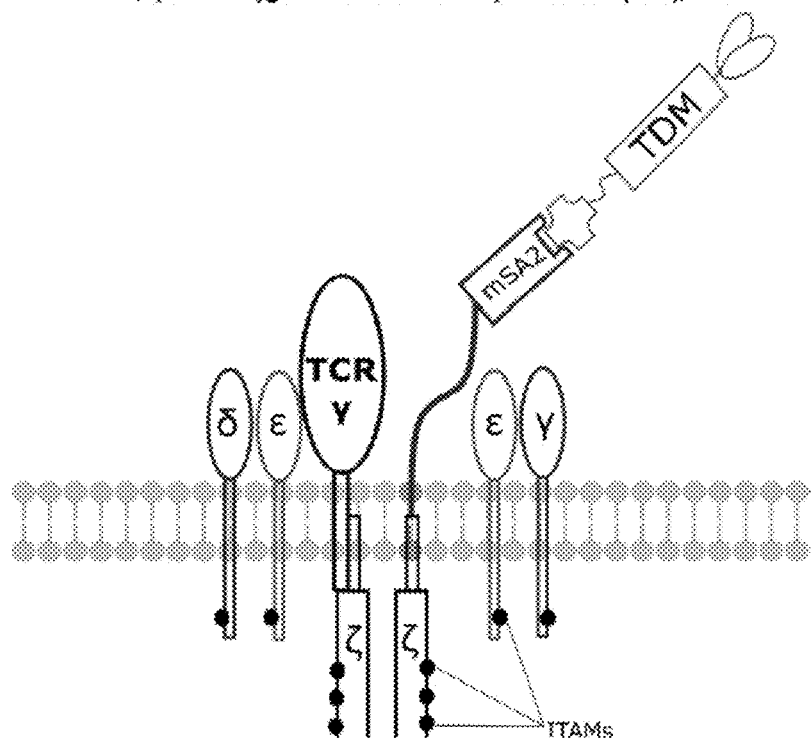
Figure 52:
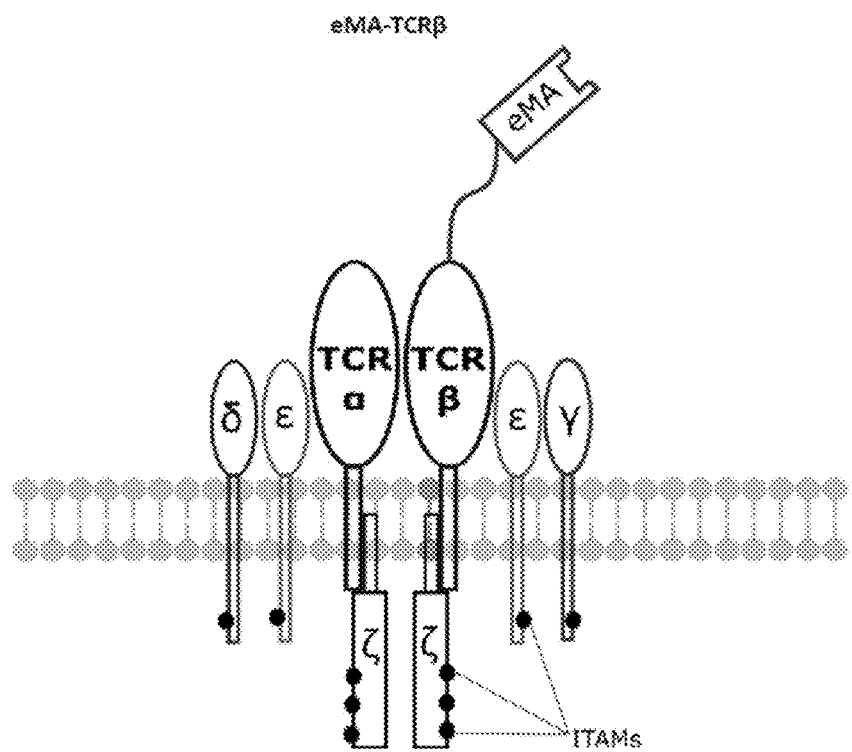
Figure 53:
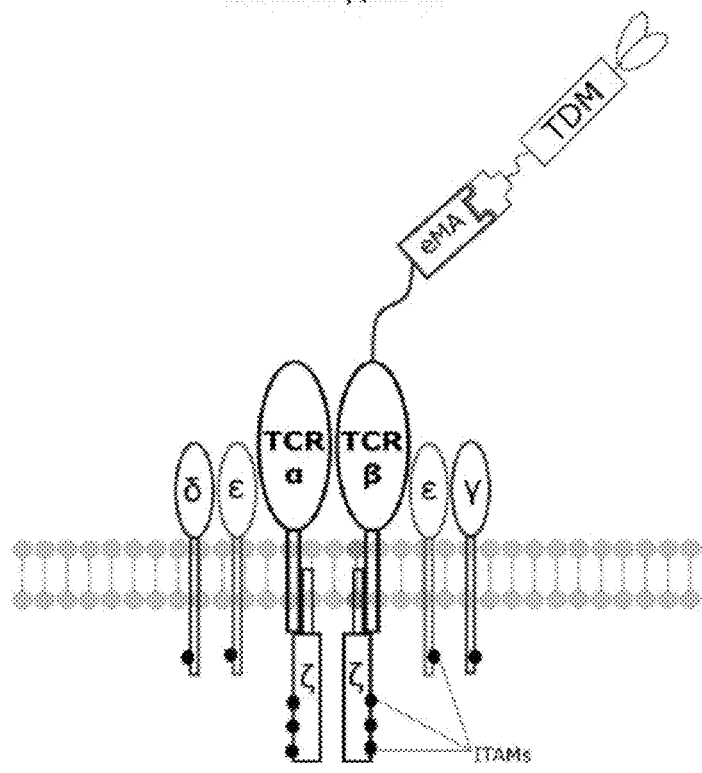
Figure 54:
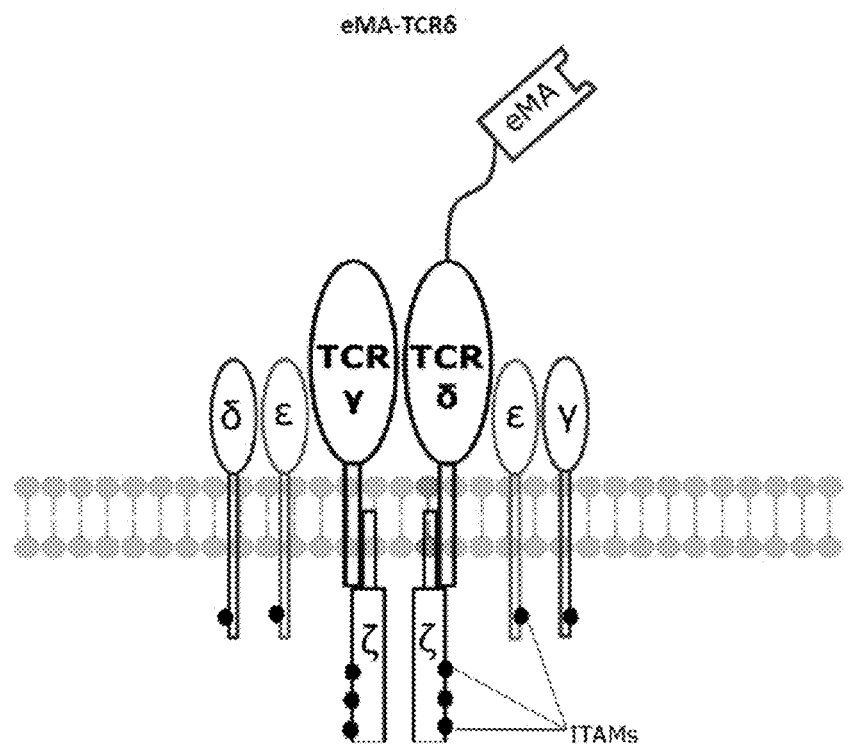
Figure 55:
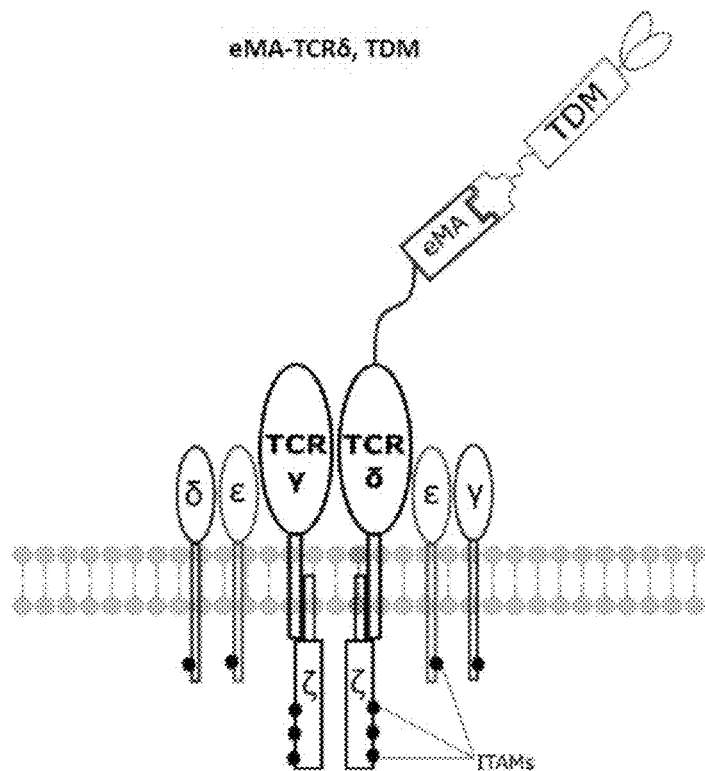
Figure 56:
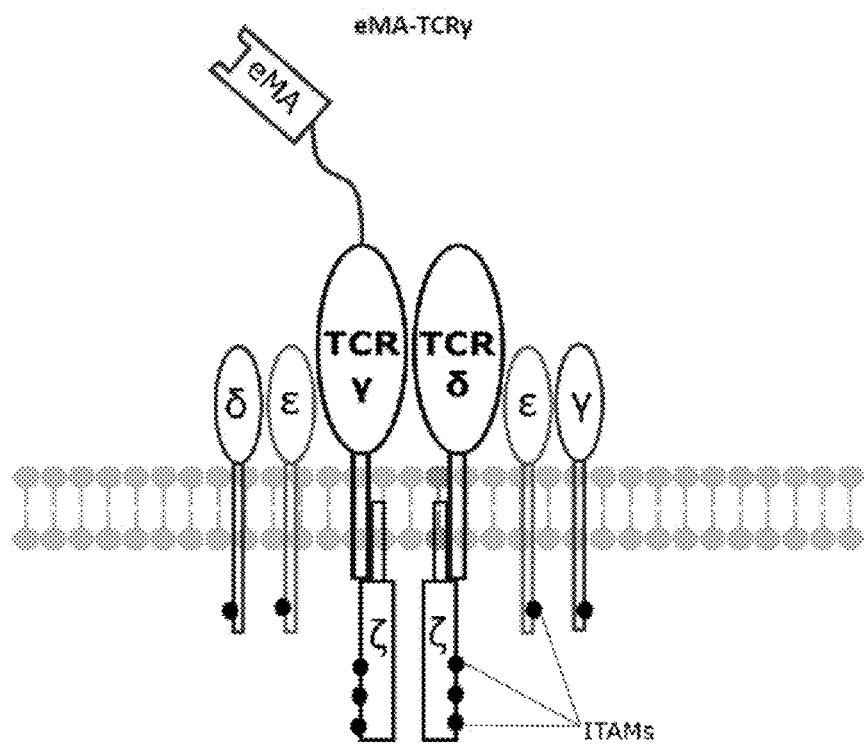
Figure 57:
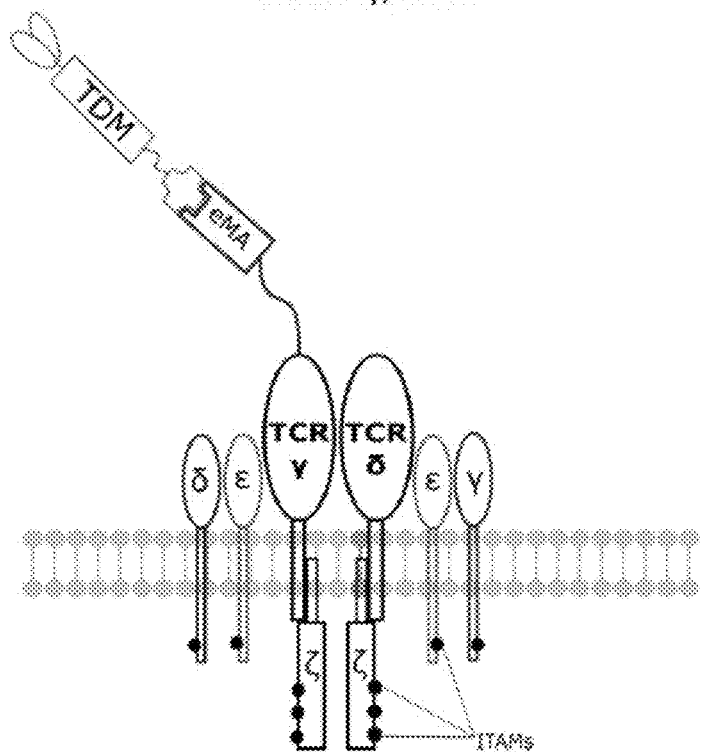
Figure 58:
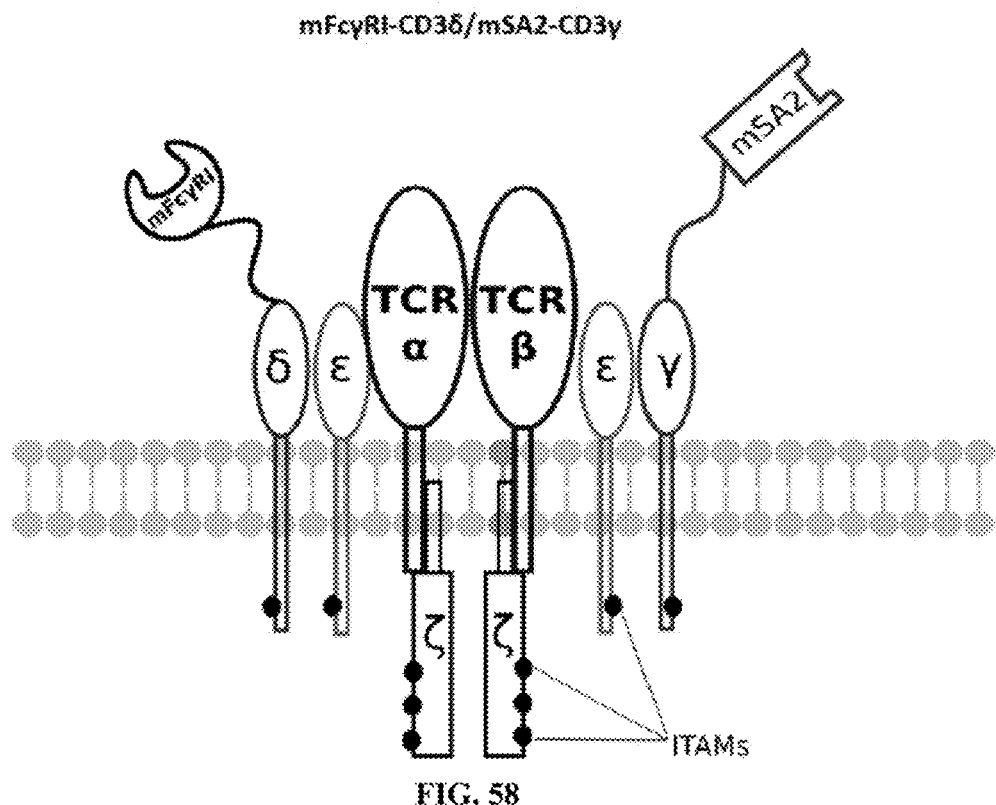
FIGS. 58-69 are illustrations of exemplary embodiments of the FcγRI/mSA2 combination variant of the present invention, based either on the endogenous αβ T cell receptor complex or the endogenous γδ T cell receptor complex.
Figure 59:
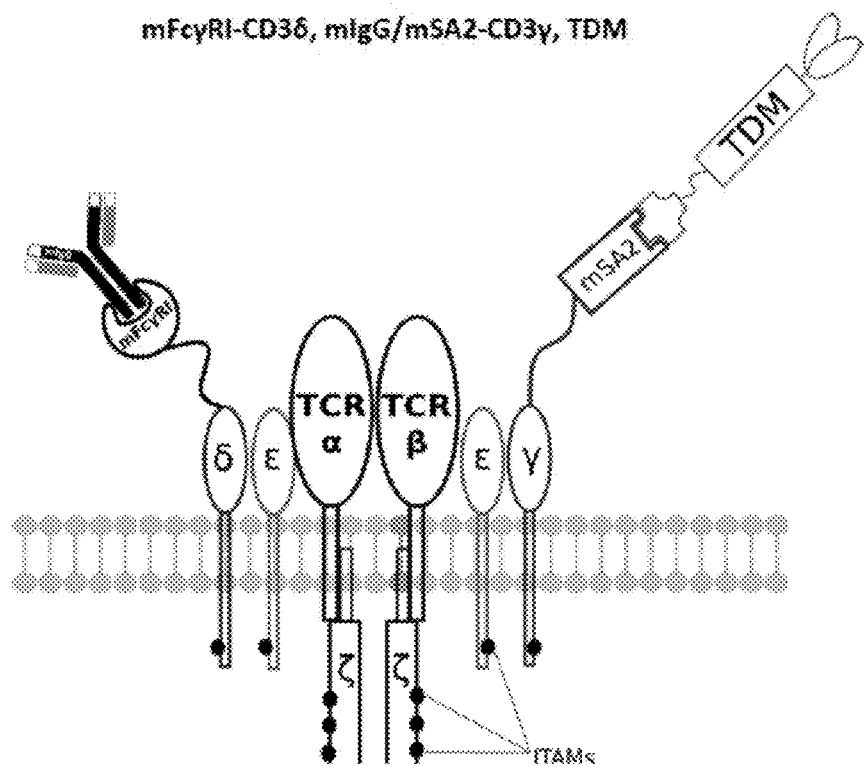
Figure 60:
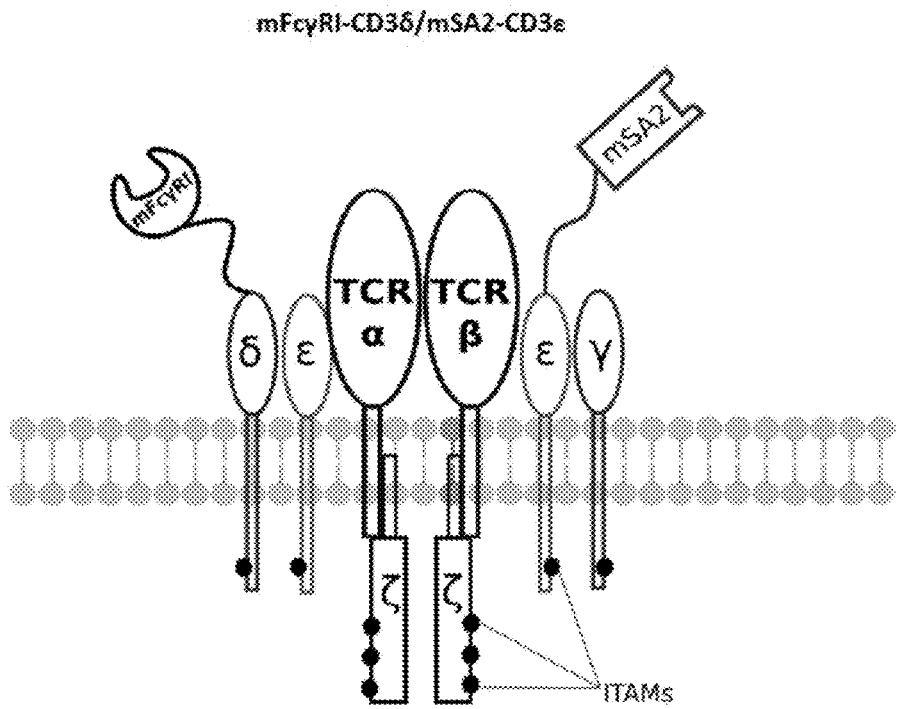
Figure 61:
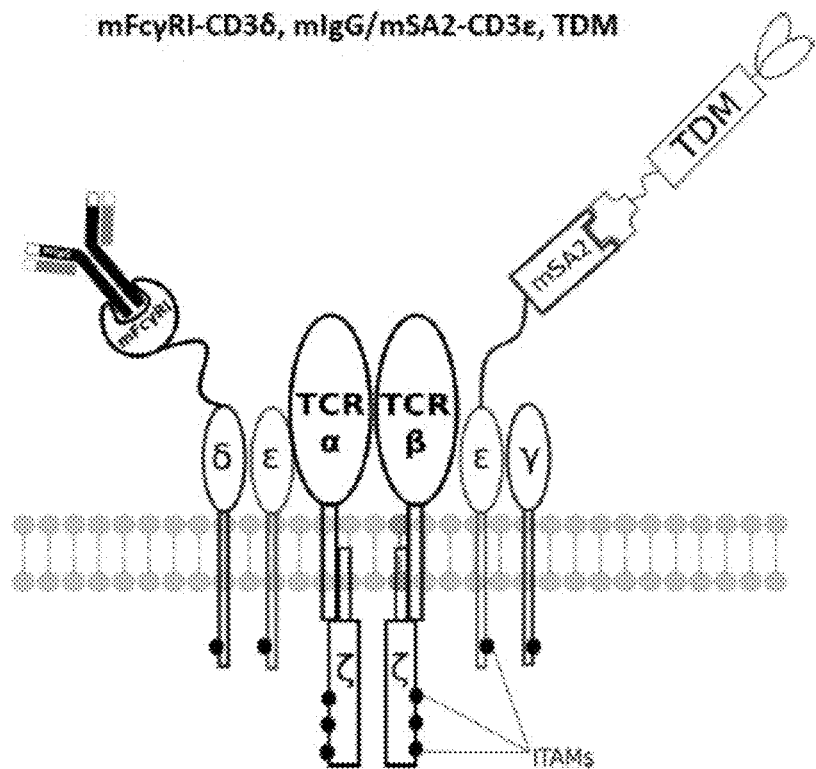
Figure 62:
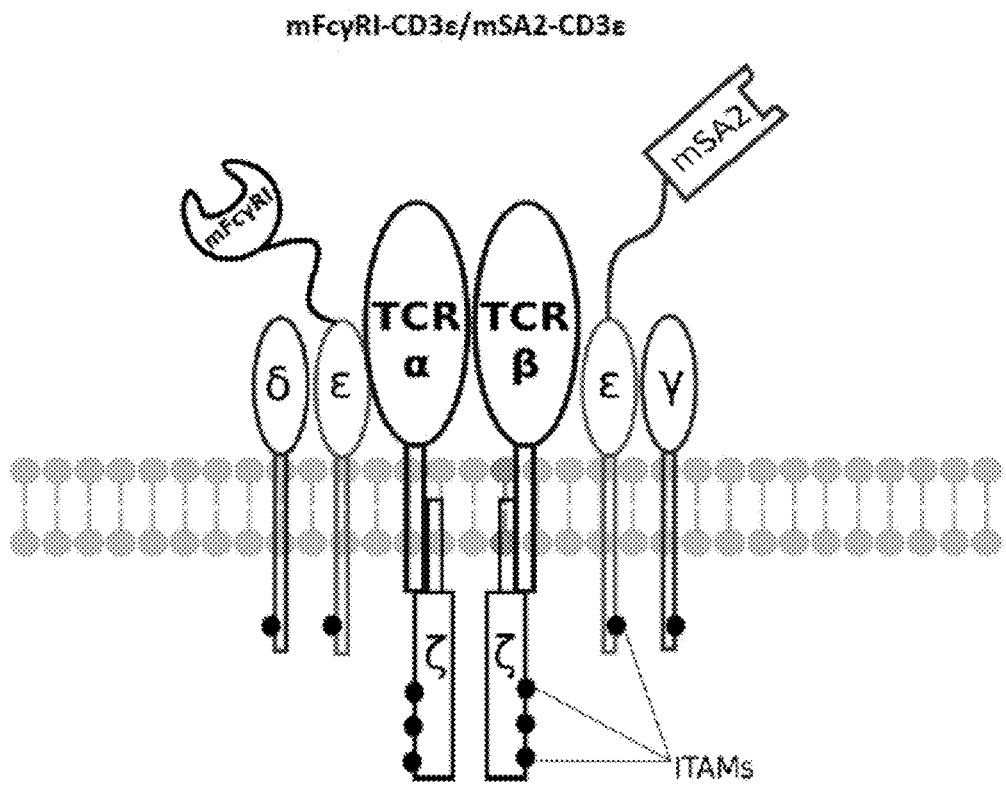
Figure 63:
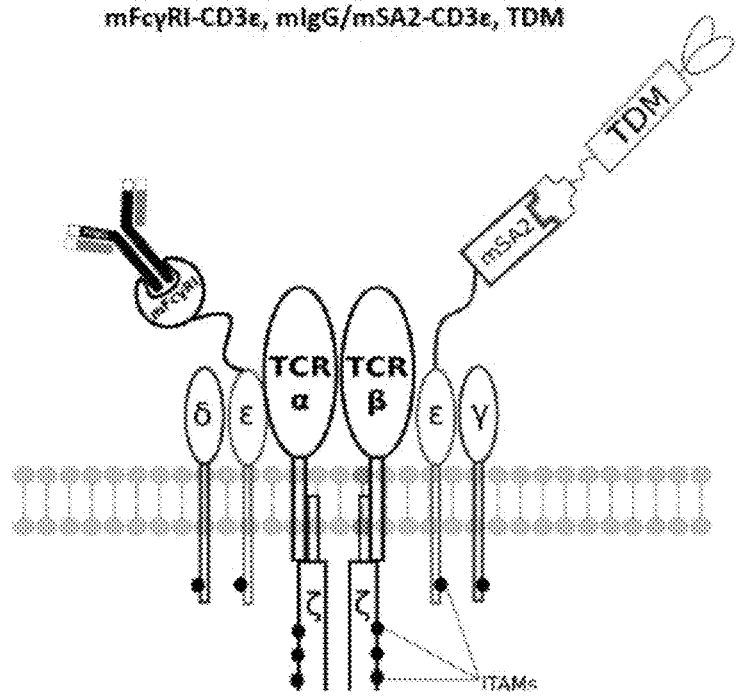
Figure 64:
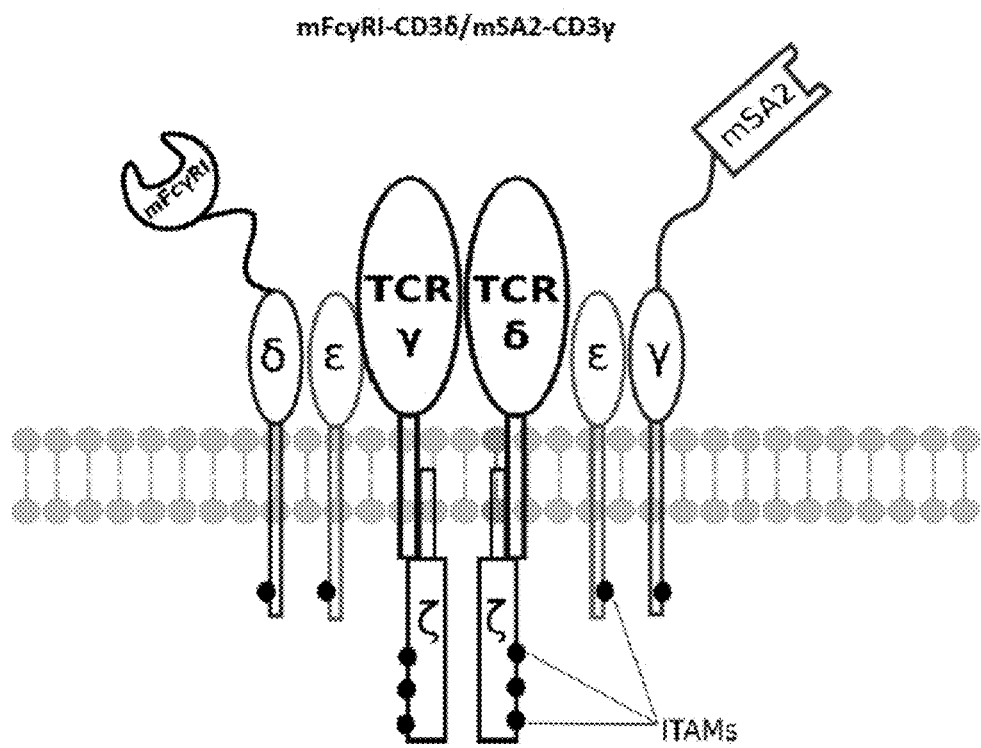
Figure 96:
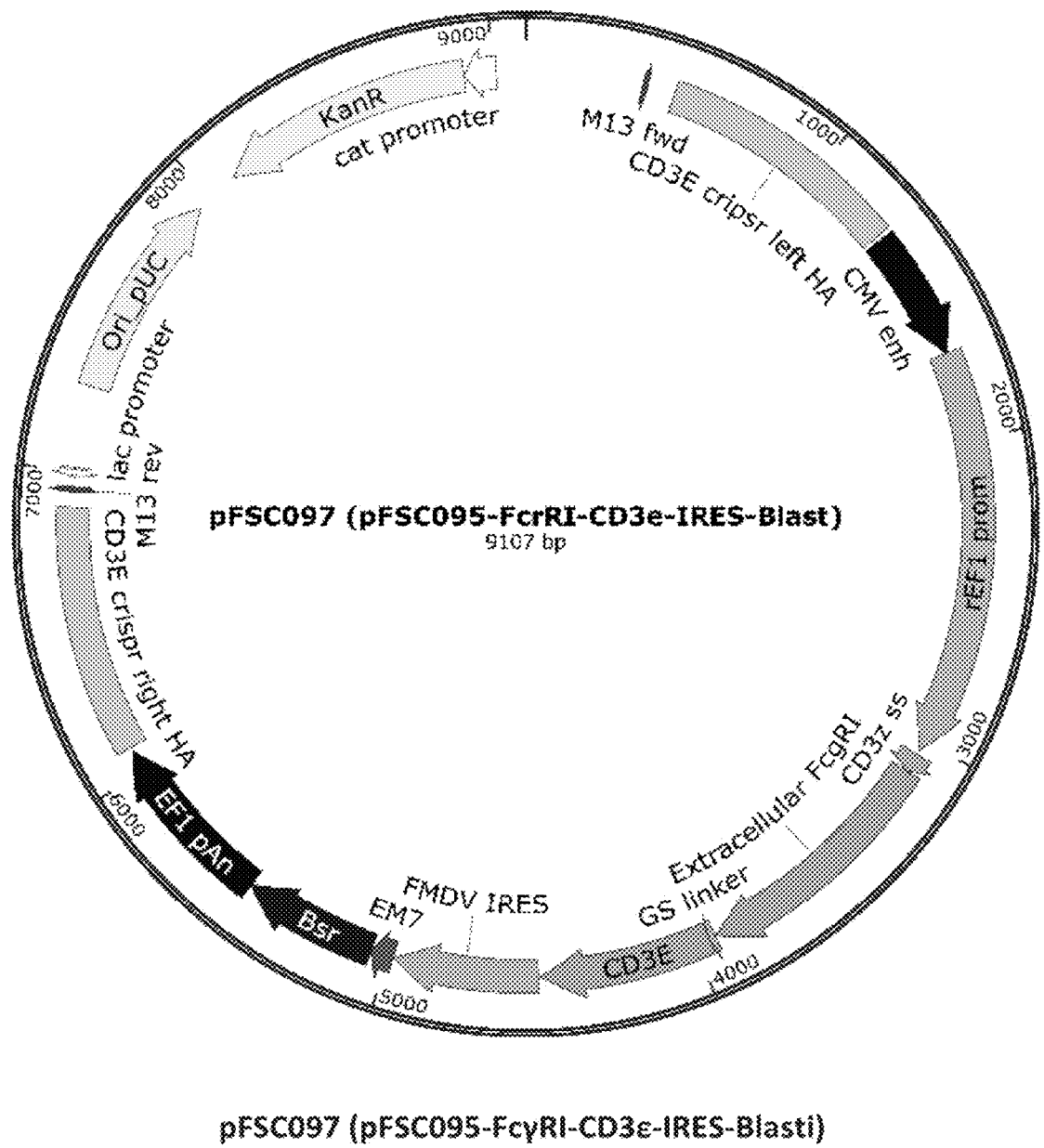
FIG. 96 is an illustration of plasmid pFSC097 (pFSC095-FcγRI-CD3ε-IRES-Blasti)
Figure 97:
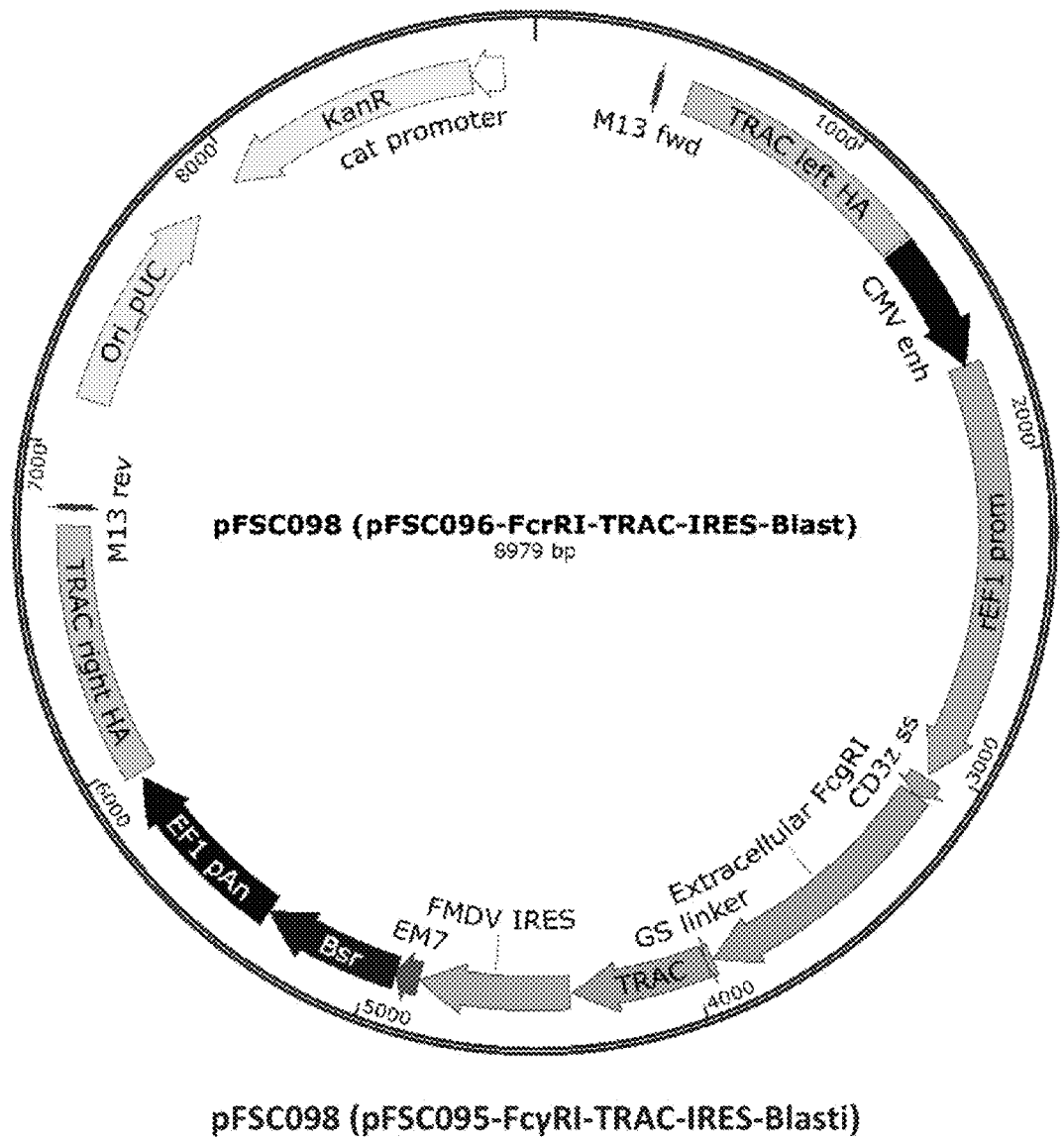
FIG. 97 is an illustration of plasmid pFSC098 (pFSC095-FcγRI-TRAC-IRES-Blasti)
Figure 98:
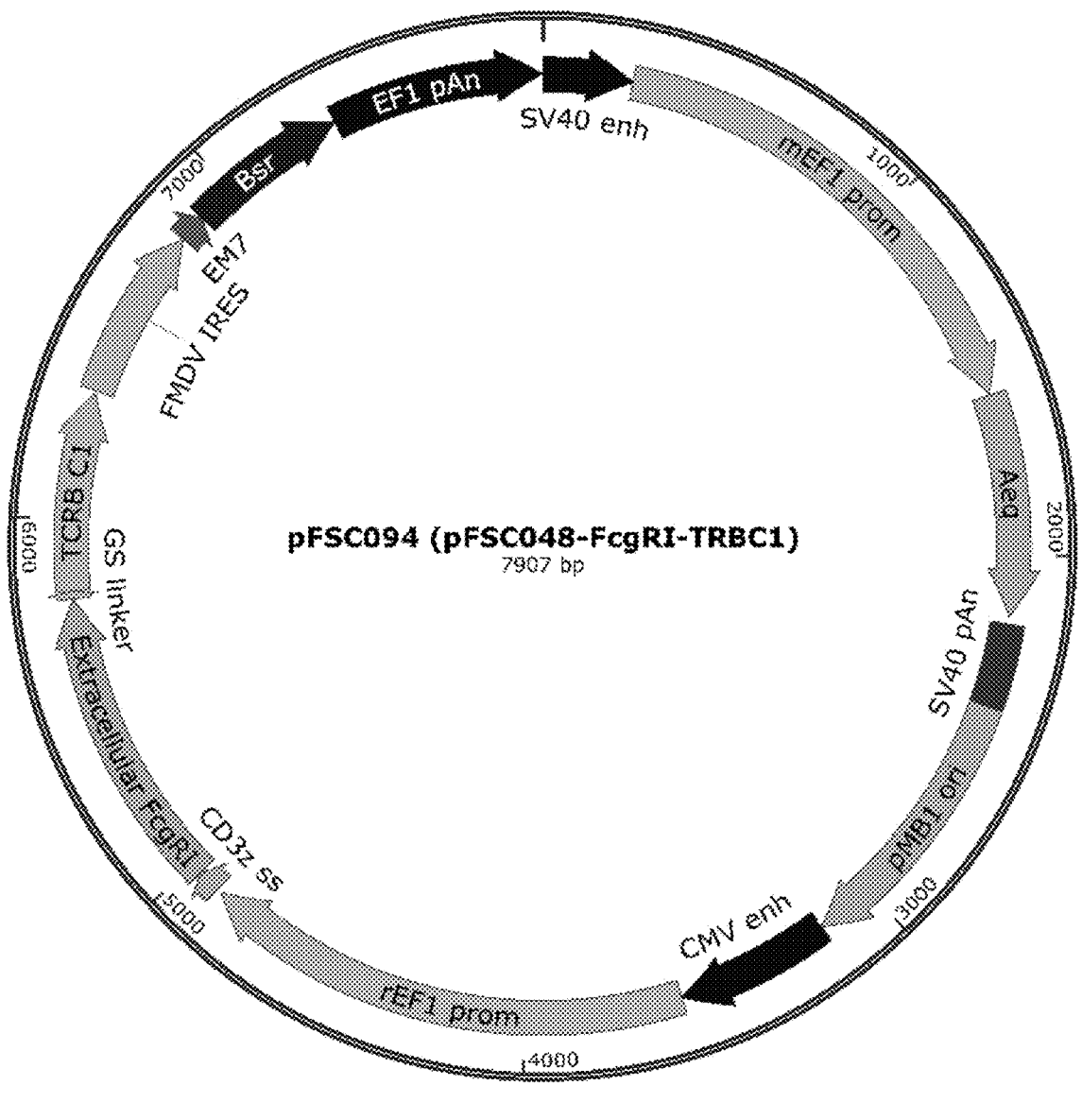
FIG. 98 is an illustration of plasmid pFSC094 (pFSC048-FcγRI-TRBC1-IRES-Blasti)
Figure 99:
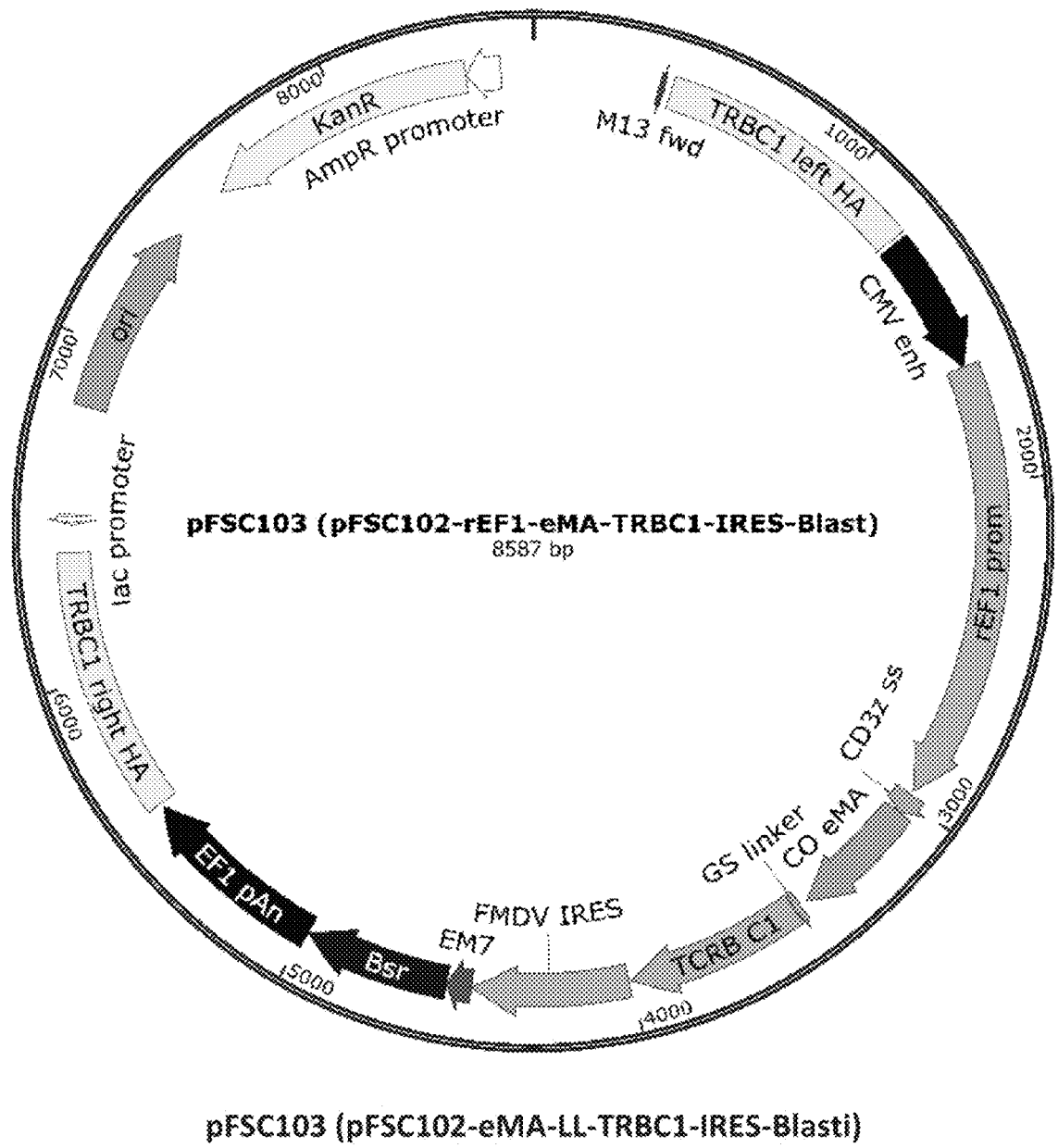
FIG. 99 is an illustration of plasmid pFSC103 (pFSC102-eMA-LL-TRBC1-IRES-Blasti)
Figure 100:
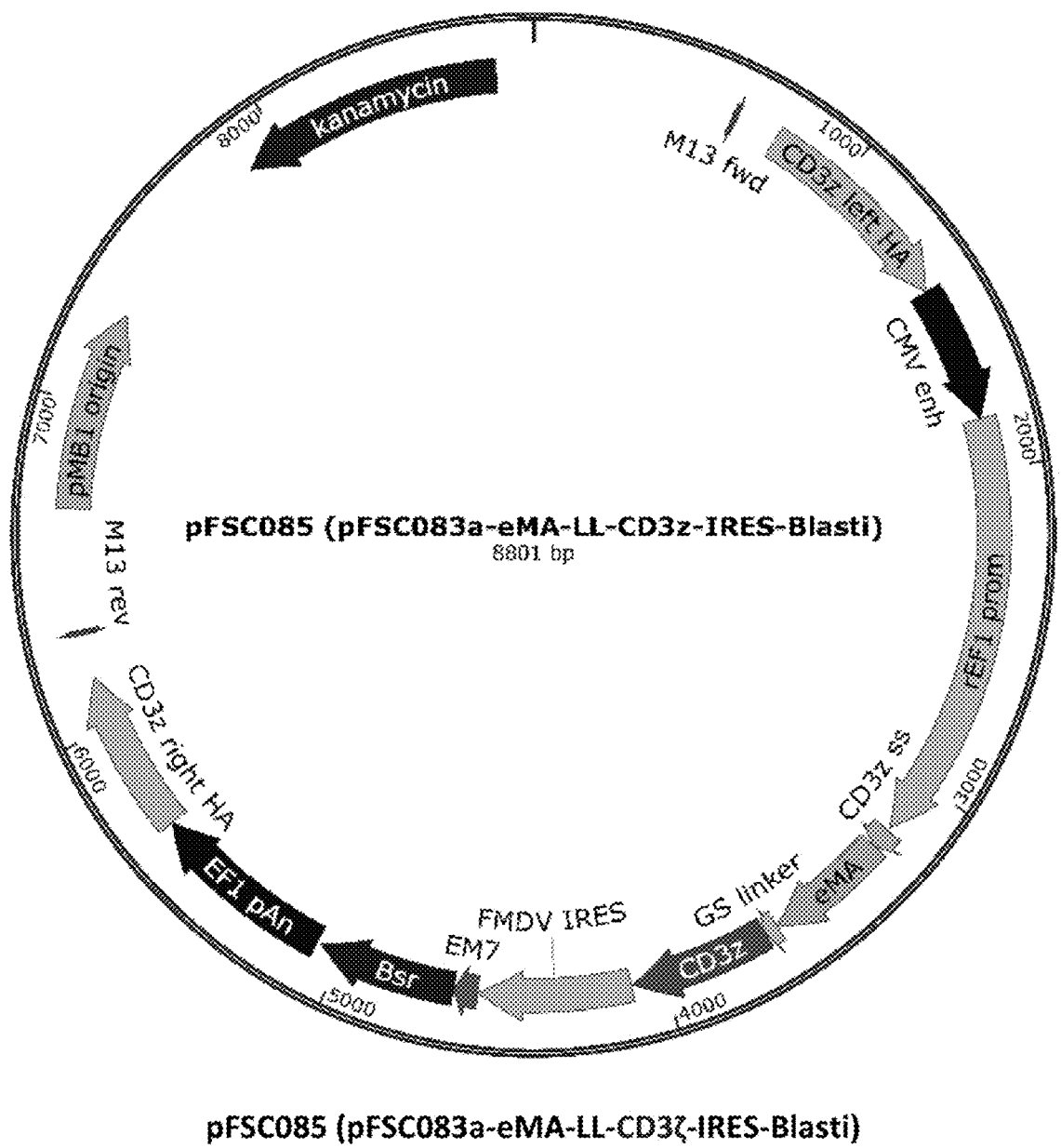
FIG. 100 is an illustration of plasmid pFSC085 (pFSC083a-eMA-LL-CD3ζ-IRES-Blasti)
Figure 101A:
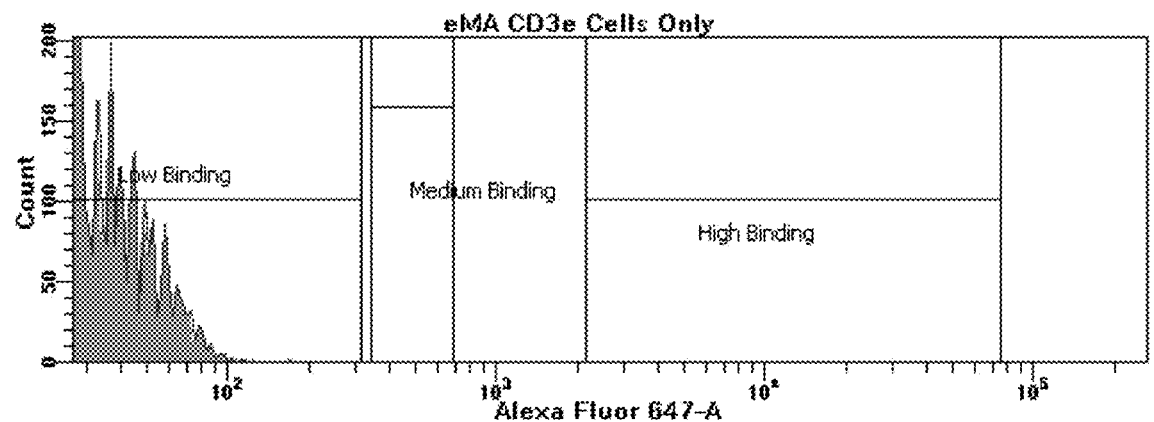
FIGS. 101A-101C are flow cytometry plots comparing expression levels of the eMA-CD3ε receptor in unstained, negative, and stained samples of eMA-CD3ε cells.
Figure 101B:
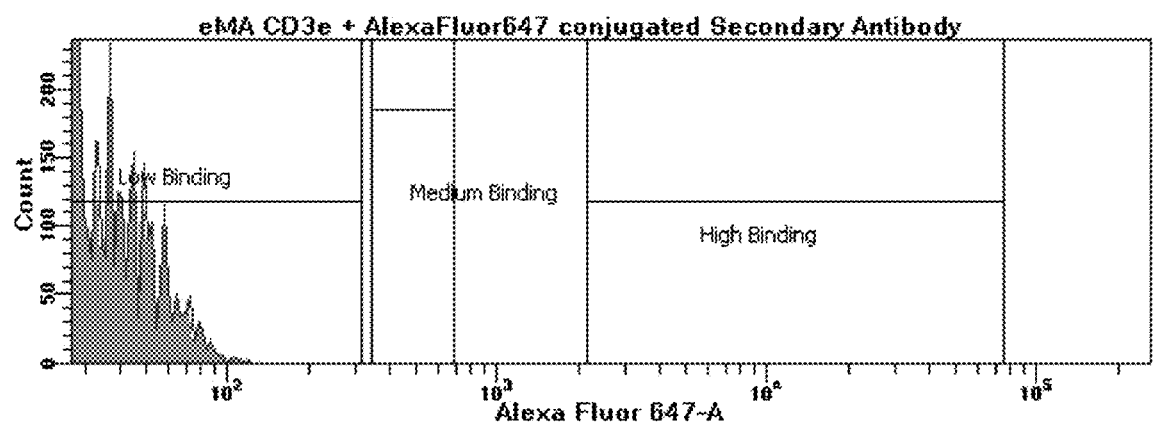
Figure 101C:
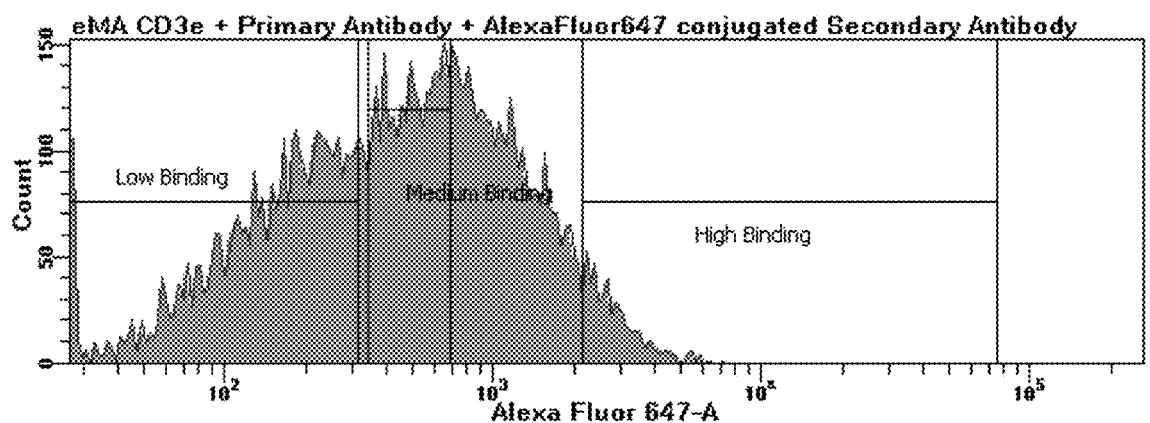

Additional plasmids were used to construct various embodiments and variants of the present invention. Plasmid pFSC097 (pFSC095-FcγRI-CD3ε-IRES-Blasti) as shown in FIG. 96 was used for constructing mFcγRI-CD3ε as illustrated in FIG. 6 and FIG. 8. SEQ ID NO. 9 provides the DNA sequence for CD3ζSS-FcγRI-CD3ε and SEQ ID NO. 10 provides the amino acid sequence for CD3ζSS-FcγRI-CD3ε. Plasmid pFSC098 (pFSC095-FcγRI-TRAC-IRES-Blasti) as shown in FIG. 97 was used for constructing mFcγRI-TRAC as illustrated in FIG. 20. SEQ ID NO. 11 provides the DNA sequence for CD3ζSS-FcγRI-TRAC and SEQ ID NO. 12 provides the amino acid sequence for CD3ζSS-FcγRI-TRAC. Plasmid pFSC094 (pFSC048-FcγRI-TRBC1-IRES-Blasti) as shown in FIG. 98 was used for constructing mFcγRI-TRBC1 as illustrated in FIG. 22. SEQ ID NO. 13 provides the DNA sequence for CD3ζSS-FcγRI-TRBC1 and SEQ ID NO. 14 provides the amino acid sequence for CD3ζSS-FcγRI-TRBC1. Plasmid pFSC103 (pFSC102-eMA-LL-TRBC1-IRES-Blasti) as shown in FIG. 99 was used for constructing eMA-TRBC1 as illustrated in FIG. 52. SEQ ID NO. 15 provides the DNA sequence for CD3ζSS-eMA-TRBC1 and SEQ ID NO. 16 provides the amino acid sequence for CD3ζSS-eMA-TRBC1. Plasmid pFSC085 (pFSC083a-eMA-LL-CD3ζ-IRES-Blasti) as shown in FIG. 100 was also used to construct certain embodiments and variants of this invention. SEQ ID NO. 17 provides the DNA sequence for CD3ζSS-eMA-CD3ζ and SEQ ID NO. 18 provides the amino acid sequence for CD3ζSS-eMA-CD3ζ.

Choice of Cells and Source

The programmable immunocyte receptor complex of the present invention is useful for therapeutics, pre-testing of therapeutics and diagnostics. The receptor complex may be genetically engineered in different human immune cells including, but not limited to; T cells, B cells, dendritic cells, macrophages and natural killer cells. These cells are either primary cells (for therapeutics and diagnostics) or immortalized cells (for diagnostics). Because the system is designed for both diagnostics, therapeutics and companion diagnostics, the functionality and performance of the engineered cells will be tested against a cocktail of TDMs. In an exemplary embodiment of this invention, Jurkat cells (Clone E61, ATCC® TIB152™) have been engineered to generate a modified TCR complex that expresses the universal or programmable receptor, eMA-CD3ε. These cells have been used to demonstrate target-induced cell activation, cytokine release, and to perform biotin inhibition assays. Another embodiment of this invention includes engineered cells that simultaneously express the universal/programmable receptor and Aequorin, a calcium-activatable photoprotein from jellyfish (*Aequorea victoria*). This embodiment is particularly useful for diagnostic applications, wherein the engineered cells function as biosensors for pathogen detection. Two primary T cells (CD4+ and CD8+) have also been engineered to express the universal/programmable receptor, eMA-CD3ε. The resultant adaptive TCR complex cells are useful for cell activation studies, target cell lysis, and expression of activation markers. Other immune cells can be engineered to express the universal, adaptable receptors of the present invention. Immune cells can also be selected from non-human animals. This process may be accomplished through modification of the cell's own receptors, but in certain instances it will involve receptor mobility (transfer of receptor components from one cell to another). For therapeutic applications, autologous, syngeneic or allogeneic primary cells will be harvested from individuals, activated, isolated and genetically engineered to generate universal/programmable/adaptive receptor-expressing cells and then infused into the patient. The present invention also includes a safe and effective freezing process for the engineered cells to allow flexibility in the treatment process.

Gene Delivery and Editing

Transient and stable gene expression methods have been utilized with the present invention. Gene constructs have been delivered by electroporation of either linear or circular plasmids depending on the desired mode of expression. Other gene constructs have been delivered through transduction using the Lentiviral system. Gene constructs have also been delivered into cells through lipofection. Site-specific incorporation of genes has been accomplished through the CRISPR/Cas9 technology, but other nuclease technologies such as TALE Nucleases, Zinc-Finger nucleases and Meganucleases may be utilized. In addition, RNA delivery methods may also be used. Gene expressing cells have been enriched through cell sorting (clonal line development) and by antibiotic selection. However, antibiotic selection is typically only used for diagnostic-based cells because antibiotic resistance genes are not desirable for therapeutic cells.

Transfection

For DNA linearization and purification, maxi preps of plasmid DNA pFSC086a, containing the rEF1-mSA2-CD3ζ-IRES-Blasti CRISPR construct; pFSC100a, containing the rEF1-eMA-LL-CD3ε-IRES-Blasti CRISPR construct and pFSC005, containing the EF-1α-Aeq construct for Aequorin expression were prepared using the Qiagen Qia- Filter Plasmid Midi and Maxi Kit. The plasmid DNA was then linearized by restriction enzyme digestion to increase the efficiency of chromosomal integration into Jurkat cells. Plasmid pFSC086a and pFSC005 were linearized by restriction enzyme digestion with SspI while plasmid pFSC100a was linearized by restriction enzyme digestion with ApaLI. The linearized plasmid DNA was purified using the Promega Wizard® SV Gel and PCR Clean-up Kit in preparation for transfection into MF Jurkat/pEF1-Aeq cells. Quality control checks were conducted on the linearized, purified construct plasmids by running each linearized sample and an un-linearized control sample on a 0.8% agarose gel and analyzing by way of gel electrophoresis to confirm the correct DNA band size for each plasmid.

For generation of aequorin expressing platform cells (MF Jurkat/pEF1-Aeq Platform Cells), Jurkat cells were obtained from ATCC and cultured following ATCC guidelines. Transfections of purified linear pFSC005 into Jurkat cells were performed following the Lonza Amaxa® Cell Line Nucleofector® Kit V optimized transfection protocol for Jurkat, Clone E6-1 cells. The transfections were performed with 4 µg of linearized DNA, using Lonza Program X-005 for maximum transfection efficiency. After transfection, cells were incubated in a 12 well plate at room temperature for 20 minutes before addition of culture medium. The day after transfection, the cells were centrifuged at 150 RCF for 8 minutes, the supernatant was removed, and the cell pellet was re-suspended in 3 mL RPMI 1640, 10% FBS, 1× Pen/Strep and transferred to a 6 well plate to start culturing. The Jurkat/pEF1-Aeq cells were cultured and expanded to 30 mL in RPMI 1640, 10% FBS, 1× Pen/Strep for 1 week until the cell viability exceeded 90%. G418 was then added to a concentration of 0.5 mg/mL to select for cells with chromosomal integration of the pEF1-Aeq gene construct. Jurkat/pEF1-Aeq cells were cultured under G418 selection for 2-3 weeks until cell viability recovered to at least 90%.

For generation of eMA-CD3ε and mSA2-CD3ζ expressing cells, each linearized plasmid DNA (pFSC100a and pFSC086a) and the corresponding CRISPR guide RNA plasmids were co-transfected into MF Jurkat/pEF1-Aeq cells following the Lonza Amaxa® Cell Line Nucleofector® Kit V optimized transfection protocol for Jurkat, Clone E6-1 cells. Transfections were performed using Lonza Program X-005 with 2 µg of linearized construct plasmid and 2 µg of CRISPR guide RNA plasmid added per transfection. Transfected cells were transferred from the cuvette to a 12 well plate and allowed to incubate at room temperature for 20 minutes before adding culture medium. The day after transfection, cells were centrifuged at 150 RCF for 8 minutes, the supernatant was removed, and the cell pellet was re-suspended in 3 mL RPMI 1640, 10% FBS, 1× Pen/Strep and transferred to a 6 well plate. Transfected cells were then cultured at 37° C. with either 5% or 8% $CO_2$.

Selection, Verification and Preservation of Transfected Cells

For selection and enrichment of transfected cells, following transfection, the MF Jurkat/pEF1-Aeq/rEF1-mSA2-CD3ζ CRISPR cell line (hereinafter, mSA2-CD3ζ) and MF Jurkat/pEF1-Aeq/rEF1-eMA-LL-CD3ε-IRES-Blasti CRISPR cell line (hereinafter, eMA-CD3ε) were cultured and gradually expanded to a volume of 30 mL and cultured in RPMI 1640, 10% FBS, 1× Pen/Strep for approximately 1 week until the cell viability exceeded 90%. Blasticidin was then added to a final concentration of 3 µg/mL to select for cells with chromosomal integration of the rEF1-mSA2-CD3ζIRES-Blasti or rEF1-eMA-LL-CD3ε-IRES-Blasti CRISPR constructs. Cells were cultured in RPMI 10% FBS, 1× Pen/Strep, 3 µg/mL Blasticidin for 2-3 weeks to allow selection to occur and cell viability to recover to at least 90% before verification tests were performed. Clonal lines were generated through single cell sorting on a Flow Cytometer.
Verification of Transfected Cells For verification by PCR, genomic DNA was extracted from mixed populations of eMA-CD3ε and mSA2-CD3ζ cells using the Qiagen DNeasy® Blood & Tissue Kit. PCR was performed on the extracted genomic DNA using primers targeting the insertion junctions for each construct to confirm the correct chromosomal integration into the predetermined genomic locations.

For verification by flow cytometry, the eMA-CD3ε cells were analyzed by flow cytometry to assess the level of receptor expression. Cells were counted by Trypan blue staining and aliquoted into samples of $2 \times 10^6$ cells. Each sample was resuspended in biotin-free DMEM and incubated with a final concentration of 5.2 µg/mL Streptavidin for 30 minutes at room temperature to remove any excess biotin present in the culture medium or bound to the eMA receptor. The samples were washed with DMEM to remove Streptavidin before resuspending in 100 µL of DMEM 2% BSA. The stained sample was incubated with 1.5 µg of primary antibody, biotinylated mouse anti-goat IgG then allowed to bind to the eMA receptor for 30 minutes. After incubation with the primary antibody, the negative and stained samples were stained with 1.5 µg of secondary antibody, Alexa Fluor 647 goat anti-mouse IgG and allowed to bind to the primary antibody. The stained samples were analyzed for receptor expression using flow cytometry and compared to unstained and negative control samples. This experiment was repeated to verify the expression of the mSA2 receptor in mSA2-CD3ζ cells. FIG. 100A-100C are flow cytometry plots comparing expression levels of the eMA-CD3ε receptor in unstained, negative, and stained samples of eMA-CD3ε cells; FIG. 100A is the unstained sample; FIG. 100B is the secondary Ab alone; and FIG. 100C is the primary Ab plus the secondary Ab. The stained sample was stained with biotinylated mouse anti-goat IgG+ AlexaFluor647 goat anti-mouse IgG. The negative sample was stained with AlexaFluor647 goat anti-mouse IgG only to account for non-specific binding of the secondary antibody.

For verification by cell activation assay, because the two cell lines, eMA-CD3ε and mSA2-CD3ζ were also engineered to express Aequorin, they were incubated with Coelenterazine-h for 24 hours (charging) and then tested to determine whether the mSA2 and eMA receptors would successfully bind biotinylated antibodies. Addition of biotinylated antibodies and target antigens caused receptor aggregation that activated the signal transduction pathway resulting in an Aequorin light signal that was detected in a luminometer (see FIG. 102).

Demonstration of Adaptor TCR Complex Cell Functionality and Performance

The functionality and performance of the eMA-CD3ε programmable immunocyte receptor complex was demonstrated by the experiments described below.

Figure 102:
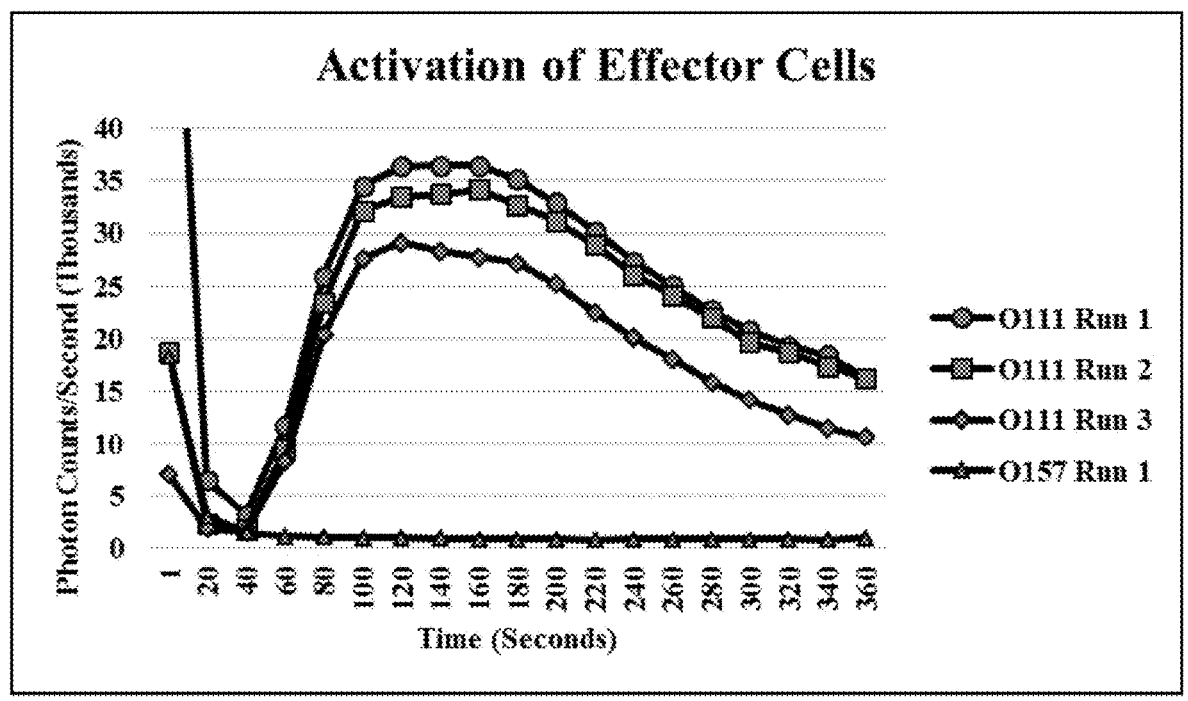
FIG. 102 is a graph showing the activation of charged eMA-CD3ε cells using *E. coli* O111 LPS and biotinylated mouse mAb against *E. coli* O111 LPS, wherein the negative control was *E. coli* O157 LPS, a non-specific antigen.

Cell Activation Assay: eMA-CD3ε cells were genetically engineered to express Aequorin, a calcium activatable photoprotein from jellyfish (*Aequorea victoria*). The active aequorin enzyme is formed by a complex between apoaequorin (APO), oxygen, and externally infused coelenterazine in a process called "charging". To activate the "charged" cells, biotinylated target detector molecules were added to bind onto the eMA receptor. Target antigens were then added to bind to the already bound TDMs on the cell surface resulting in receptor-aggregation. This triggered a cascade of intracellular signals that resulted in the release of calcium from the endoplasmic reticulum into the cytosol. The released calcium activates the luminescent enzyme, Aequorin, which catalyzes a chemical reaction, creating a light signal that is detected by a luminometer. In this experiment, 10 µg/mL biotinylated mouse monoclonal antibody against *E. coli* O111 LPS was mixed with eMA-CD3ε effector cells (800,000 cells/90 µL RPMI) and allowed to bind for 30 minutes. *E. coli* O111 LPS (250 µg/mL) was then added to activate the cells. As a negative control, *E. coli* O157 LPS was used in a similar set up. The signal was recorded using the GloMax 20/20 Luminometer (Promega). FIG. 102 is a graph showing the activation of charged eMA-CD3ε cells using *E. coli* O111 LPS and biotinylated mouse mAb against *E. coli* O111 LPS, wherein the negative control was *E. coli* O157 LPS, a non-specific antigen that did not emit light.

Figure 103:
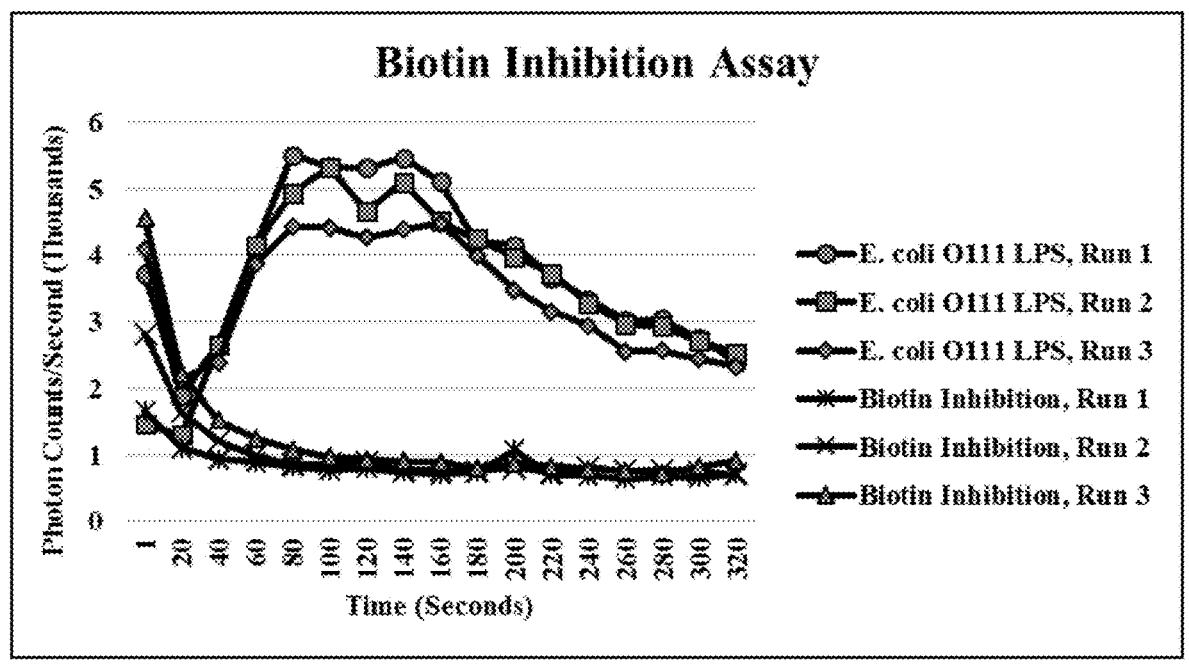
FIG. 103 is a graph showing the inhibition of eMA receptors using biotin, wherein biotin binds to the receptors and prevents biotinylated antibodies from binding.
Figure 104:
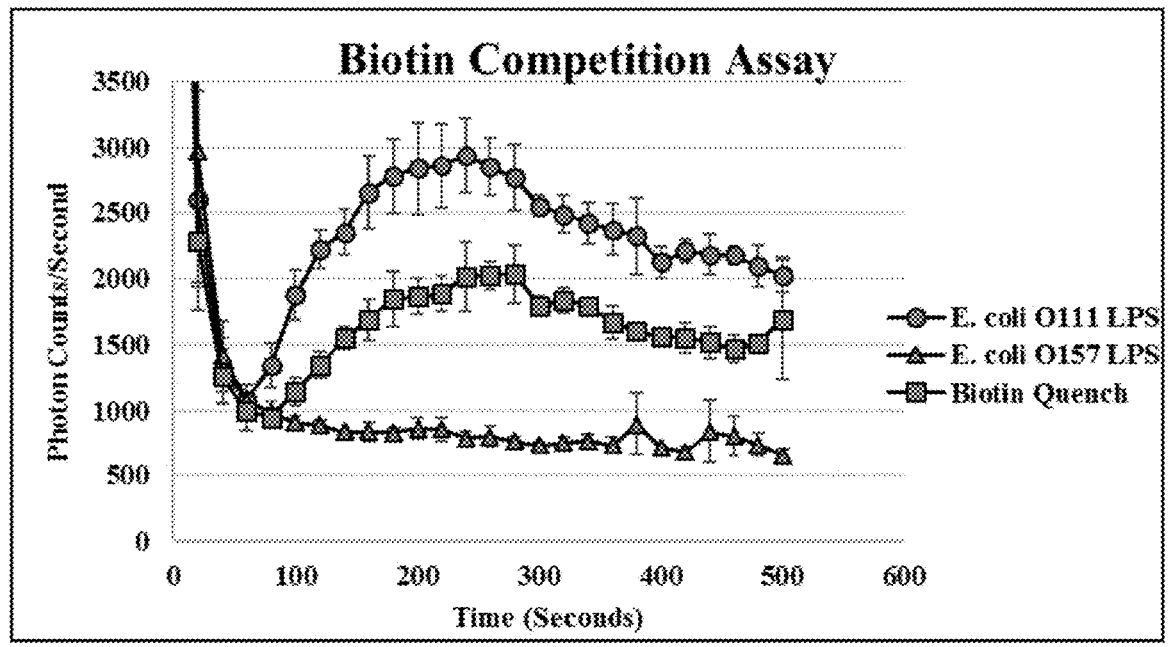
FIG. 104 is a graph showing the results of a biotin competition assay, wherein eMA-CD3ε cells were activated to emit a light signal when mixed with biotinylated mouse mAb against *E. coli* O111 LPS and *E. coli* O111 LPS.

Receptor Inhibition Assay: The receptor inhibition assay was performed on "charged" eMA-CD3ε cells by using biotin to block the eMA universal receptors on the cell surface. 13.3 µg/mL biotin was mixed with eMA-CD3ε cells (800,000 cells/90 µL RPMI) and allowed to bind the eMA receptor for 30 minutes at room temperature. A similar concentration (13.3 µg/mL) of biotinylated mouse monoclonal antibody against *E. coli* O111 LPS was then added to the mixture and allowed to incubate for 30 minutes. *E. coli* O111 LPS (250 µg/mL) was added to the mixture and the signal recorded using the GloMax 20/20 Luminometer (Promega). FIG. 103 is a graph showing the inhibition of eMA receptors using biotin, wherein biotin binds to the receptors and prevents biotinylated antibodies from binding. Blocked eMA-CD3ε cells were not activated when biotinylated antibodies and the corresponding target/pathogen were added. However, in a positive control assay, non-blocked eMA-CD3ε cells were activated.

Biotin Competition Assay: Biotin and other biotin conjugates can be used to regulate the activation of adaptor TCR complex cells. A competition assay was performed on the eMA-CD3ε cells using biotin as an "on/off" switch to regulate cell activation. The eMA-CD3ε cells were incubated with 5 µg/mL biotinylated scFv against *E. coli* O111 LPS for 30 minutes to allow scFv binding. Biotin (13.3 µg/mL) was added to the mixture and incubated at room temperature for 30 minutes before adding 250 µg/mL *E. coli* O111 LPS to activate the cells. A repeat assay was performed without adding biotin. A negative control assay was also performed without adding biotin, but using 250 µg/mL *E. coli* O157 LPS, a non-specific target. All assays were performed in triplicate and all signals recorded on the GloMax 20/20 Luminometer (Promega). FIG. 102 is a graph showing the results of a biotin competition assay, wherein eMA-CD3ε cells were activated to emit a light signal when mixed with biotinylated scFv against *E. coli* O111 LPS and *E. coli* O111 LPS. However, addition of biotin resulted in a quenched signal due to competitive binding to the eMA receptors. Addition of biotinylated scFv combined with a non-specific target (*E. coli* O157 LPS) did not activate the cells.

Figure 105:
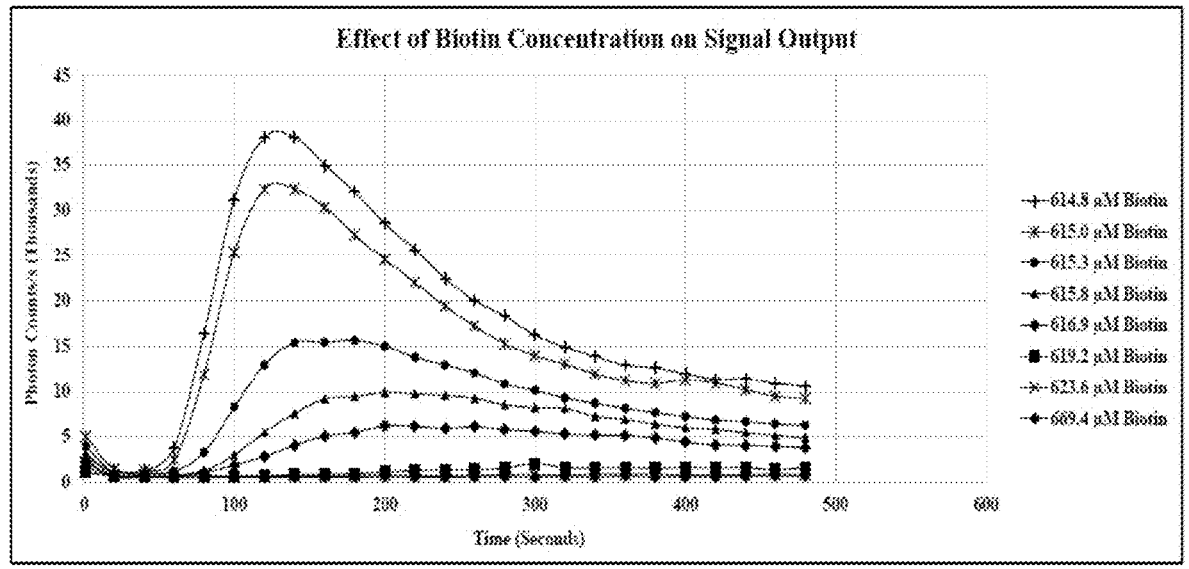
FIG. 105 is a graph showing the effect of biotin concentration on signal output, wherein the eMA receptors on eMA-CD3ε cells were inhibited by varying concentrations of biotin during cell activation where cells were activated using biotinylated mouse mAb against *E. coli* O111 LPS mixed with *E. coli* O111 LPS.

FIG. 105 is a graph illustrating that the universal receptors on eMA-CD3ε cells were inhibited by varying concentrations of biotin during cell activation. There was a correlation between biotin concentration and activation signal. Addition of biotin resulted in a quenched signal due to competitive binding to the eMA receptors. In this biotin competition assay, biotin and other biotin conjugates were used to regulate the activation of the programmable immunocyte receptor complex cells. This assay was performed on the eMA-CD3ε cells using biotinylated 1F11-IgG2a (mAb against *E. coli* O111 LPS) and *E. coli* O111 LPS. Varying concentrations of biotin were used to modulate cell activation. This experiment attempted to develop a trend between signal output and biotin concentration. 1.6 million cells/90 μL of RPMI were incubated with varying concentrations of biotin for 30 minutes. 10 μg/mL biotinylated 1F11-IgG2a was added and incubated for an additional 30 minutes. After incubation, the cells/antibody/biotin mixture was added to 250 μg/mL *E. coli* O111 LPS to trigger cell activation. The amount of biotin present in the media was high from the start so the amount of biotin added was a small increment. Results demonstrate a correlation between signal output and biotin concentration. The higher the concentration of biotin, the lower the activation signal hence biotin is a good modulator of signal activation in this invention.

Figure 112:
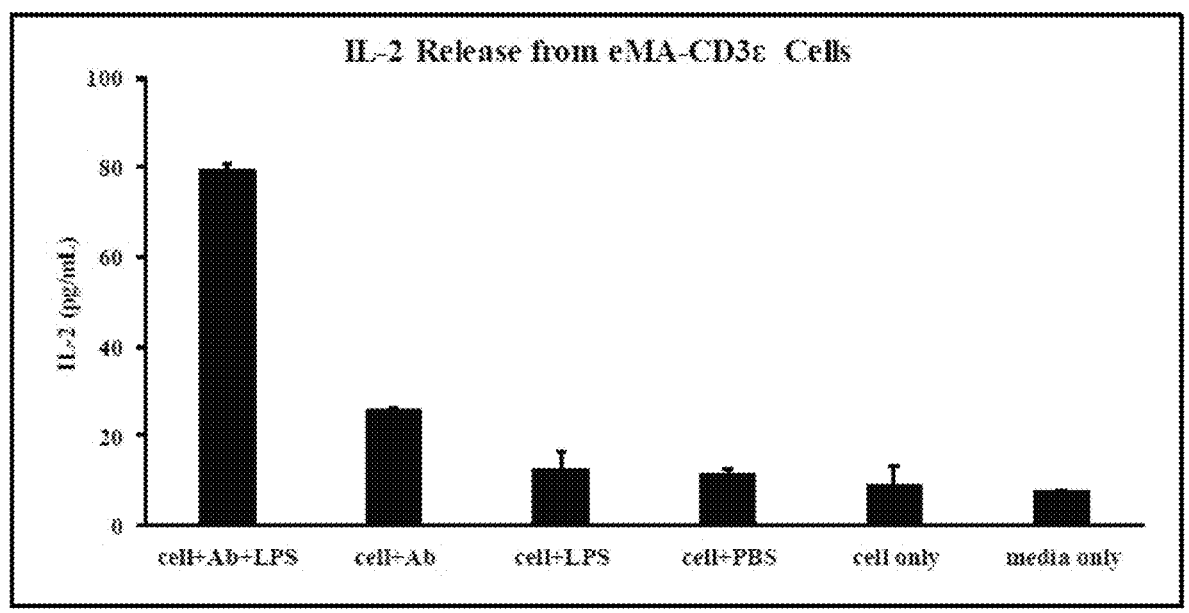
FIG. 112 is a graph showing the results of a cytokine release study (activation of eMA-CD3ε cells to release IL-2), wherein incubating cells with the biotinylated antibody against *E. coli* O111 LPS and *E. coli* O111 LPS resulted in cell activation and IL-2 release.
Figure 113:
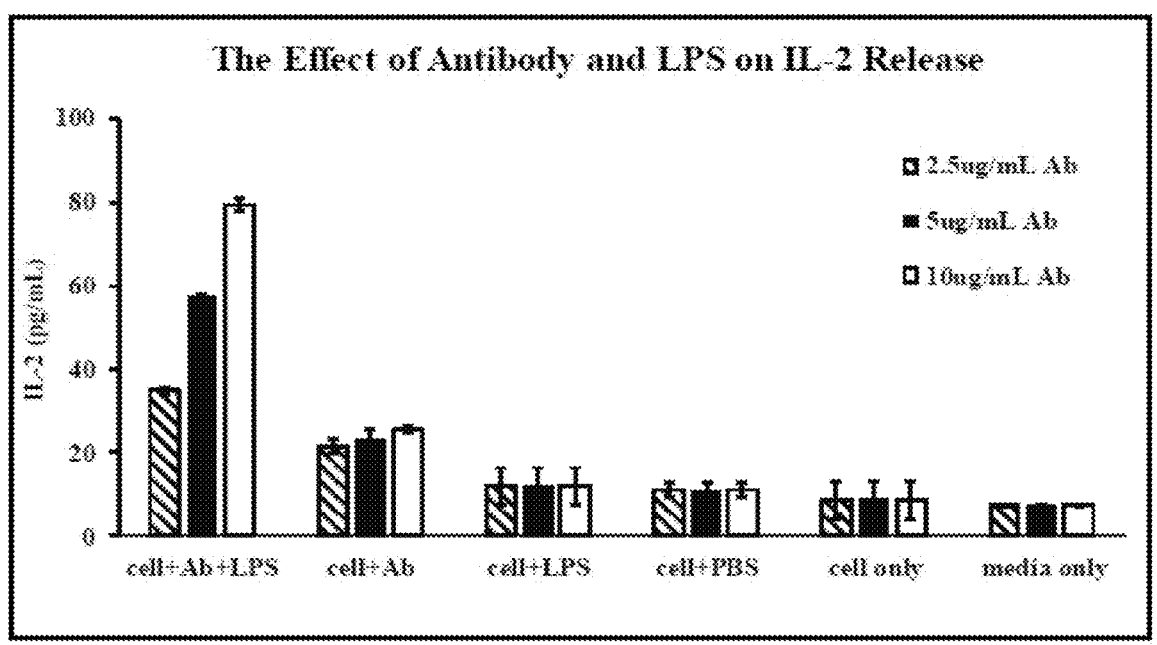
FIG. 113 is a graph showing the results of a cytokine release study (activation of eMA-CD3ε cells to release IL-2) wherein IL-2 release was shown to be antibody concentration-dependent.

Cytokine Release Study: Biotinylated target detector molecules can recognize and bind to eMA on the eMA-CD3ε cell surface. Upon introduction of their specific targets, cells are activated resulting in cytokine production. FIG. 112 is a graph showing the results of a cytokine release study (activation of eMA-CD3ε cells to release IL-2), wherein incubating cells with the biotinylated antibody against *E. coli* O111 LPS and *E. coli* O111 LPS resulted in cell activation and IL-2 release; and FIG. 113 is a graph showing the results of a cytokine release study (activation of eMA-CD3ε cells to release IL-2) wherein IL-2 release was shown to be antibody concentration-dependent. For these experiments, eMA-CD3ε cells (1×10$^6$ cells/2 mL RPMI) were mixed with 10 μg/mL biotinylated mouse monoclonal antibody (IgG2a) against *E. coli* O111 LPS and 150 μg/mL *E. coli* O111 LPS at room temperature for 30 minutes with gentle mixing every 10 minutes. Cells were then transferred to a 37° C. incubator with 5% $CO_2$ for 18 hours. The supernatant was collected and analyzed for the presence of IL-2 by ELISA. Assays were performed in triplicate and average IL-2 production was plotted with standard deviation. A similar experiment was repeated, but with different concentrations of the biotinylated antibody; 2.5 μg/mL 5 μg/mL and 10 μg/mL. Results in FIG. 112 show that eMA-CD3ε cells were activated by binding to the antibody that bound the target antigen, LPS resulting in the release IL-2. In FIG. 113, results show that IL-2 release was antibody concentration-dependent with 10 μg/mL antibody resulting in the most release.

Figure 77:
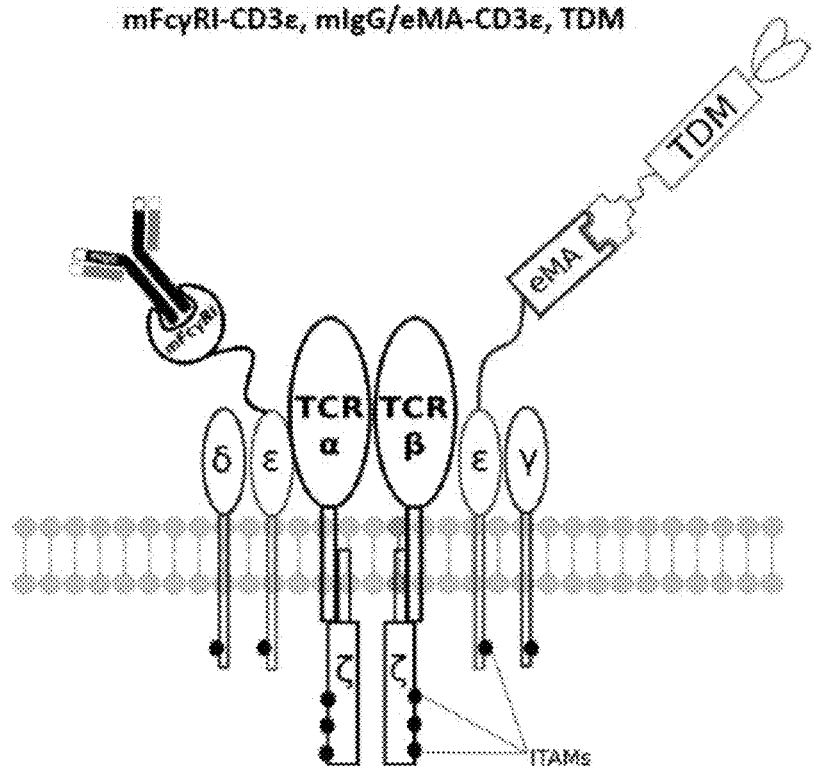
Figure 78:
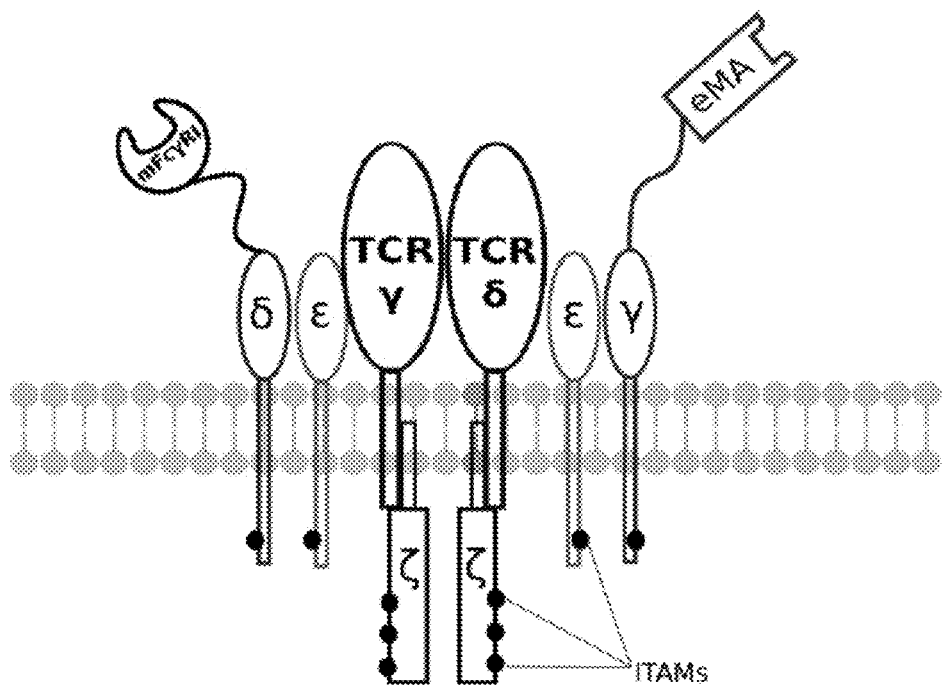
Figure 79:
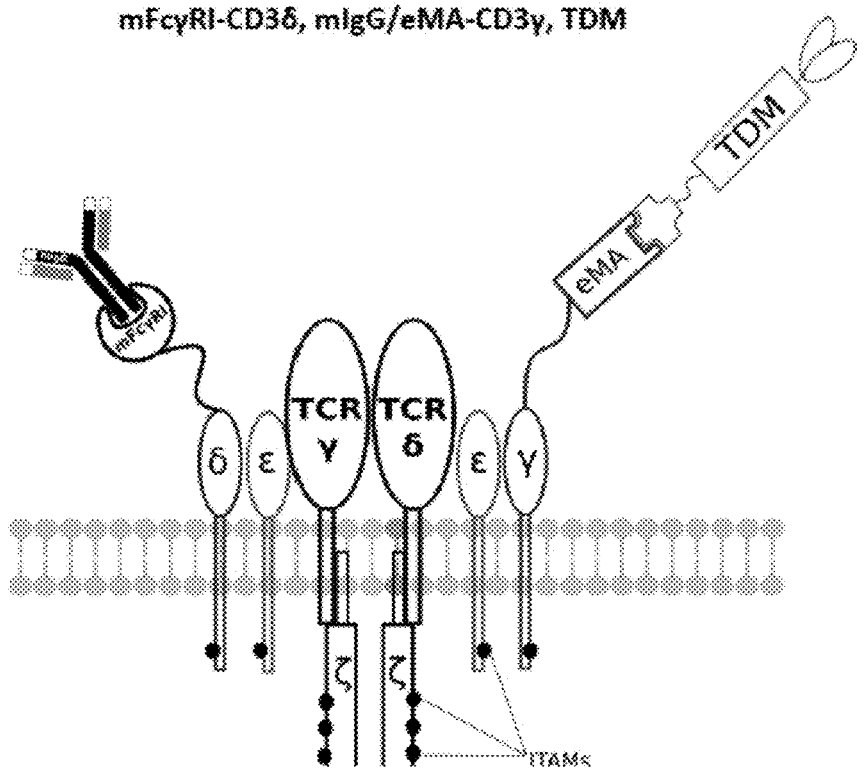
Figure 80:
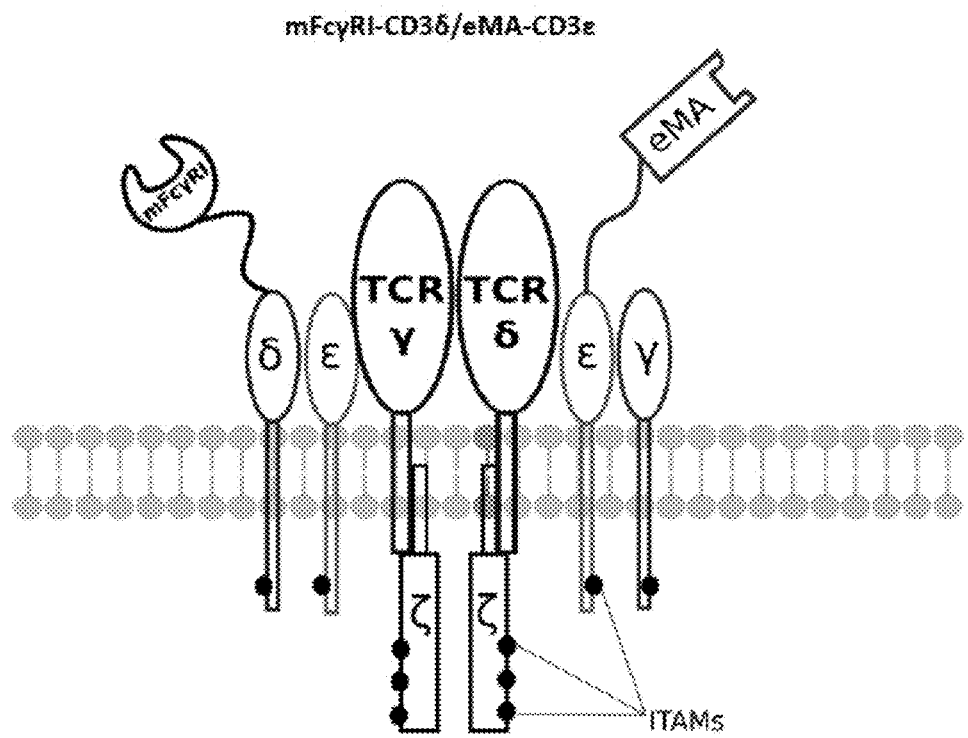
Figure 81:
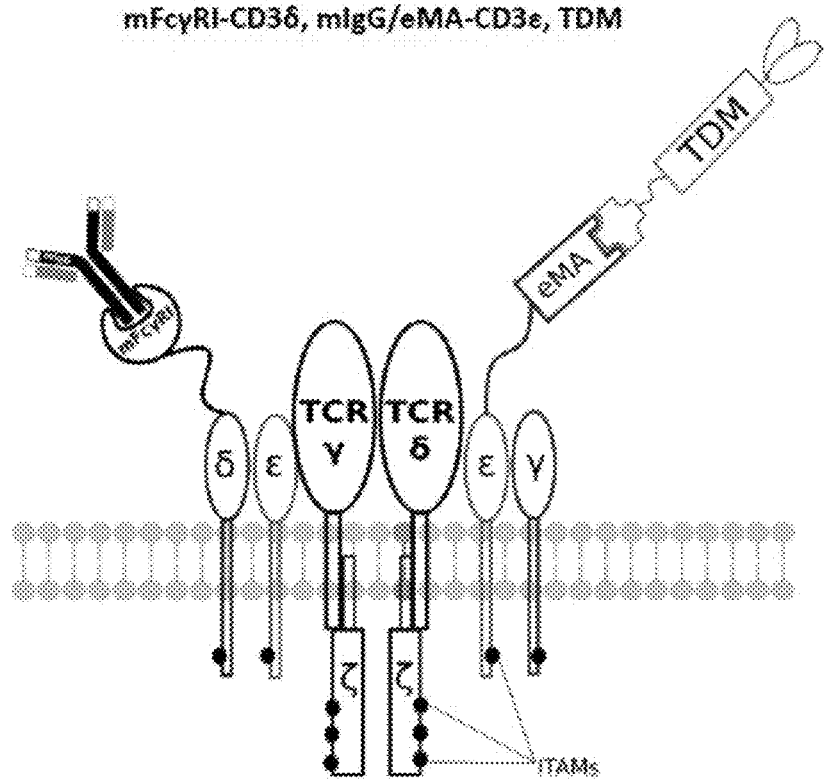
Figure 82:
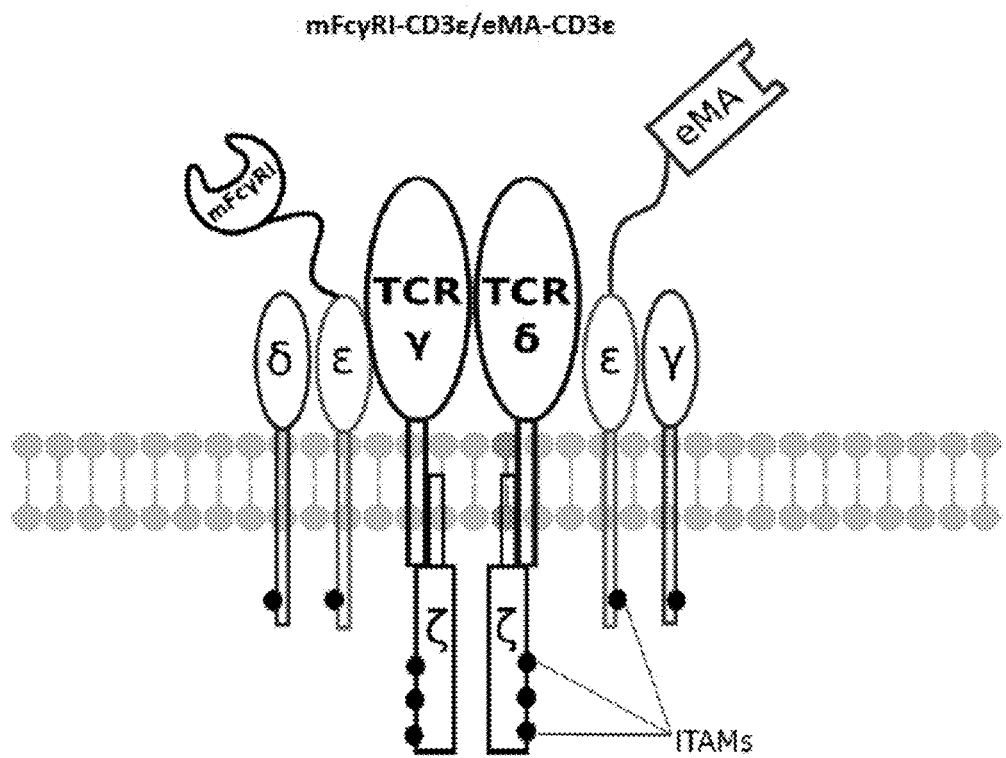
Figure 83:
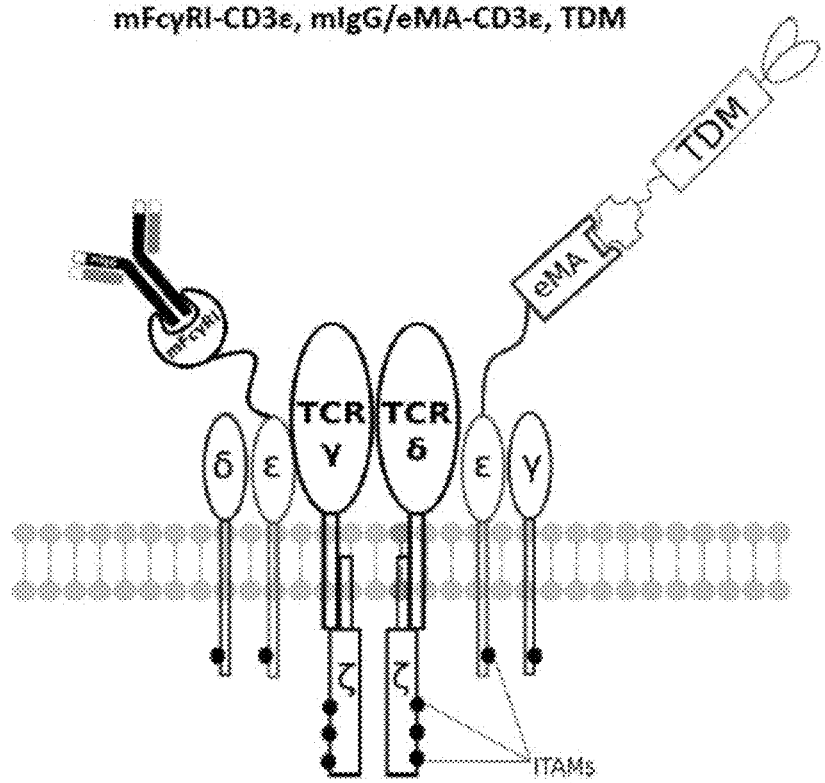
Figure 84:
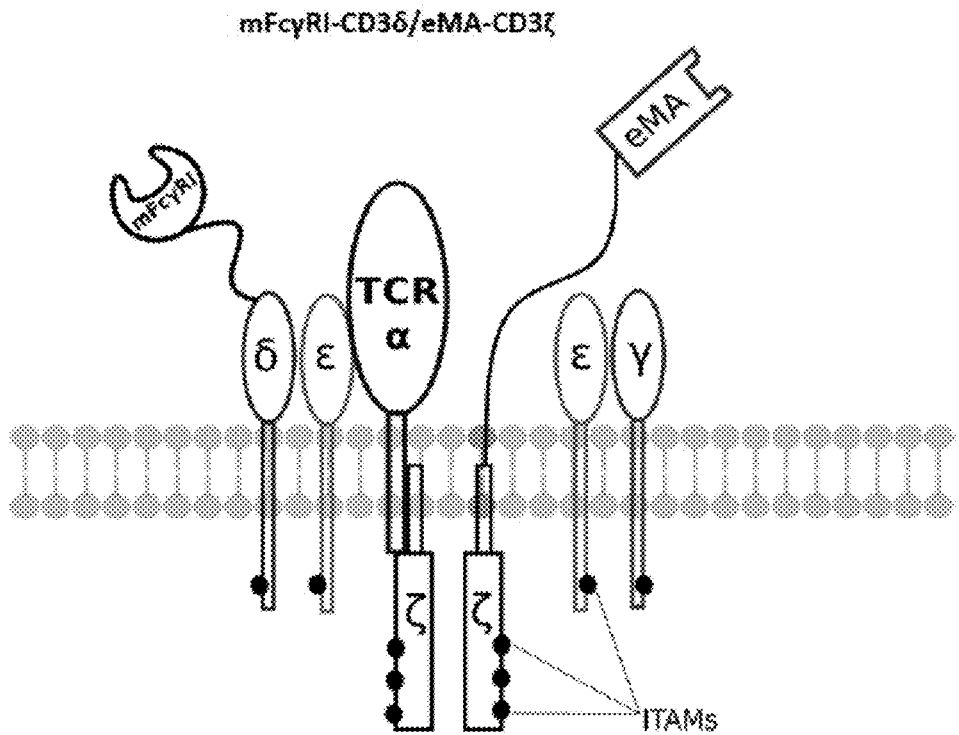
Figure 85:
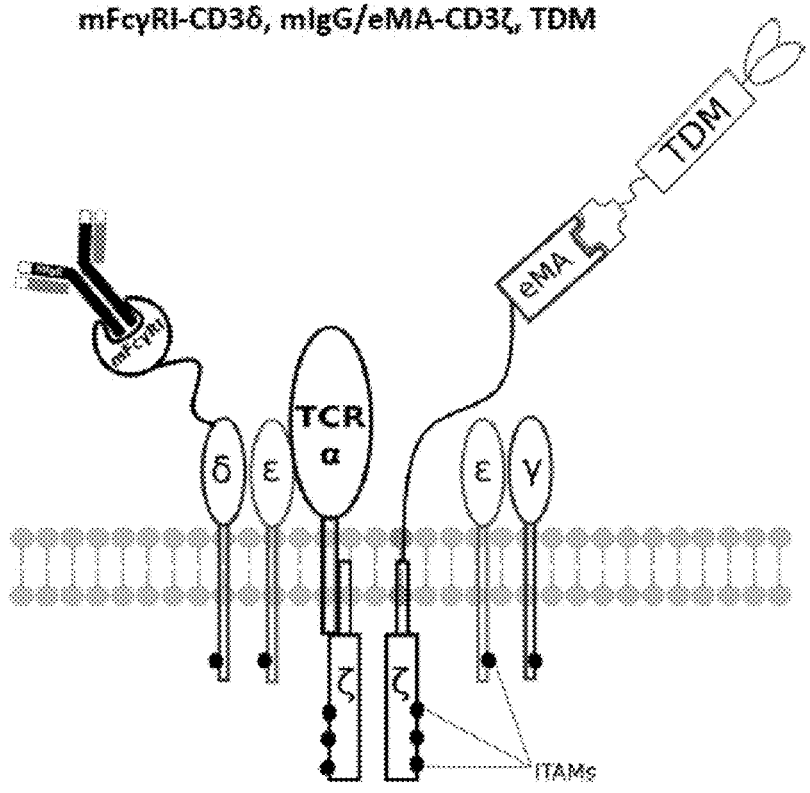
Figure 86:
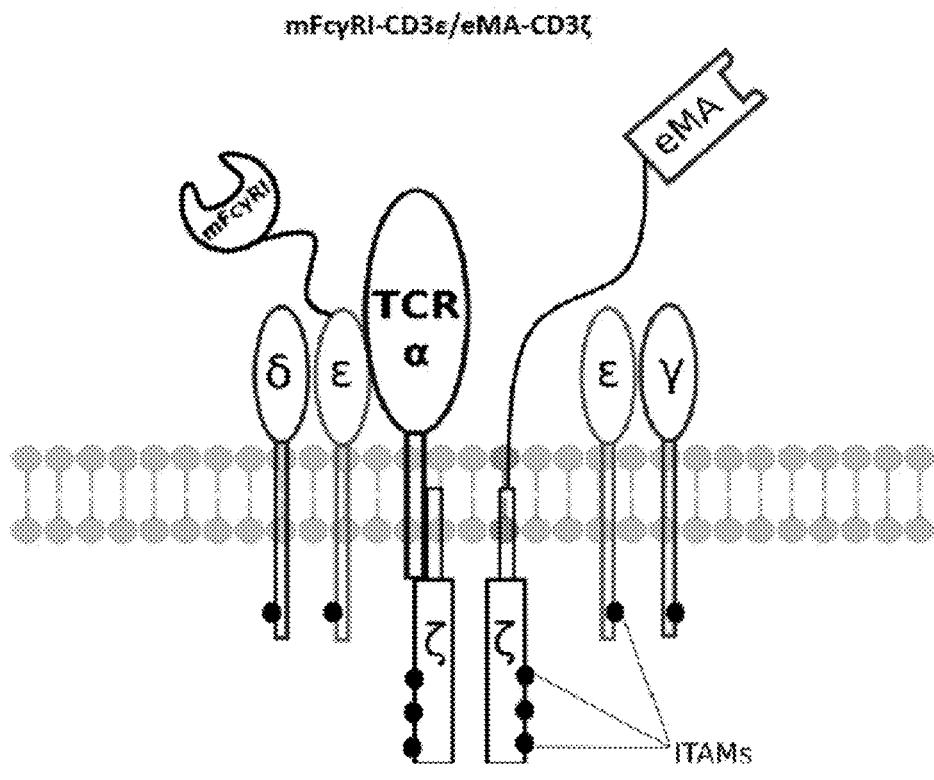
Figure 87:
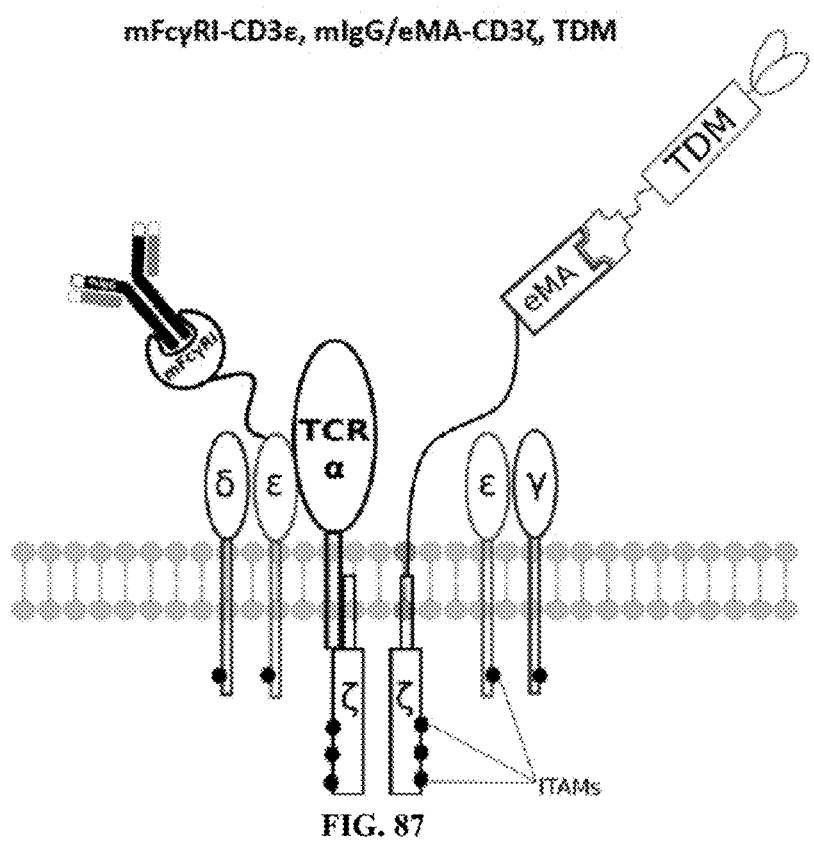
Figure 88:
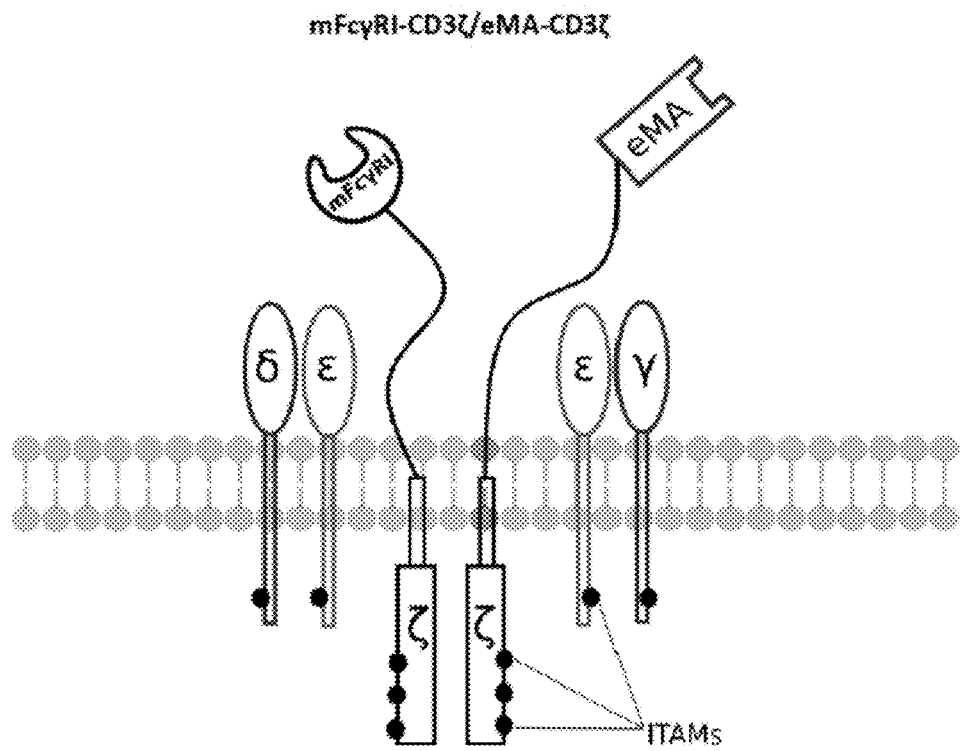
Figure 89:
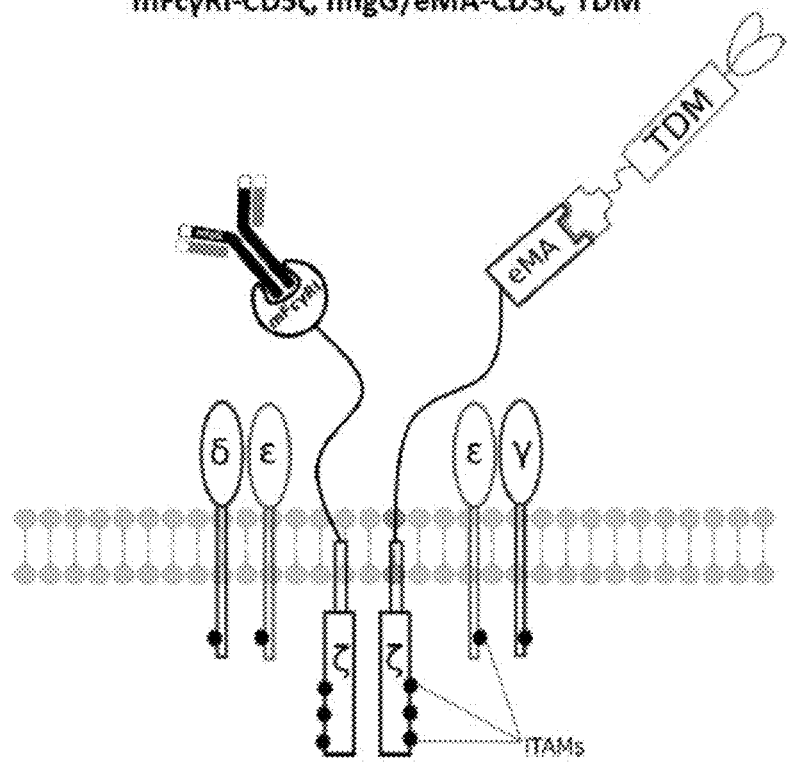
Figure 114:
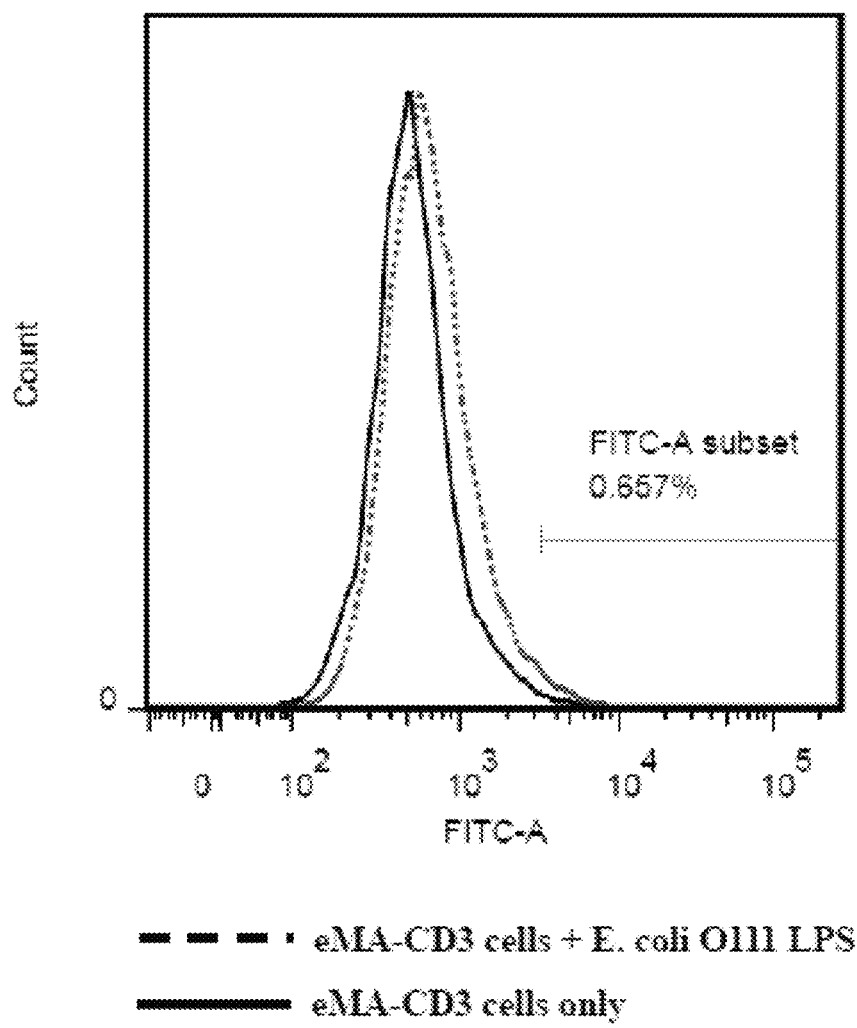
Figure 115:
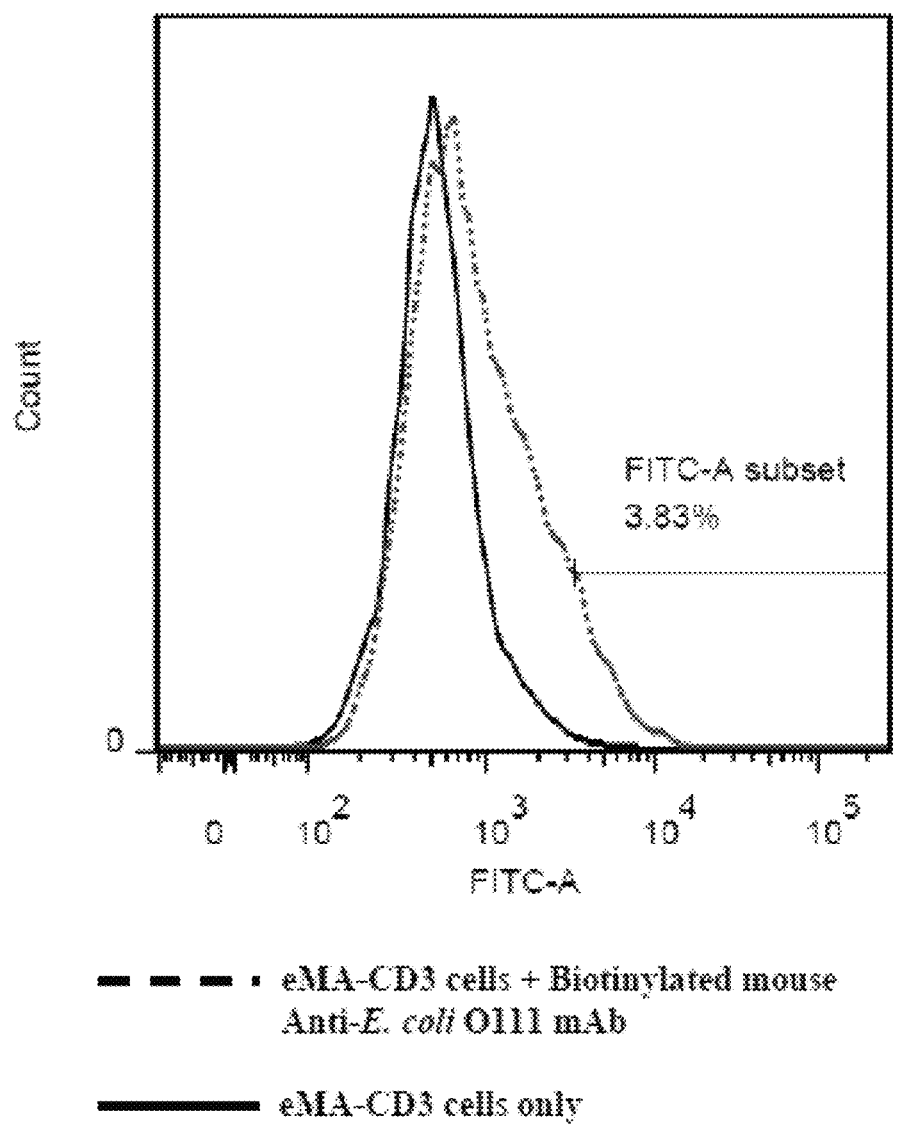
Figure 116:
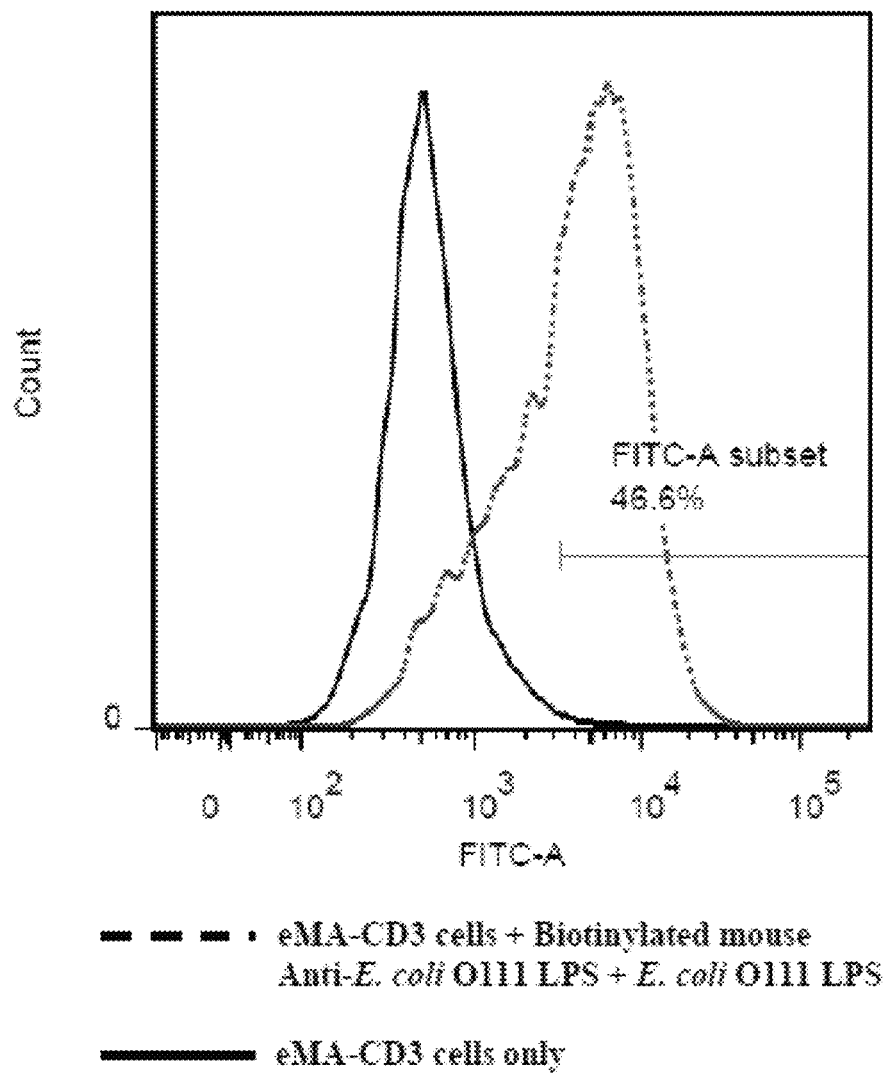
Figure 117:
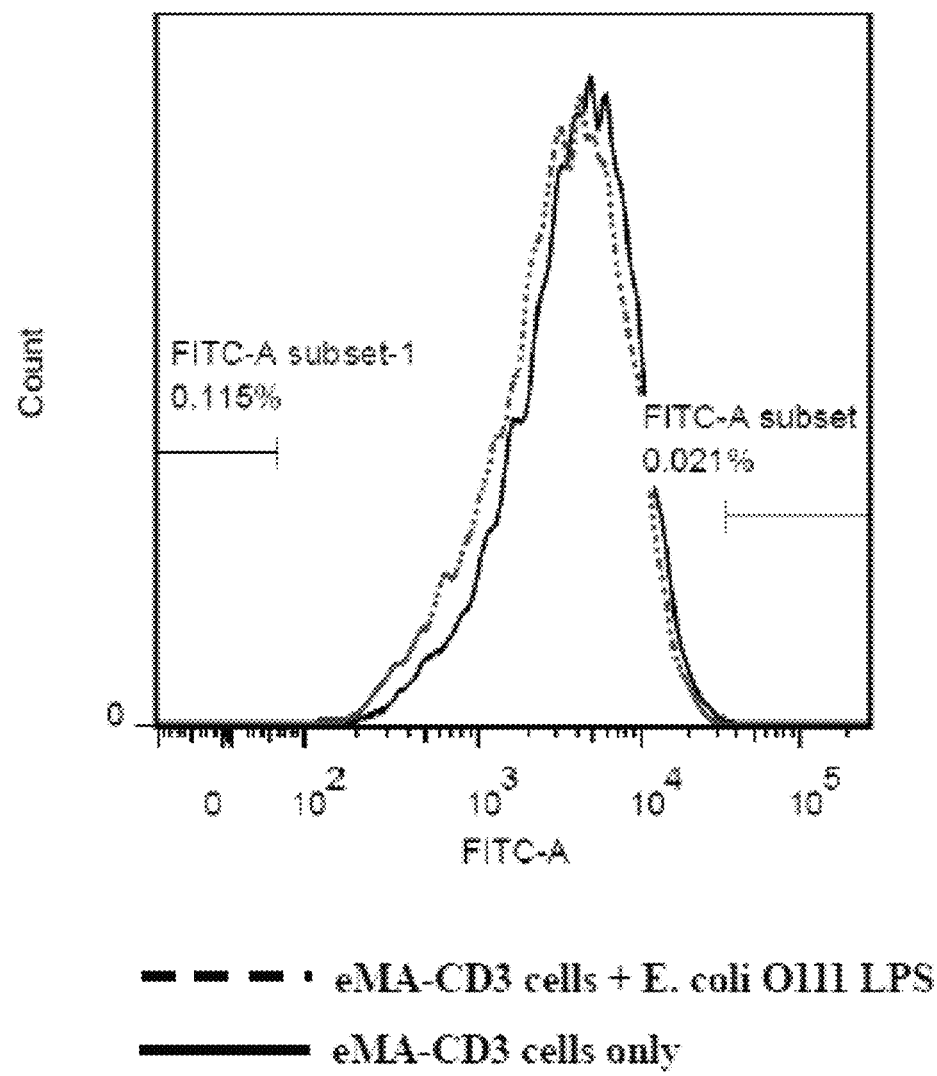
Figure 118:
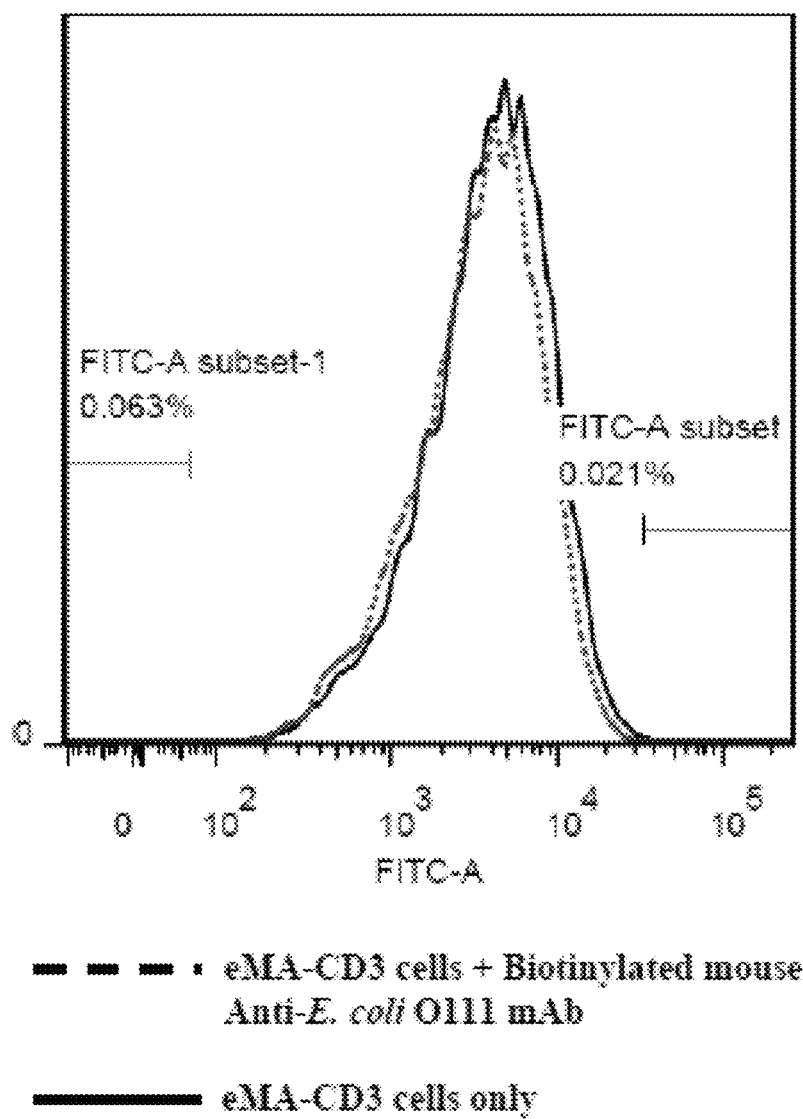
Figure 119:
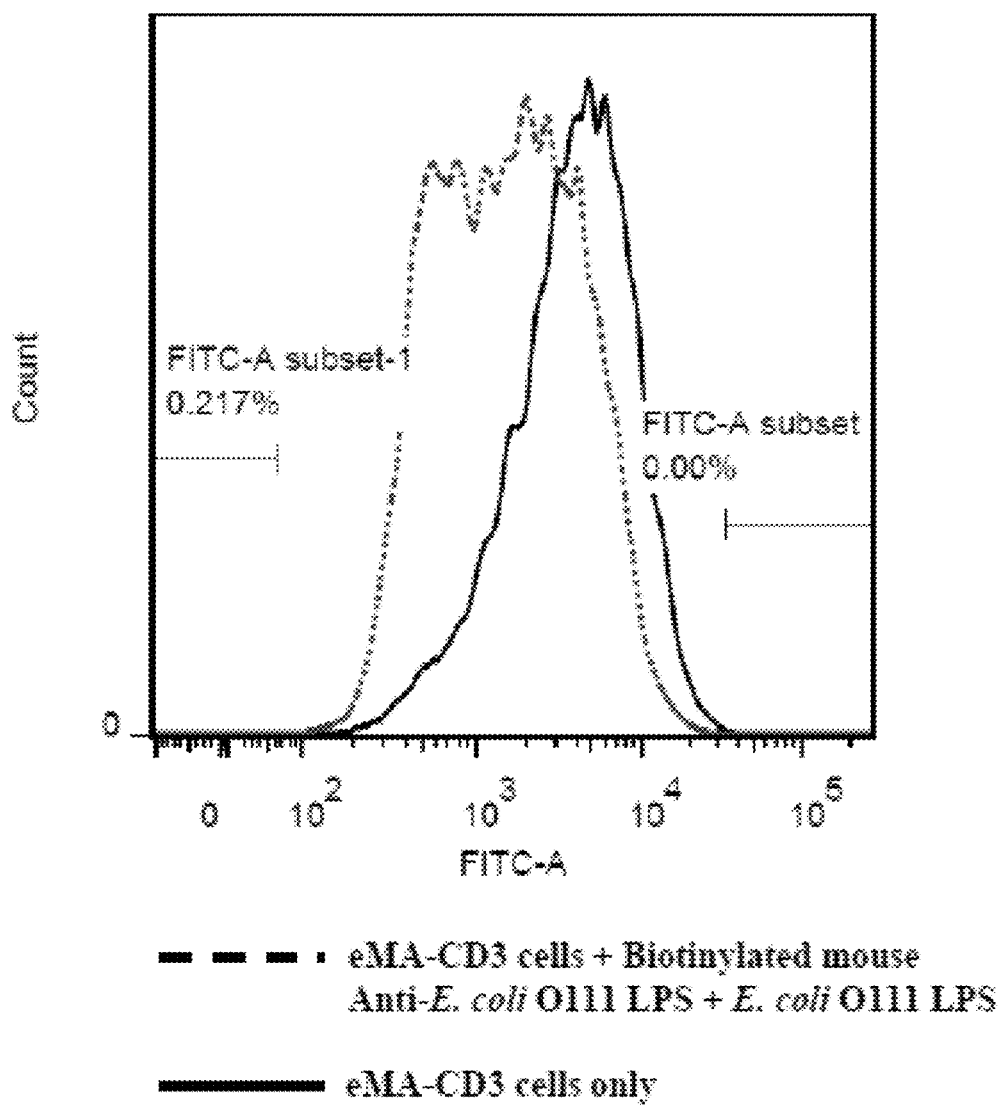

Activation Marker Expression Assay: When the programmable immunocyte receptor cells are incubated with biotinylated target detector molecules and their specific targets, cells are activated. Upon activation, T cells will up or down-regulate a variety of T cell activation markers in a predictable pattern. In this assay, two T cell activation markers (CD69 and CD62L) were selected for analysis following cell activation. FIGS. 77-79 are graphs showing the results of an activation marker expression assay (expression levels of CD69 on eMA-CD3ζ cells upon activation using biotinylated mouse Anti-*E. coli* O111 LPS antibody and *E. coli* O111 LPS), wherein FIG. 114 shows the results for cells incubated with LPS only; FIG. 115 shows the results for cells incubated with antibody only; and FIG. 116 shows the results for cells incubated with antibody and LPS; and FIGS. 80-82 are graphs showing the results of an activation marker expression assay (expression levels of CD62L on eMA-CD3 cells upon activation using biotinylated mouse Anti-*E. coli* O111 LPS antibody and *E. coli* O111 LPS), wherein FIG. 117 shows the results for cells incubated with LPS only; FIG. 118 shows the results for cells incubated with antibody only; and FIG. 119 shows the results for cells incubated with antibody and LPS. For determining expression levels of CD69, cells (1×10$^6$ cells/sample) were seeded in a 12 well plate and then activated by the addition of 10 μg/mL biotinylated mouse mAb against *E. coli* O111 LPS and *E. coli* O111 LPS. Samples were incubated at 37° C., 5% $CO_2$ for 24 hours to allow for expression of T cell activation markers. The expression levels of CD69 and CD62L were analyzed by flow cytometry using mouse mAb against the markers as a primary antibody and AlexaFluor647 goat anti-mouse IgG as a secondary antibody.

Target Cell Lysis Assay. The XTT (sodium 3'-[1-[(phenylamino)-carbony]-3,4-tetrazolium]-bis (4-methoxy-6-nitro) benzene-sulfonic acid hydrate) Cell Viability Assay, purchased from ThermoFisher Scientific, is a colorimetric assay based on the reduction of XTT by actively respiring, viable cells. The XTT Cell Viability Assay was used to assess target cell lysis by the engineered Jurkat eMA-CD3ε cells (effector T cells) after the addition of biotinylated antibodies against cell surface markers expressed by the target cells.

Assay Design: Raji cells express CD19 (cancer marker) on the surface while the K562 cells don't express this marker. The goal of this experiment was to confirm Raji (CD19+) cell lysis when incubated with biotinylated anti-CD19 antibody and Jurkat eMA-CD3ε cells (effector T cells). Three negative control conditions were designed to assess the specific cytotoxicity of Jurkat eMA-CD3ε cells (effector T cells) against Raji cells when incubated with the correct biotinylated antibody: (i) The first negative control was K562 (CD19−) cells incubated with biotinylated anti-CD19 antibody and the Jurkat eMA-CD3ε cells (effector T cells); (ii) The second negative control was Raji cells incubated with Jurkat eMA-CD3ε cells (effector T cells) and a biotinylated antibody against a marker (EGFR) which is not expressed on Raji cells; (iii) The third negative control was Raji cells incubated with Jurkat eMA-CD3ε cells (effector T cells) and a non-biotinylated anti-CD19 antibody which did not bind to the eMA-CD3ε receptor of the Jurkat eMA-CD3ε cells (effector T cells). Both anti-CD19 and anti-EGFR recombinant monoclonal mouse IgG2a antibodies were purchased from Absolute Antibody and biotinylated using the EZ-Link NHS-Biotin Kit from ThermoFisher Scientific. The number of biotins per molecule of IgG was determined to be 4-5 using the Pierce Biotin Quantitation Kit (ThermoFisher Scientific).

Procedure: Raji and K562 cells were obtained from ATCC and cultured in RPMI 1640, 10% FBS, 1× Pen/Strep following ATCC specifications for use as target cells in this experiment. Effector and target cells were plated at a ratio of 2:1 in a total of 100 μL DMEM, 10% FBS per well in a 96 well plate. Specific antibodies were added to the appropriate samples at a final concentration of 10 μg/mL. An additional sample containing DMEM, 10% FBS only was added to account for background absorbance. A sample containing target cells only, plated in the same number as in the experimental samples, was added to account for maximum reduction of XTT by target cells. A sample of effector cells only, plated in the same number as the experimental samples, was added to account for XTT reduction contributed by the effector cells. All samples were plated in triplicate, and the plate was incubated at 37° C., 5% $CO_2$ for 48 hours. After incubation, the XTT solution was prepared and added to the samples following the protocol provided by ThermoFisher Scientific, and incubated for 2 hours at 37° C., 5% $CO_2$. The viability of the cells was assessed by measuring the OD at a wavelength of 450 nm and a reference wavelength of 650 nm. The mean OD and Standard Deviation was calculated for each sample type. The percent of viable target cells was calculated as follows: % Viability of Target Cells=((OD experimental wells−OD effector only wells)/(OD target cell only wells−OD medium))×100.

Figure 120:
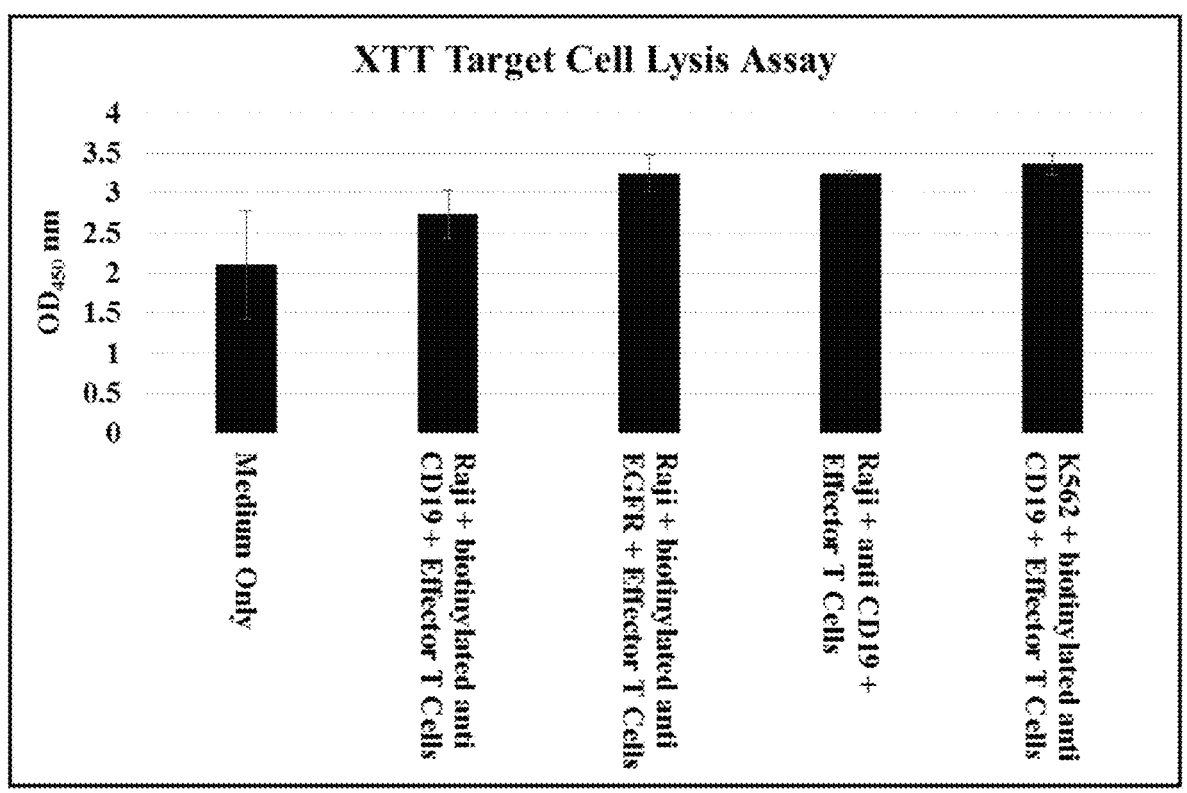
FIG. 120 is a graph showing the average absorbance readings at $OD_{450}$ of different samples after incubation with XTT reagent for 2 hours: Medium Only; Raji+ biotinylated anti-CD19+ effector T cells; Raji+ biotinylated anti-EGFR+ effector T cells; Raji+ anti-CD19+ effector T cells; and K562+ biotinylated anti-CD19+ effector T cells.
Figure 121:
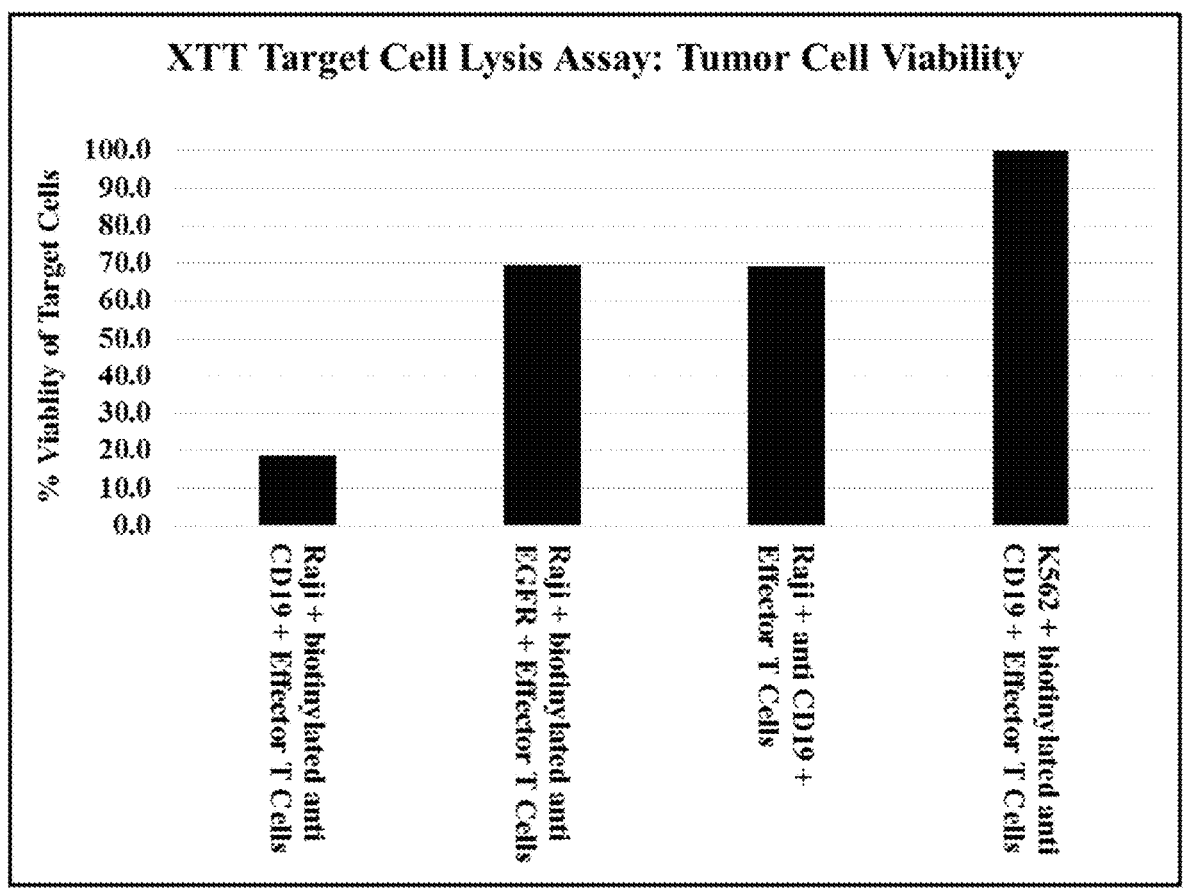
FIG. 121 is a graph showing the calculated % Viability of Target Cells in different samples: Raji+ biotinylated anti-CD19+ effector T cells; Raji+ biotinylated anti-EGFR+ effector T cells; Raji+ anti-CD19+ effector T cells; and K562+ biotinylated anti-CD19+ effector T cells.

Results: FIG. 120 is a graph showing the average absorbance readings at $OD_{450}$ of different samples after incubation with XTT reagent for 2 hours: Medium Only; Raji+ biotinylated anti-CD19+ effector T cells; Raji+ biotinylated anti-EGFR+ effector T cells; Raji+ anti-CD19+ effector T cells; and K562+ biotinylated anti-CD19+ effector T cells. FIG. 121 is a graph showing the calculated % Viability of Target Cells in different samples: Raji+ biotinylated anti-CD19+ effector T cells; Raji+ biotinylated anti-EGFR+ effector T cells; Raji+ anti-CD19+ effector T cells; and K562+ biotinylated anti-CD19+ effector T cells. The results in FIG. 120 show that the absorbance readings at $OD_{450}$ of the Raji+ biotinylated anti-CD19+ effector cell sample was lower (2.74) than the other samples (3.25-3.36) indicating a decrease in cell viability due to target cell lysis. The results in FIG. 121 show the calculated values for percent viability of target cells after normalization to 100%. The Raji+ biotinylated anti-CD19+ effector cells sample had a significantly lower percent viability of target cells (18.6%) when compared to the control samples which had target cell viabilities between 69.2% and 100% as depicted in FIG. 121. These results show that Jurkat eMA-CD3ε cells (effector T cells) lysed the target Raji cells and that the lysis is specific to cells with a selected marker coupled with the addition of the corresponding biotinylated antibody against that marker.

Cell Preservation

The present invention also includes a method for modified/engineered TCR complex cell preservation that allows the engineered cells to be frozen at −80° C. until the time of use. To use the cells, the cells are removed from the freezer and thawed at room temperature for 15 minutes and then used for activation. The eMA-CD3ε cells can be frozen at −80° C., thawed at room temperature for 15 minutes, and activated using biotinylated TDMs and target antigens.

For therapeutics, engineered cells can be thawed then tested against a cocktail of biotinylated TDMs until a working one is found, then cells can be infused into a patient. This kind of arrangement provides flexibility in the treatment process. Once cells are harvested from individuals, they are isolated, activated and genetically engineered to generate universal adaptor receptor-expressing cells, and then expanded and frozen using our invention. To freeze the cells, expanded cells are mixed with 0.1% Pluronic F68 and 7% glycerol at a concentration of $1.6 \times 10^6$ Cells/90 μL RPMI and frozen at −80° C. Cells will remain viable for at least 6 months or longer.

Target Detection Molecules (TDMs)

The programmable immunocyte receptor complex cell system of the present invention is capable of binding to any biotinylated target detection molecule (TDM), whereby the biotinylated TDM then directs the engineered cells to specific targets such as, cancer cells. The engineered cells are activated upon binding to the targets. The functionality of the present invention for both diagnostic and therapeutic applications involves the use of high quality, operative TDMs. Accordingly, the present invention includes a production scheme for different TDMs designed for use with the immunocyte receptor complex cell system. Commercially available TDMs are also compatible with the present invention. TDMs are capable of detecting different pathogens including, but not limited to; bacteria, viruses, fungi, protozoa, biomarkers, cell receptors, proteins, nucleic acids, peptides, metabolites or other small molecules. A TDM may contain multiple binding domains for different epitopes of one or more targets. TDMs may include antibodies such as IgG, Fab, F(ab')$_2$, scFv, diabody, triabody, scFv-Fc, nanobody, minibody, VHH, camelid heavy chain IgG, V-NAR, shark IgNAR, IgM, IgA, IgE, IgD, etc.; an aptamer, such as oligonucleotide e.g., DNA, RNA or XNA, peptide, etc.; carbohydrates; or other synthetic molecules. A TDM can be conjugated to biotin or biotin derivative (with adjustable linker arm) that functions as an effector moiety to trigger an immune response, providing an alternative to Fc mediated effector functions. This is a substantial advantage for clinical applications because it eliminates non-specific binding to cells which have Fc receptors (e.g., dendritic cells, NK cells and macrophages) which may cause detrimental health effects (see, Masuda et al., *Role of Fc Receptors as a Therapeutic Target*, Inflamm Allergy Drug Targets. 8(1): 80-86 (2009). TDMs may bind to or otherwise recognize antigenic determinants or epitopes recognized by antibodies, B cells or T cells. Such antigenic determinants include linear epitopes as well as conformational epitopes, as well as epitopes recognized on an antigen-presenting cell, such as those presented in the context of an MHC class I or MHC class II molecule.

TDMs can be generated by different technologies including immunization and serum collection, hybridoma selection, single B cell sorting, single plasma cell sorting, phage display, yeast display, bacterial display, ribosome display, mRNA display, yeast two-hybrid system and SELEX. When the sequence of a TDM is identified, it can be genetically modified into different forms (e.g., scFv). TDMs can be expressed and purified from transformed bacteria (e.g., *E. coli*) or transfected mammalian cells (e.g., HEK293) for further applications. A TDM can be chemically or enzymatically biotinylated, depending on whether the molecule has appropriate glycosylation or lysine residues and whether it contains an AviTag™ (see, for example, U.S. Pat. Nos. 5,932,433, 5,874,239 and 5,723,584, which are incorporated by reference herein, in their entirety, for all purposes). Chemical biotinylation is ideal for biotinylating heavily glycosylated antibodies because carbohydrate residues on the Fc portion of a TDM can be oxidized to aldehydes by sodium periodate followed by conjugation to Hydrazide-PEG4-Biotin. Alternatively, an AviTag™ can be genetically fused to the C-terminus of a TDM away from the paratope. Untargeted, uncontrolled biotinylation can result in undesirable TDMs especially if lysine residues are in the paratope region of the TDM. An AviTagged antibody can be biotinylated using biotin ligase e.g. the BirA-500 kit (Avidity) as follows: Briefly, 10 mM ATP, 10 mM MgOAc, 50 μM D-biotin and biotin ligase are mixed with the antibody in 0.05M Bicine buffer at pH 8.3 and incubated at 30° C. for 1 hour. The present invention includes the following TDMs.

mAb (IgG2c) against *E. coli* O111 (hereinafter, 1F11): This antibody was generated through the hybridoma system and was used with mFcγRI-CD3ζ cells for *E. coli* O111 detection and effector cell activation.

AviTagged 1F11 (IgG2a): This TDM was generated through class switch of 1F11 from IgG2c to IgG2a and addition of AviTag to the C-terminal end of the Fc region. It is an improved version of 1F11 because it binds mFcγRI-CD3ζ with much higher affinity than the IgG2c version. This antibody was cloned and expressed in FreeStyle™ 293-F cells through secretion into culture medium. Protein G resin (Thermo Scientific) was used to purify the antibody from cell supernatant.

Biotinylated, AviTagged 1F11 (IgG2a): This is the biotinylated version of AviTagged 1F11 (IgG2a) and it can be used with both FcγRI-CD3ζ and eMA-CD3ε cells. We use this TDM for *E. coli* O111 detection and effector cell activation. It was generated through biotinylation of the purified AviTagged 1F11 using biotin ligase.

Biotinylated, AviTagged 1F11 scFv: This TDM was designed and constructed from the original variable region sequence of 1F11 mAb. It was constructed with an AviTag and is co-expressed with the biotin ligase enzyme (BirA) in an *E. coli* strain. Both genes are IPTG-inducible, so IPTG and biotin were added to the culture medium to induce protein expression and biotinylation. The biotinylated scFv was extracted by BugBuster Master Mix (MilliporeSigma) and purified by way of streptavidin mutein matrix (Sigma-Aldrich).

AviTagged 1F11 Fab: The Fab version of 1F11 was designed and constructed with an AviTag and a signaling sequence to export and secrete into culture medium during expression in FreeStyle™ 293-F cells.

V-NAR Antibody Against PBP2A: Shark IgNAR antibody library was screened (Exommune, Gaithersburg, MD) for specific higher binders against MRSA (PBP2A). Seven sequences were generated and were used for constructing TDMs with AviTag to express and biotinylate in an *E. coli* strain. The resulting TDMs were purified on a streptavidin column and used for MRSA detection and effector cell activation.

IgNAR Antibody Against MERS-CoV Spike Protein: Seven sequences were obtained from Exommune (Gaithersburg, MD) and were used for constructing TDMs for detection of MERS-CoV virus and effector cell activation. The expressed TDMs were purified on a streptavidin column before use.

Human Fab Against PBP2A Protein: The HuCAL PLATINUM® phage library was screened for human Fab antibodies recognizing PBP2A (MRSA) protein. Sequences from high binders were used to construct and express HisTagged, AviTagged Fab antibodies to be expressed in *E. coli* cells. The TDMs were extracted and purified on a Nickel-NTA column. Antibodies were biotinylated using biotin ligase and purified on a streptavidin column before using with eMA-CD3ε cells for target detection and effector cell activation.

The Pierce Biotin Quantitation Kit (Thermo Scientific) was used to determine the biotinylation levels of the labeled TDMs. The HABA (2-(4-hydroxyazobenzene) benzoic acid)/avidin complex was dissolved in ultrapure water. The absorbance of the solution was measured at 500 nm. The biotinylated antibody was then introduced into the HABA/avidin complex, resulting in a change in absorbance at 500 nm. The change in absorbance at 500 nm was used to calculate the moles of biotin per mole of protein.

Figure 106:
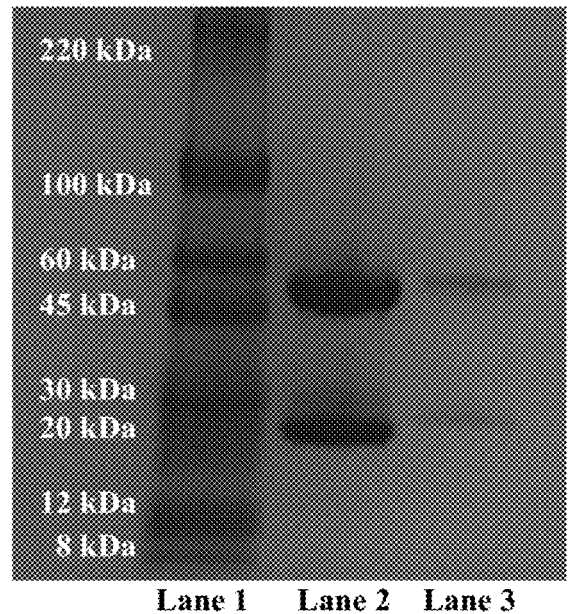
Figure 107:
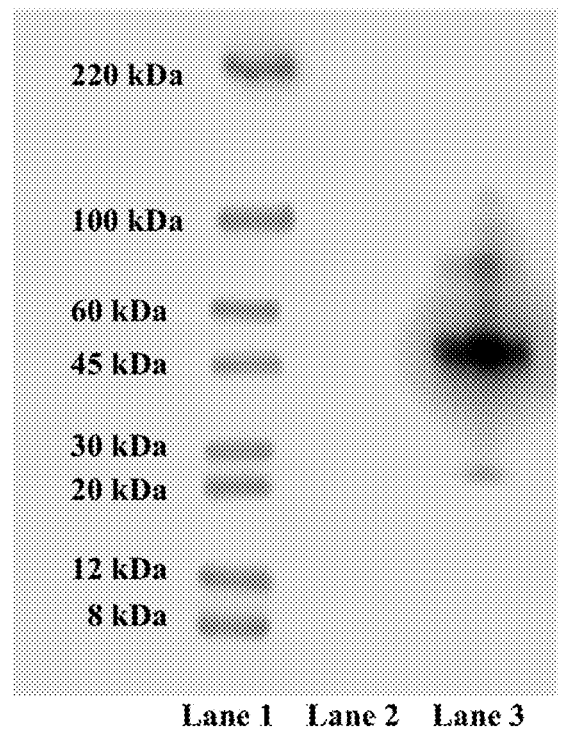
Figure 108:
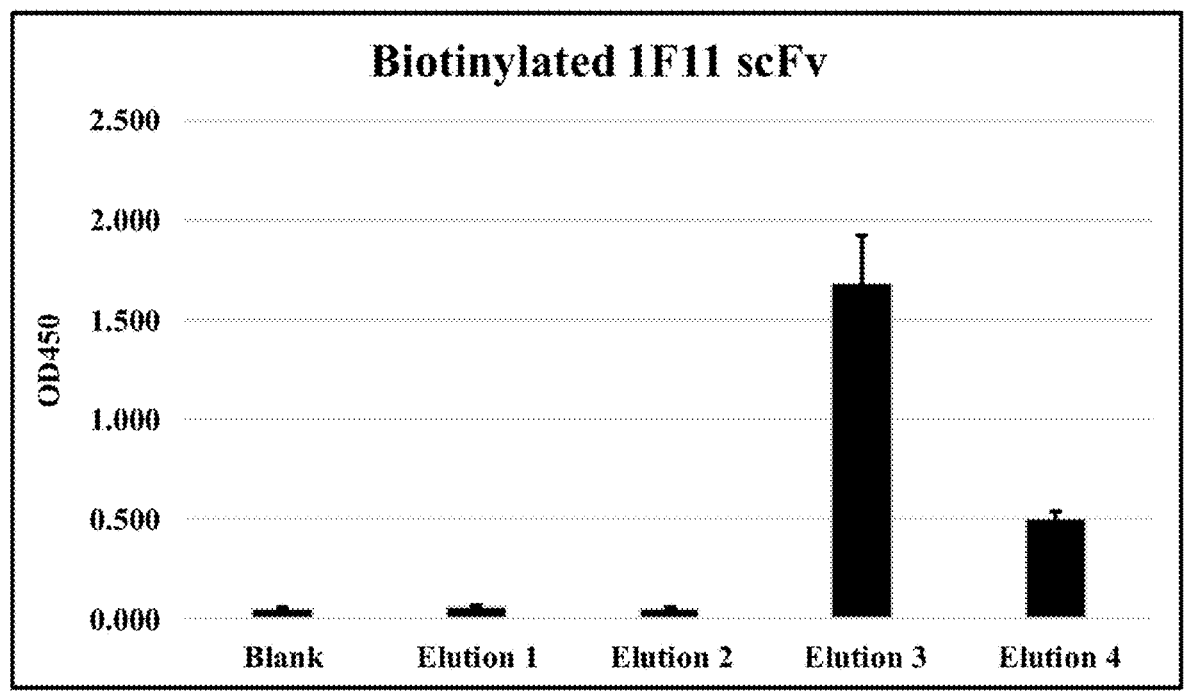
FIG. 108 is a bar graph showing the results of an ELISA analysis of elution fractions from biotinylated 1F11 (mouse mAb against *E. coli* O111 LPS) purification, wherein the fractions were tested against HRP-conjugated anti-biotin IgG.

Following purification and biotinylation, all TDMs are analyzed for biotinylation and purity by SDS-PAGE and Western-blot. To detect mouse antibodies, Goat Anti-Mouse IgG-HRP (Sigma catalog number AP503P) was used directly during blotting. To detect antibodies with an Avi-Tag, Biotin Ligase Epitope Tag Antibody (Rockland catalog number 100-401-B21) was used as the primary antibody with Goat Anti-Rabbit IgG-HRP (Santa Cruz catalog number SC-2922) as the secondary antibody during Western-blot. To detect biotinylated antibodies, Anti-Biotin HRP (Abcam catalog number ab6651) was used directly during Western-blot. Examples of a Coomassie stained gel and the corresponding Western-blot are shown in FIGS. 106 and 107. FIGS. 106-107 are images of SDS-PAGE and Western-blot analysis of purified, biotinylated 1F11 IgG2a; wherein FIG. 106 is a photograph of a 4-20% SDS-PAGE gel showing the protein standard in lane 1, the purified, non-biotinylated protein in lane 2 and the purified, biotinylated protein in lane 3; and wherein FIG. 107 is a photograph of a Western-blot analysis showing the protein standard in lane 1, the purified, non-biotinylated protein in lane 2 and the purified, biotinylated protein in lane 3. To determine the concentration of antibodies after extraction and purification, the Pierce BCA Protein Assay Kit (Thermo catalog number 23227) was used.

Figure 109:
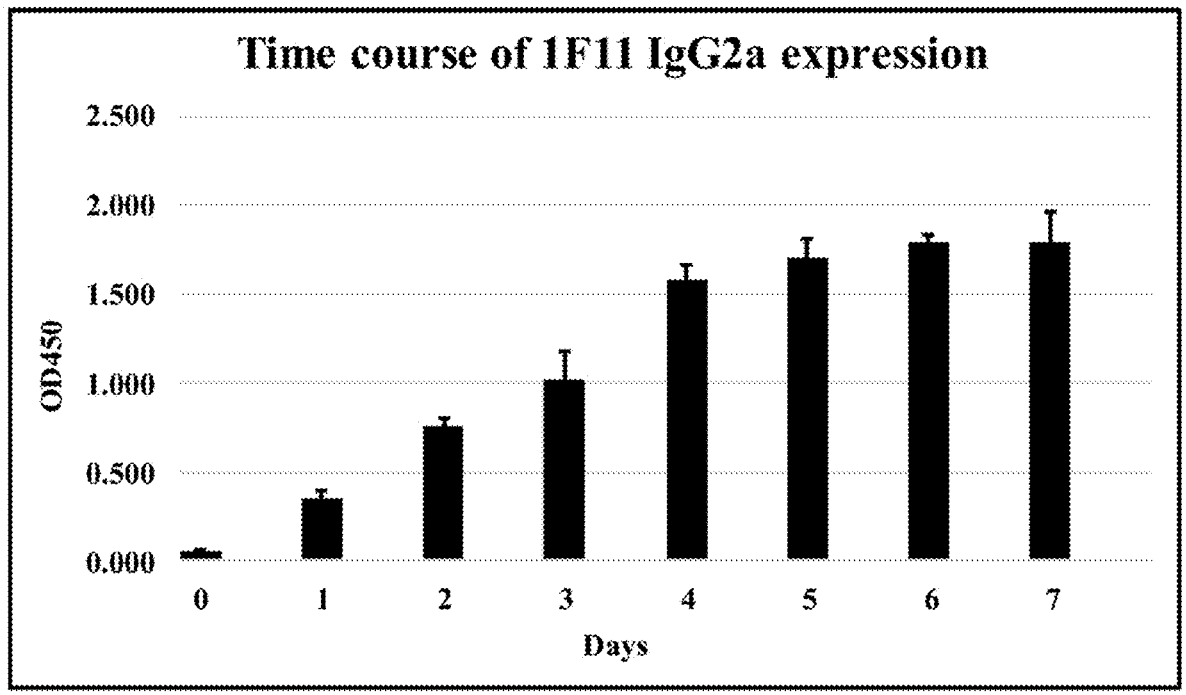
FIG. 109 is a bar graph showing an ELISA time course characterization of 1F11 (mouse mAb against *E. coli* O111 LPS) IgG2a antibody expression in FreeStyle 293-F cell supernatant.
Figure 110:
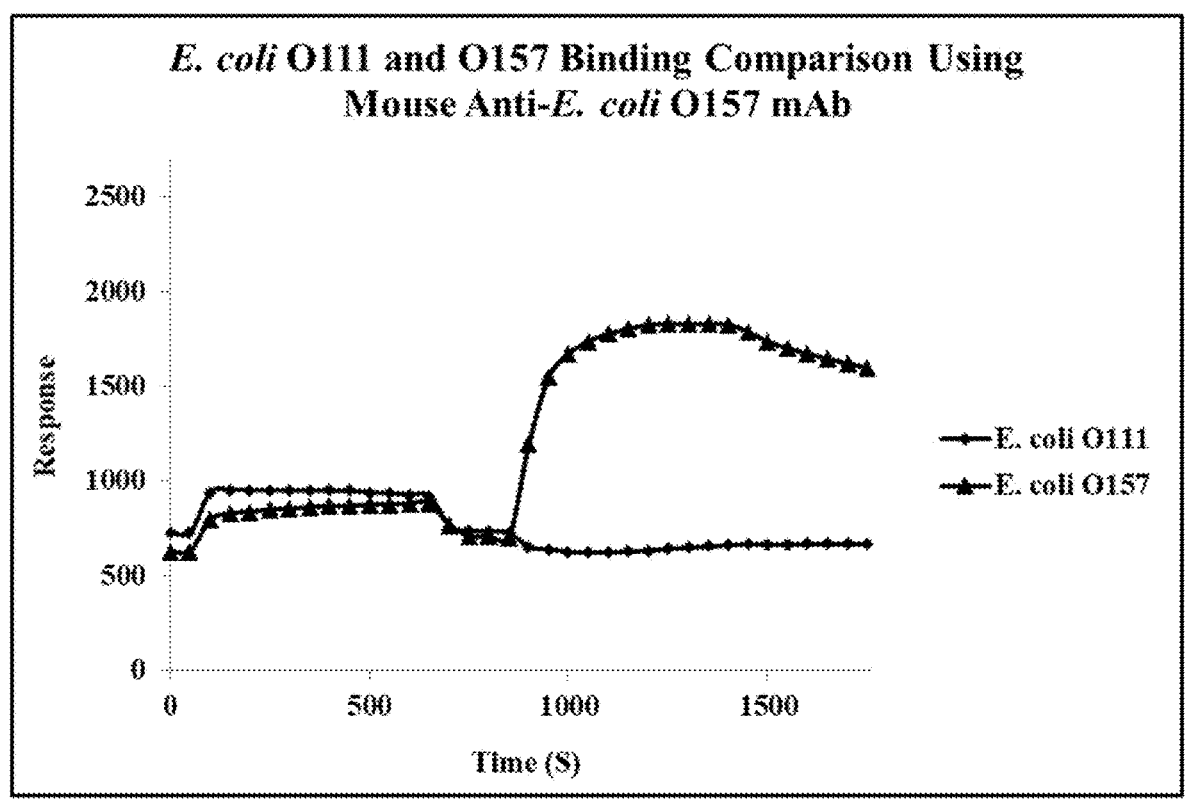
FIG. 110 is a graph showing the results of a Biacore analysis of the binding of an *E. coli* O157 specific antibody (mAb FF754) to *E. coli* O157 and *E. coli* O111, wherein the results confirm that mAb FF754 is specific for *E. coli* O157.
Figure 111:
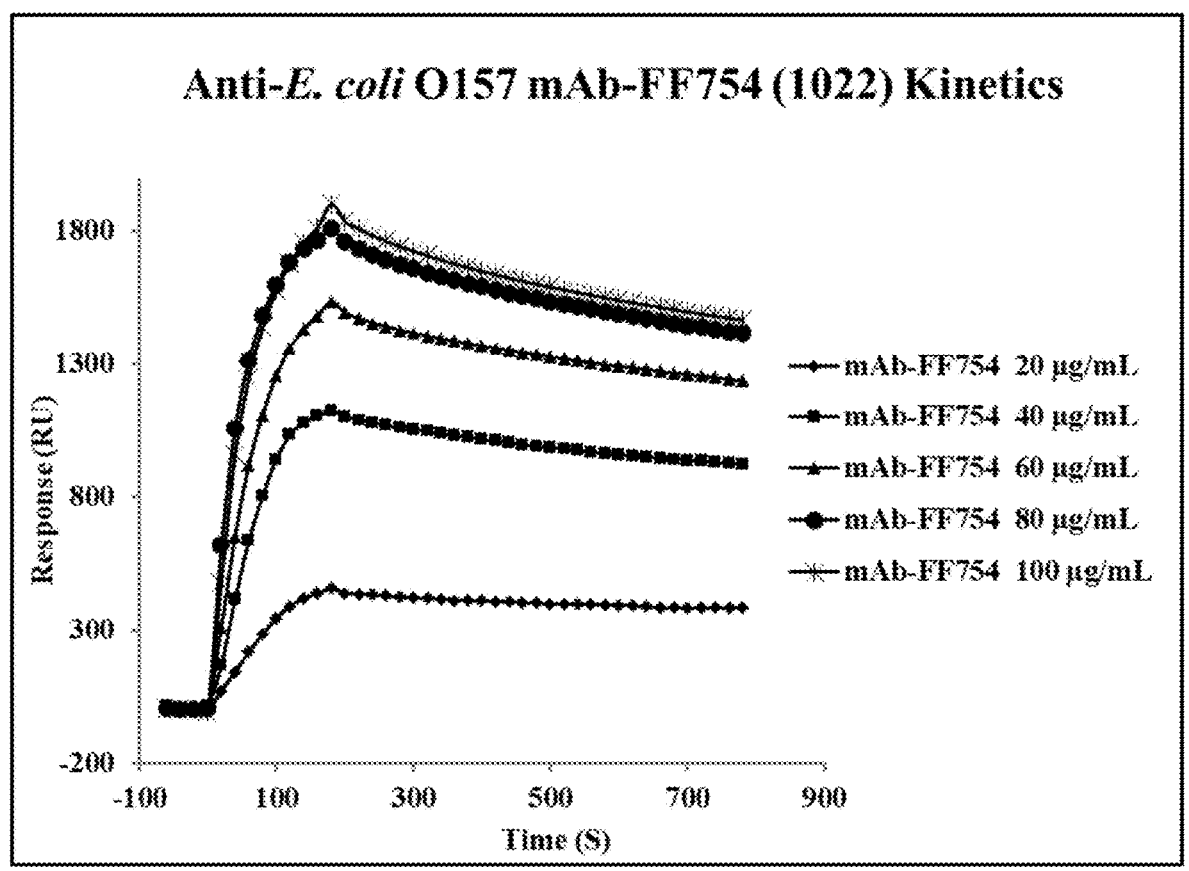
FIG. 111 is a graph showing the results of a Biacore Analysis of the Kinetics of the interaction between an *E. coli* O157 specific antibody and *E. coli* O157 using different concentrations of the antibody.

Antibody-antigen interaction was analyzed by ELISA. A 96-well microtiter plate was coated with antigen (*E. coli* O111 LPS) at 4° C. overnight. The plate was washed to remove unbound antigen followed by blocking with 5% w/v BSA (or nonfat dry milk) at room temperature for 1 hour. Serial dilutions of samples, including standards, positive and negative controls, and unknowns were added on the plate. After an incubation of 1 hour, the plate was washed three times and HRP-conjugated detection antibody was added and incubated for 1 hour. The plate was washed and a 3,3',5,5'-Tetramethylbenzidine substrate solution was added for color development. The reaction was stopped by 1M HCl and the plate was immediately read using a plate reader at $OD_{450}$. FIG. 109 is a graph showing the results of an ELISA analysis of elution fractions from biotinylated 1F11 scFv purification, wherein the fractions were tested against HRP conjugated anti-biotin IgG. Each well was coated in triplicate with 500 µg/mL of *E. coli* O111 LPS. Four eluted fractions were tested for the presence of 1F11 scFv. Antibody storage buffer was used as blank. FIG. 110 is a graph showing an ELISA time course characterization of 1F11 IgG2a antibody expression in FreeStyle 293-F cell supernatant. The ELISA plate was coated with *E. coli* O111 LPS. Samples were collected over a 7-day period and analyzed for the presence of 1F11 IgG2a antibody using HRP conjugated Goat Anti-Mouse IgG γ chain antibody. Fresh cell culture media was used as blank.

Figure 74:
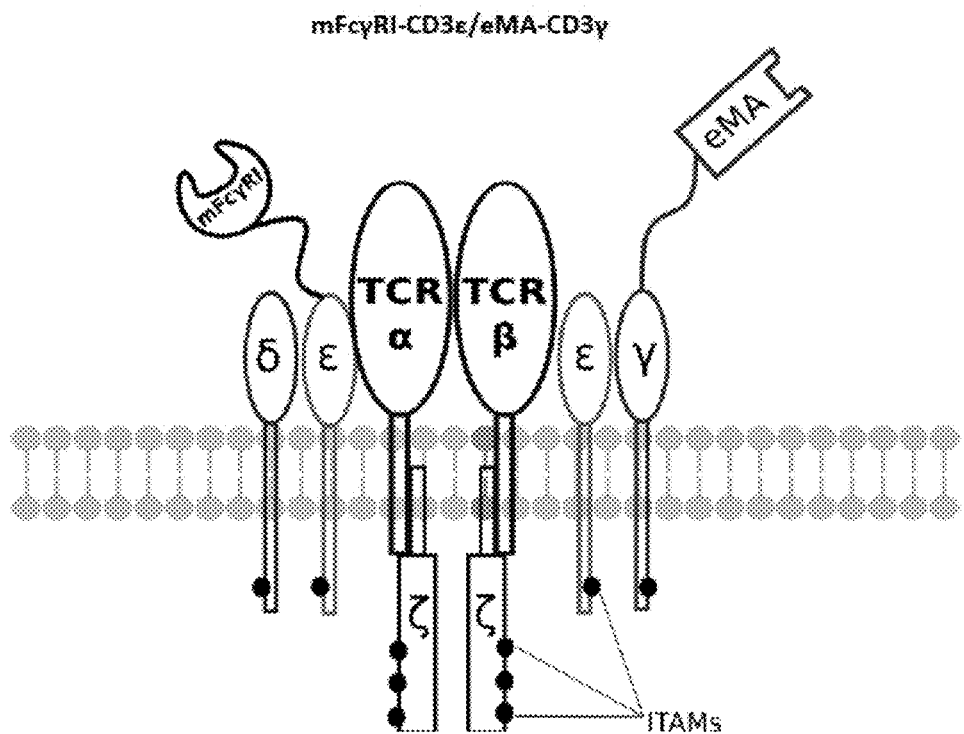

Biacore SPR was used to analyze generated TDMs and other commercial antibodies before use. This process enabled ranking and selection of the best TDMs for use with the programmable immunocyte receptor complex cell system. For each antibody, TDM-target interaction, binding affinities, and kinetic rate constants were measured, thereby permitting the kinetic and equilibrium constants for each TDM to be determined. FIG. 109 is a graph showing the results of a Biacore analysis of the binding of an *E. coli* O157 specific antibody (mAb FF754) to *E. coli* O157 and *E. coli* O111, wherein the results confirm that mAb FF754 is specific for *E. coli* O157. FIG. 74 is a graph showing the results of a Biacore Analysis of the Kinetics of the Interaction between an *E. coli* O157 specific antibody and *E. coli* O157 using different concentrations of the antibody.

The present invention provides a universal, adaptable and/or programmable immunocyte receptor complex cell system that can be used with any biotinylated target detector molecule (TDM). These engineered cells are activated with the appropriate TDMs and specific targets to induce cytokine release. The engineered cells can be frozen, thawed at room temperature for 15 minutes, and immediately used in activation assays. This system offers many advantages over the current CAR T cell systems. Rather than creating artificial receptors, this invention harnesses the native T cell receptor complex signaling capacity through simple modifications of the complex. This allows engineered cells to function as close to normal as possible resulting in improved signaling, cell proliferation, extension and persistence compared to CAR T cells. By using eMA and mSA2 as universal receptors, cell activation can be modulated by adjusting the TDM dosage or use biotin (or a biotin analog) as an "on/off" or a signal "volume control" switch whenever necessary. Additionally, engineered cells can be used to quickly screen for more desirable TDMs and pair them before infusing into patients. A library of TDMs can be generated using known cancer markers so that extracted, engineered patient cells can be quickly tested against a cocktail of TDMs to find the most effective treatment. This invention also includes the use of Aequorin as a tool for better, faster and safer ways of testing engineered cells in vitro before infusing them back into the body. A small fraction of the extracted cells can be used with Aequorin as a sample analysis to determine patient response to the TDMs. The disclosed method of freezing engineered cells confers flexibility in the method of treatment using the engineered cells. This new adaptor TCR complex system is robust and any potential immunogenicity of eMA and mSA2 can be easily dealt with through minor mutations to the proteins. This invention contemplates a system wherein a healthy person submits their own extracted cells to be engineered to generate programmable immunocyte receptor complex cells that will then be tested and banked for future use or programming with specific TDMs when an illness manifests in that person.

In some embodiments, the immunocyte receptor complex will not exhibit the binding specificity of the native, unmodified receptor, for example, a modified T cell receptor will exhibit substantially only the specificity provided by the target detector molecule. This may be accomplished by substitution to one or more subunits forming the receptor's antigen binding site, or by modification of residues essential to the native antigen binding site. CAR T Cells lacking native TCR function would eliminate the possibility of off target effects that stem from the specificity of the original T cell line. Separately, elimination of the MHC I and MHC II surface proteins would reduce the ability of the hosts adaptive immune system targeting the incoming therapeutic T cells and building up rapid response rejection over time. This would also reduce the ability of the body to reject allographic T cells as non-self. T cells without MHC would still be subject to enhanced targeting by parts of the innate immune system, for example, NK cells, but these would not acquire the ability to specifically target the chimeric proteins on the therapeutic T cells.

BLASTP can be used to identify an amino acid sequence having at least 95%, 97.5%, 98%, 99% sequence identity or similarity to a reference amino acid using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise specified a similarity score for sequences disclosed herein will be based on use of BLOSUM45. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. Preferably, sequences that are similar or that have at least 95% identity with sequences disclosed herein will retain at least one function of the disclosed sequence.

While the present invention has been illustrated by the description of exemplary embodiments thereof, and while the embodiments have been described in certain detail, there is no intention to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the general inventive concept.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, and by way of example, a description of a technology in the "Background" is not to be construed as an admission that certain technology is prior art to any embodiment(s) in this disclosure. Neither is the "Summary" to be considered as an exhaustive characterization of the embodiment(s) set forth in any issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure, but should not be constrained by the headings set forth herein.

What is claimed:

1. A target detection system, comprising:
   (a) a modified receptor complex expressed by an immunocyte, wherein the modified receptor complex includes a plurality of receptor subunits including at least one CD3-delta, one CD3-gamma, one TCR alpha one TCR beta, two CD3-zeta and two CD3-epsilon, and wherein at least one of the plurality of receptor subunits has been engineered or modified to include either:
      (i) a biotin-binding component that binds to a target detector molecule that is separate from the receptor complex and that binds to or otherwise interacts with a predetermined target; or
      (ii) an FcγRI receptor component that binds to a target detector molecule that is separate from the receptor complex and that binds to or otherwise interacts with a predetermined target; and
   (b) a target detector molecule that is not expressed by the immunocyte and that is separate from the receptor complex, wherein the target detector molecule:
      (i) is not an antibody and includes a biotin moiety and a paratope or ligand that is specific for the predetermined target; or
      (ii) is an antibody that binds to either to the biotin-binding component or to the FcγRI receptor component and that is specific for the predetermined target.

2. The target detection system of claim 1, wherein the plurality of receptor subunits are T cell receptor subunits.

3. The target detection system of claim 1, wherein the receptor subunit that has been engineered or modified to include a biotin-binding component is the CD3-epsilon subunit.

4. The target detection system of claim 1, wherein the immunocyte is a CD4+ T cell, a CD8+ T cell, γδ T cell, or allogeneic cell.

5. The target detection system of claim 1, wherein the biotin-binding component is monomeric streptavidin 2 or enhanced monoavidin.

6. The target detection system of claim 1, wherein the biotin-binding component is chicken avidin.

7. The target detection system of claim 1, wherein target detector molecule further includes a stabilizing core structure.

8. The target detection system of claim 1, wherein the predetermined target is a cancer cell or cancer cell determinant of a known type, or an infectious disease agent or a determinant of an infectious disease agent of a known type.

9. The target detection system of claim 1, wherein the target detector molecule is an IgG antibody.

10. The target detection system of claim 1, wherein the system is adapted for diagnostic use.

11. The target detection system of claim 1, wherein the system is adapted for therapeutic use.

12. A target detection system, comprising:
    (a) a modified receptor complex expressed by an immunocyte, wherein the modified receptor complex includes a plurality of T cell receptor subunits including at least one CD3-delta, one CD3-gamma, one TCR alpha one TCR beta, two CD3-zeta and two CD3-epsilon, and wherein at least one of the plurality of T cell receptor subunits has been engineered or modified to include either:
       (i) a biotin-binding component that binds to a target detector molecule that is separate from the receptor complex and that binds to or otherwise interacts with a predetermined target; or (ii) an FcγRI receptor component that binds to a target detector molecule that is separate from the receptor complex and that binds to or otherwise interacts with a predetermined target; and (b) a target detector molecule that is not expressed by the immunocyte and that is separate from the receptor complex, wherein the target detector molecule:

(i) is not an antibody and includes a biotin moiety and a paratope or ligand that is specific for the predetermined target; or (ii) is an antibody that binds to either to the biotin-binding component or to the FcγRI receptor component and that is specific for the predetermined target.

13. The target detection system of claim 12, wherein the receptor subunit that has been engineered or modified to include a biotin-binding component is the CD3-epsilon subunit.

14. The target detection system of claim 1, wherein the immunocyte is a CD4+ T cell, a CD8+ T cell, γδ T cell, or allogeneic cell.

15. The target detection system of claim 12, wherein the biotin-binding component is monomeric streptavidin 2, enhanced monoavidin, or chicken avidin.

16. The target detection system of claim 12, wherein the predetermined target is a cancer cell or cancer cell determinant of a known type, or an infectious disease agent or a determinant of an infectious disease agent of a known type.

17. The target detection system of claim 12, wherein the target detector molecule is an IgG antibody.

18. The target detection system of claim 12, wherein the system is adapted for diagnostic use or for therapeutic use.

* * * * *